(12) United States Patent
Kriesel et al.

(10) Patent No.: US 6,245,042 B1
(45) Date of Patent: Jun. 12, 2001

(54) FLUID DELIVERY DEVICE WITH TEMPERATURE CONTROLLED ENERGY SOURCE

(75) Inventors: Marshall S. Kriesel, Saint Paul; Thomas N. Thompson, Richfield, both of MN (US)

(73) Assignee: Science Incorporated, Bloomington, MN (US)

( * ) Notice: Subject to any disclaimer, the term of this patent is extended or adjusted under 35 U.S.C. 154(b) by 0 days.

(21) Appl. No.: 09/390,219

(22) Filed: Sep. 3, 1999

Related U.S. Application Data

(63) Continuation-in-part of application No. 08/919,147, filed on Aug. 27, 1997, now Pat. No. 5,961,492.

(51) Int. Cl.$^7$ .................................................. A61M 37/00
(52) U.S. Cl. ........................................ 604/132; 604/95.03
(58) Field of Search .................................. 604/890.1, 31, 604/81, 113, 132, 142, 145, 151, 153, 185, 257, 259, 95.03; 128/DIG. 1, 12; 222/94–96

(56) References Cited

U.S. PATENT DOCUMENTS

| | | |
|---|---|---|
| 3,845,770 | 11/1974 | Theeuwes et al. . |
| 3,934,584 | 1/1976 | Corio . |
| 4,166,107 | 8/1979 | Miller et al. . |
| 4,251,506 | 2/1981 | Laby . |
| 4,381,780 | 5/1983 | Holloway . |
| 4,416,659 | 11/1983 | Simpson et al. . |
| 4,959,218 | 9/1990 | Eckenhoff et al. . |
| 4,963,141 | 10/1990 | Eckenhoff . |
| 5,162,116 | 11/1992 | Shepherd . |
| 5,198,222 | 3/1993 | Scully et al. . |
| 5,277,912 | 1/1994 | Lowe et al. . |
| 5,399,162 | 3/1995 | Cselle . |
| 5,431,919 | 7/1995 | Maruyama et al. . |
| 5,562,915 | 10/1996 | Lowe et al. . |
| 5,603,955 | 2/1997 | Gehrke et al. . |
| 5,840,338 | 11/1998 | Roos et al. . |
| 5,876,741 | 3/1999 | Ron . |

FOREIGN PATENT DOCUMENTS

WO96/02276   1/1996   (WO) .

OTHER PUBLICATIONS

Intraruminal Devices by John R. Cardinal Published in Advanced Drug Delivery Reviews vol. 28, No. 3 (1997).

*Primary Examiner*—Anhtuan T. Nguyen
(74) *Attorney, Agent, or Firm*—James E. Brunton, Esq

(57) ABSTRACT

A delivery device for the administration of nutrients, drugs, vitamins, trace elements and the like to a ruminant. The device embodies a thermal expanding polymer material which, when heated by the animal's body heat functions as an internal energy source for controllably expelling the beneficial agents from the device over extended period of time of up to 200 days. The device is of a size and shape that can be introduced into the ruminant via the esophagus and is of a density such that the device will be retained within the reticulo-rumen of the animal for the effective controlled release of the beneficial agents to the animal.

19 Claims, 34 Drawing Sheets

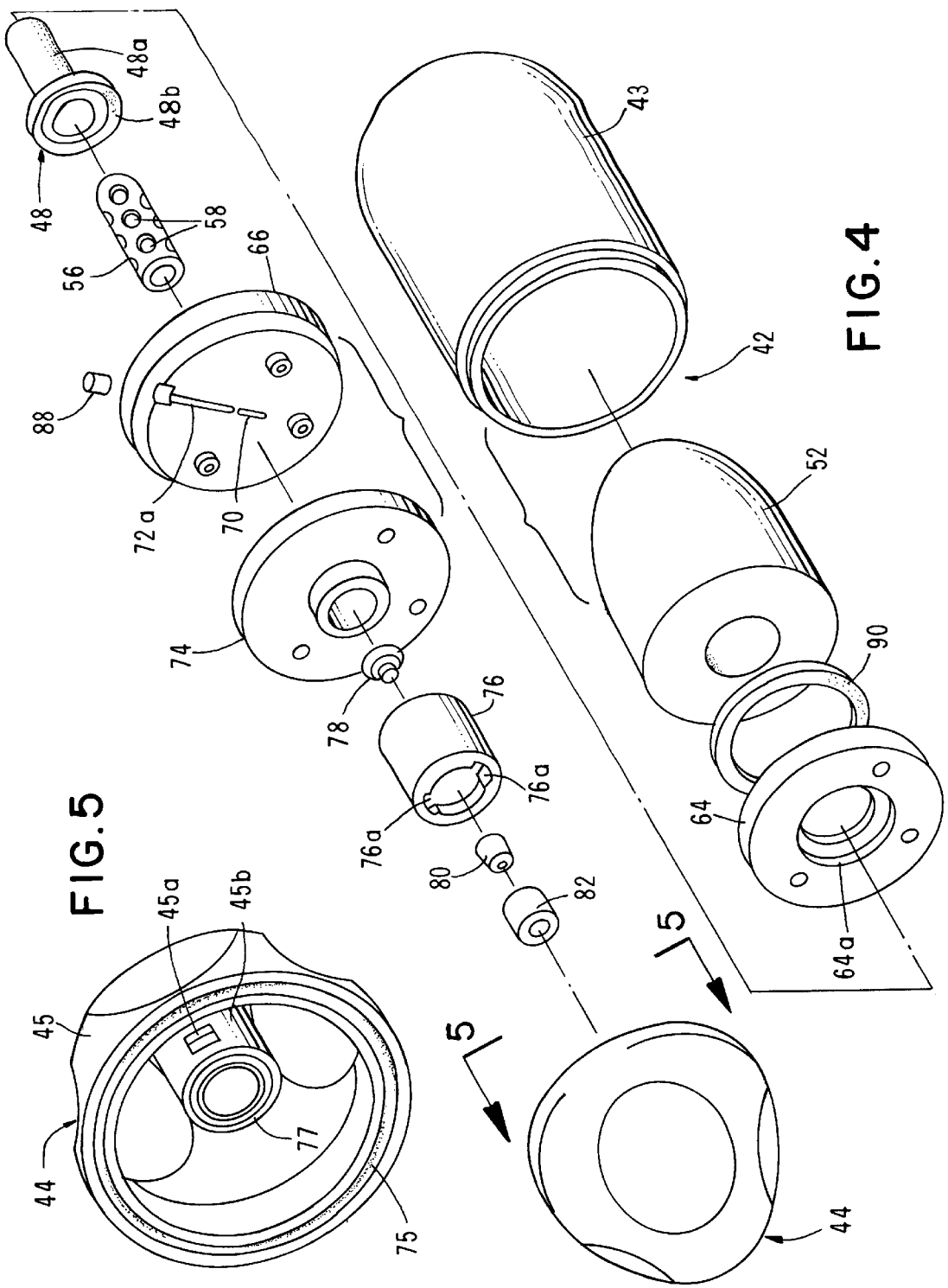

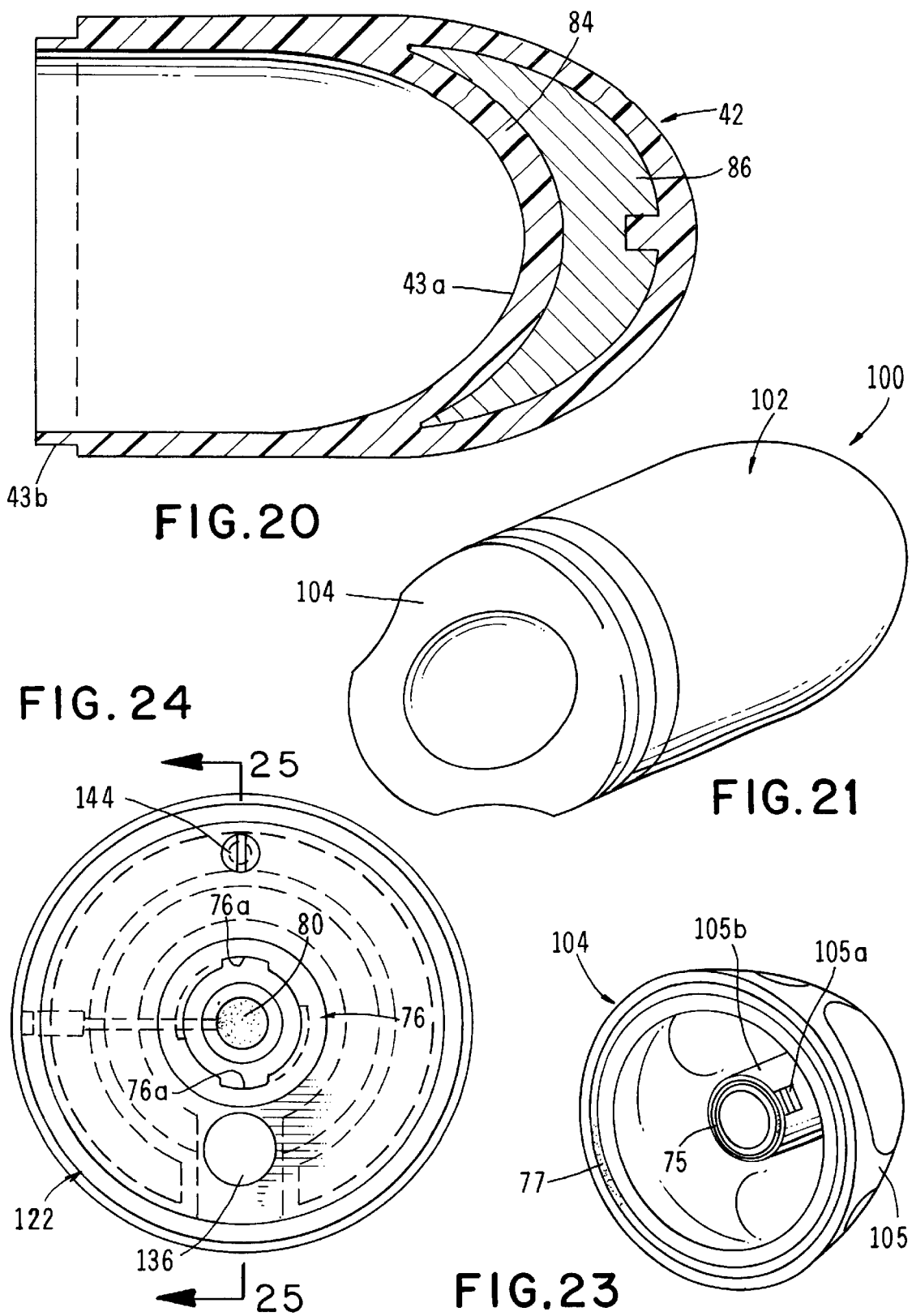

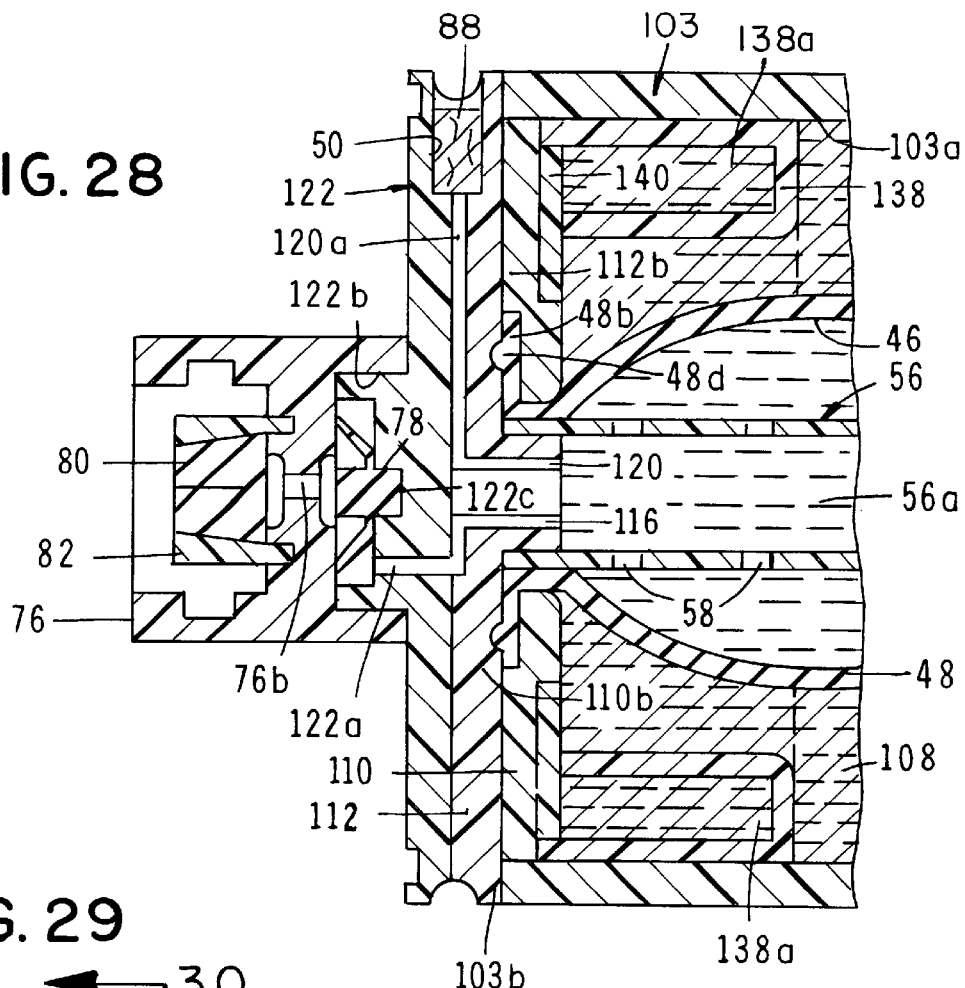
FIG. 28
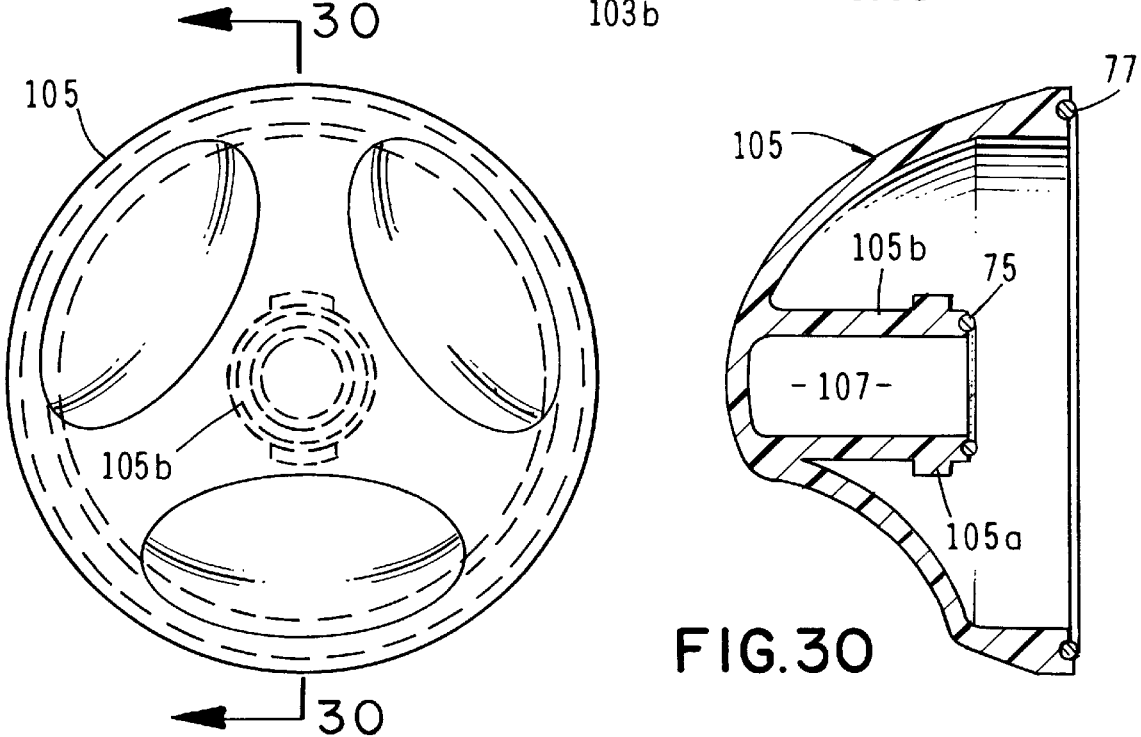
FIG. 29
FIG. 30

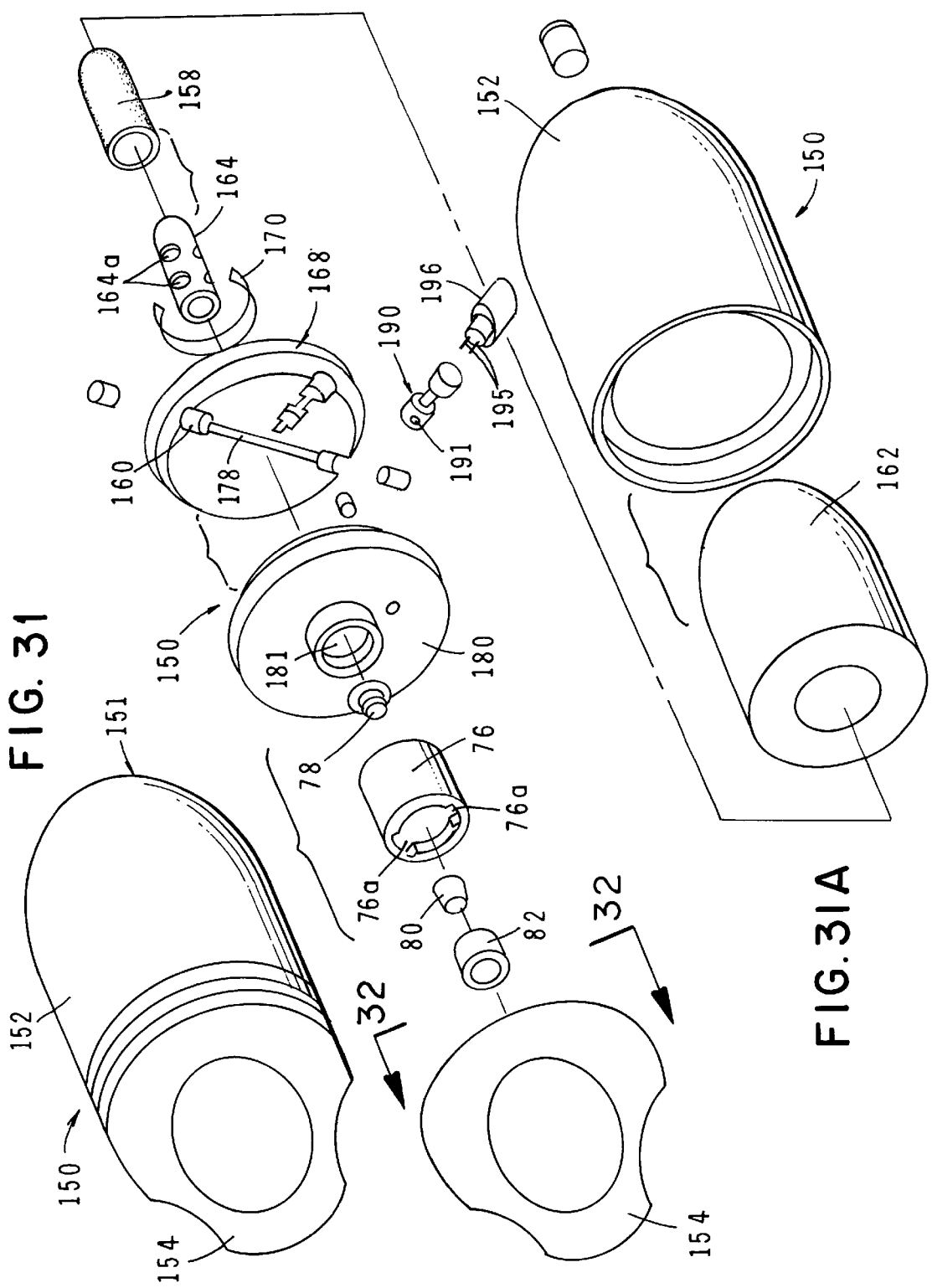

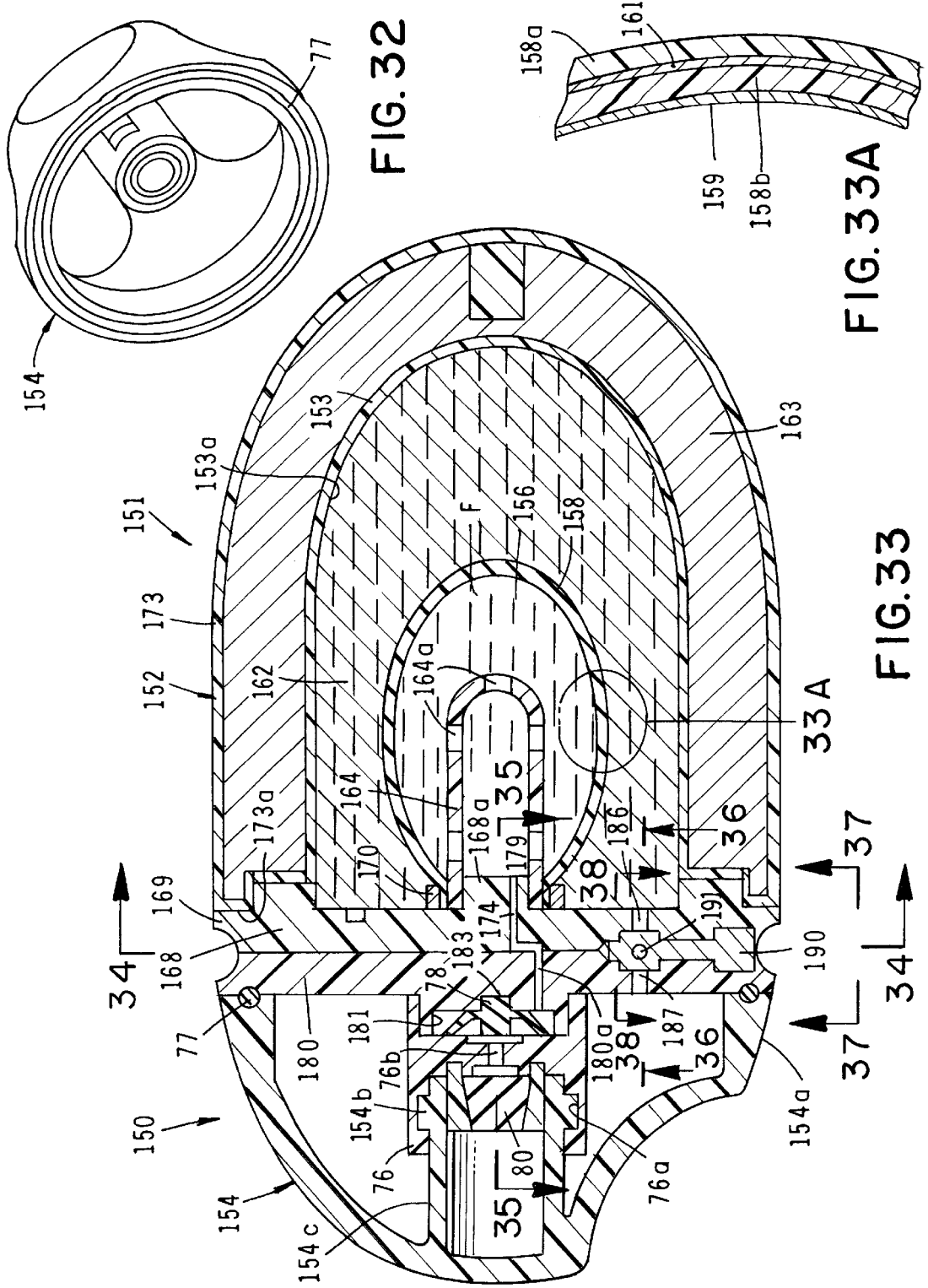

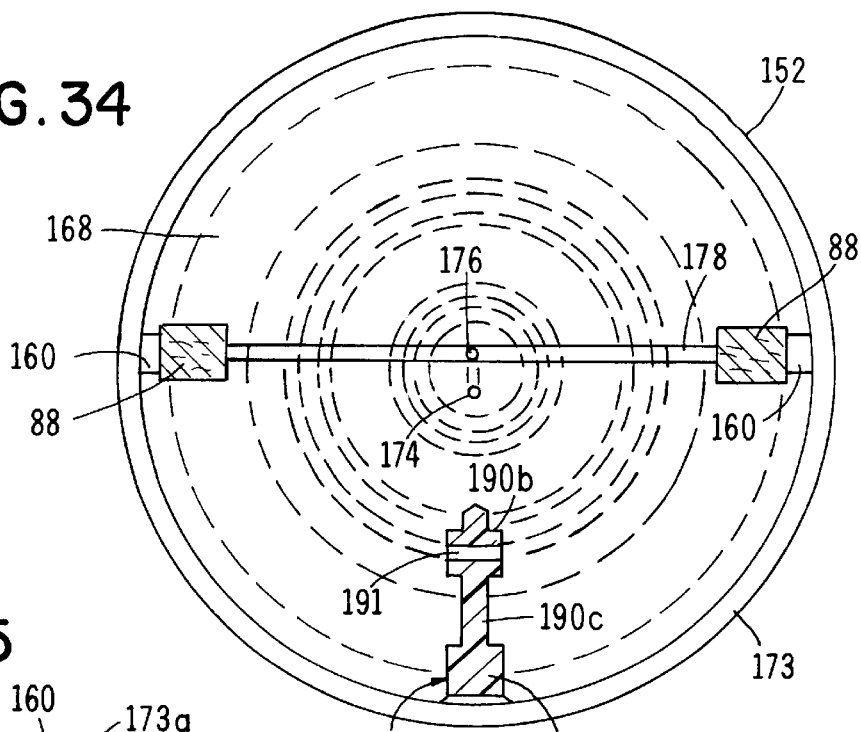
FIG. 34
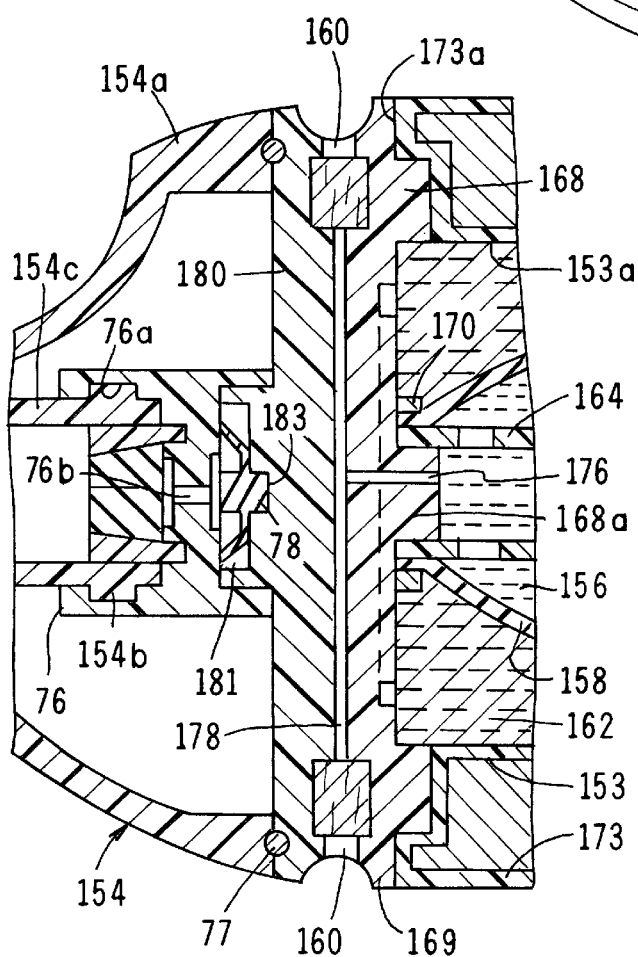
FIG. 35
FIG. 36

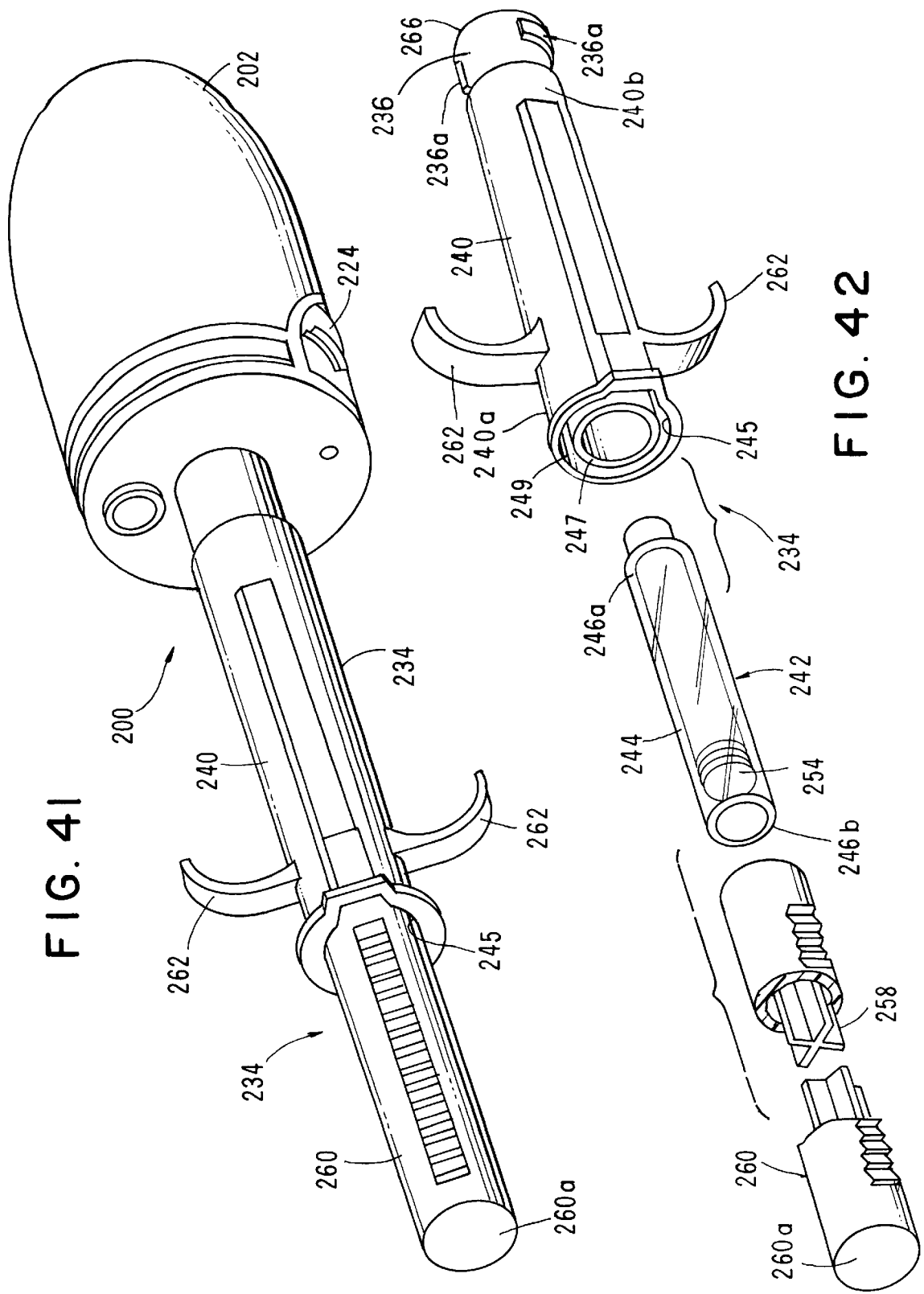

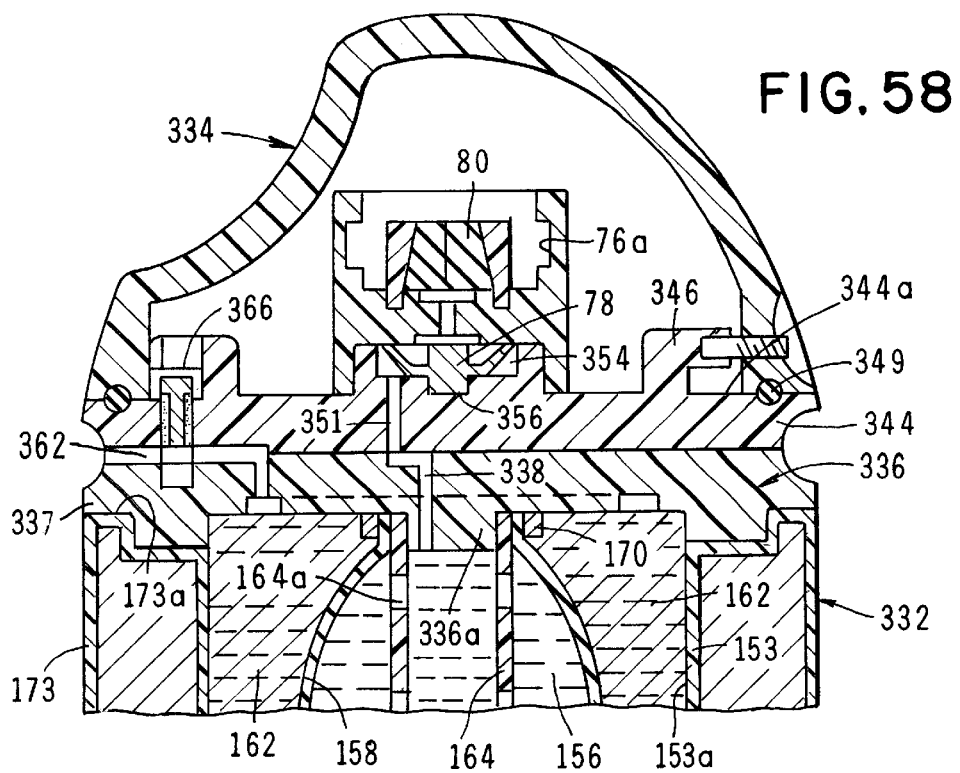
FIG. 58
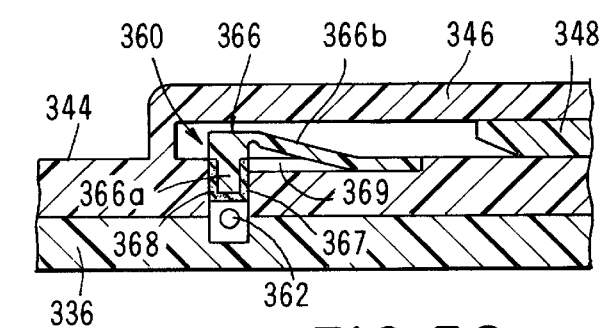
FIG. 59
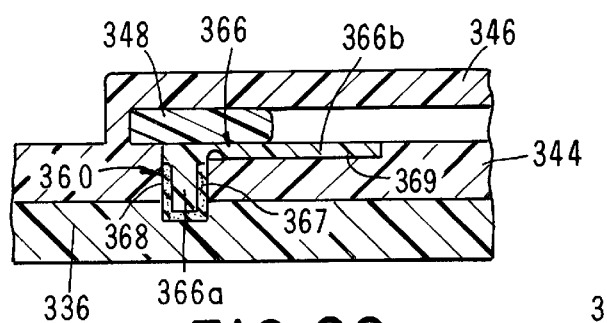
FIG. 60
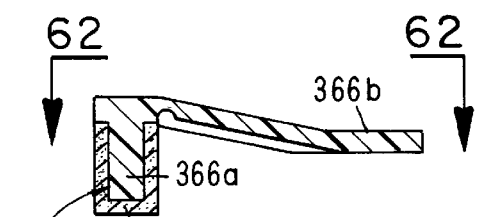
FIG. 61
FIG. 62

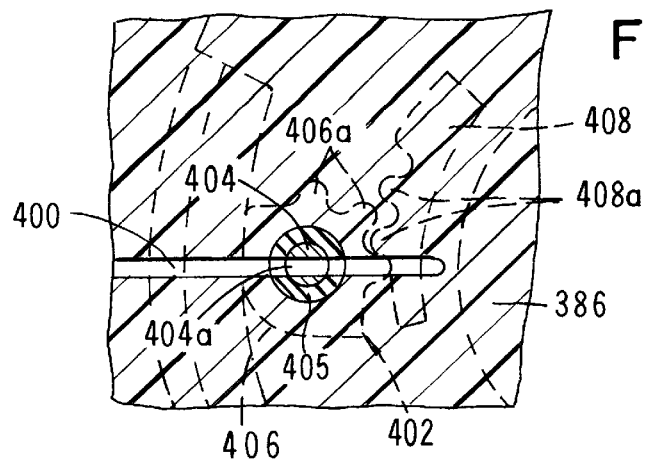
FIG. 65
FIG. 66
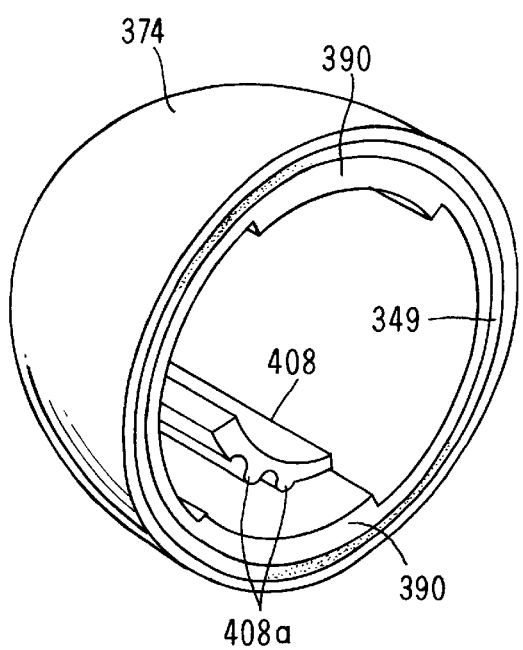
FIG. 68
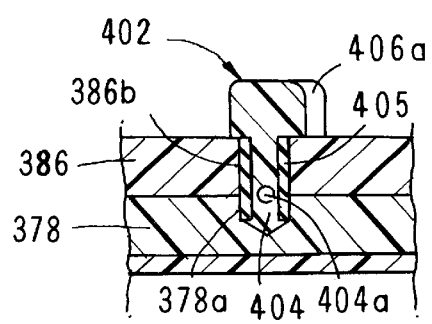
FIG. 67
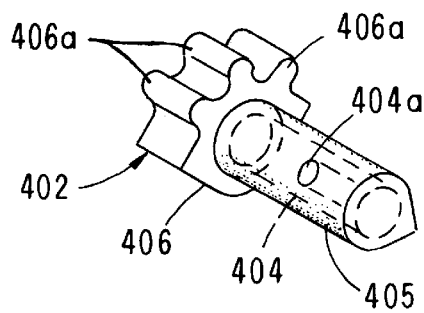
FIG. 69

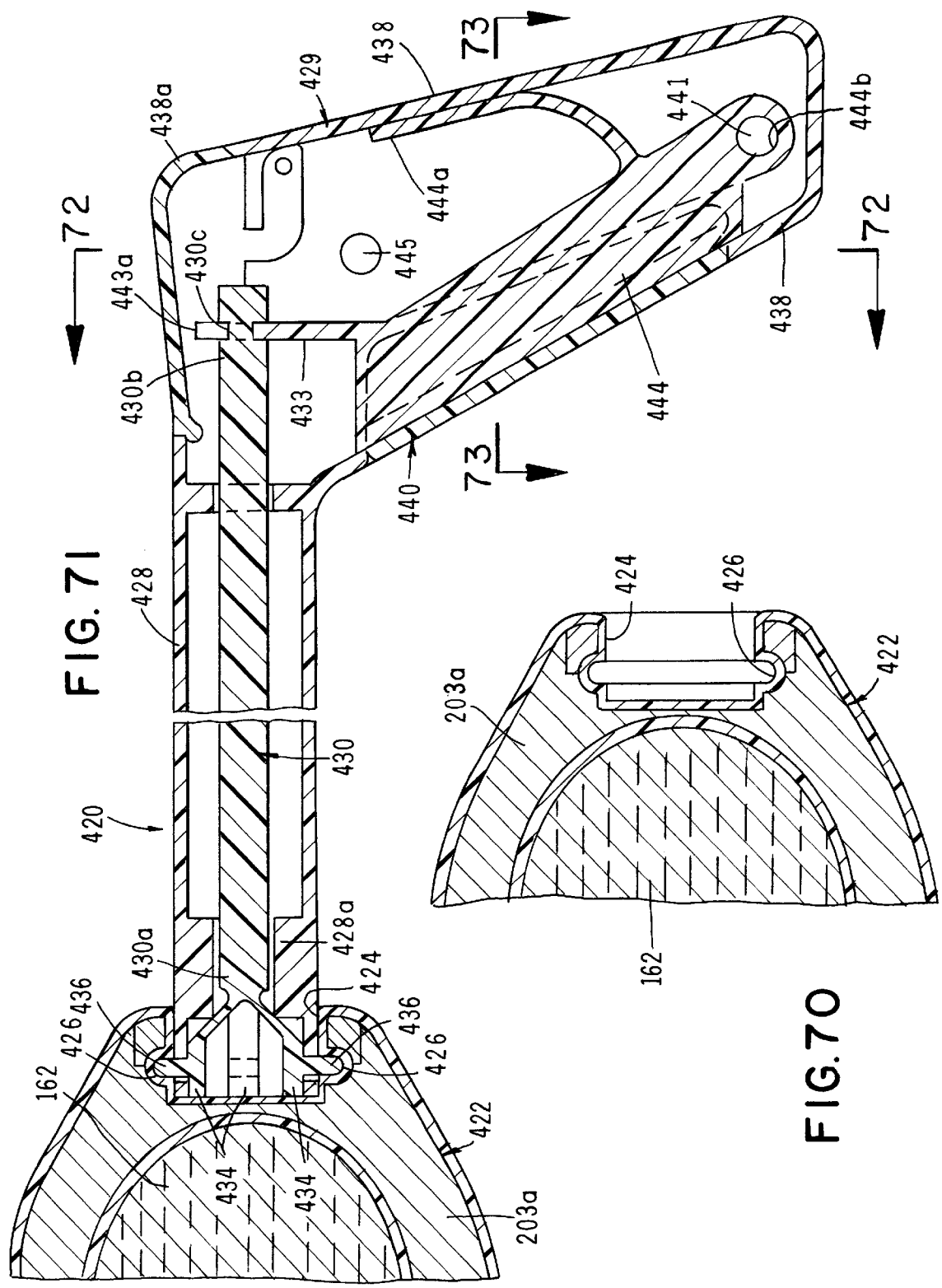

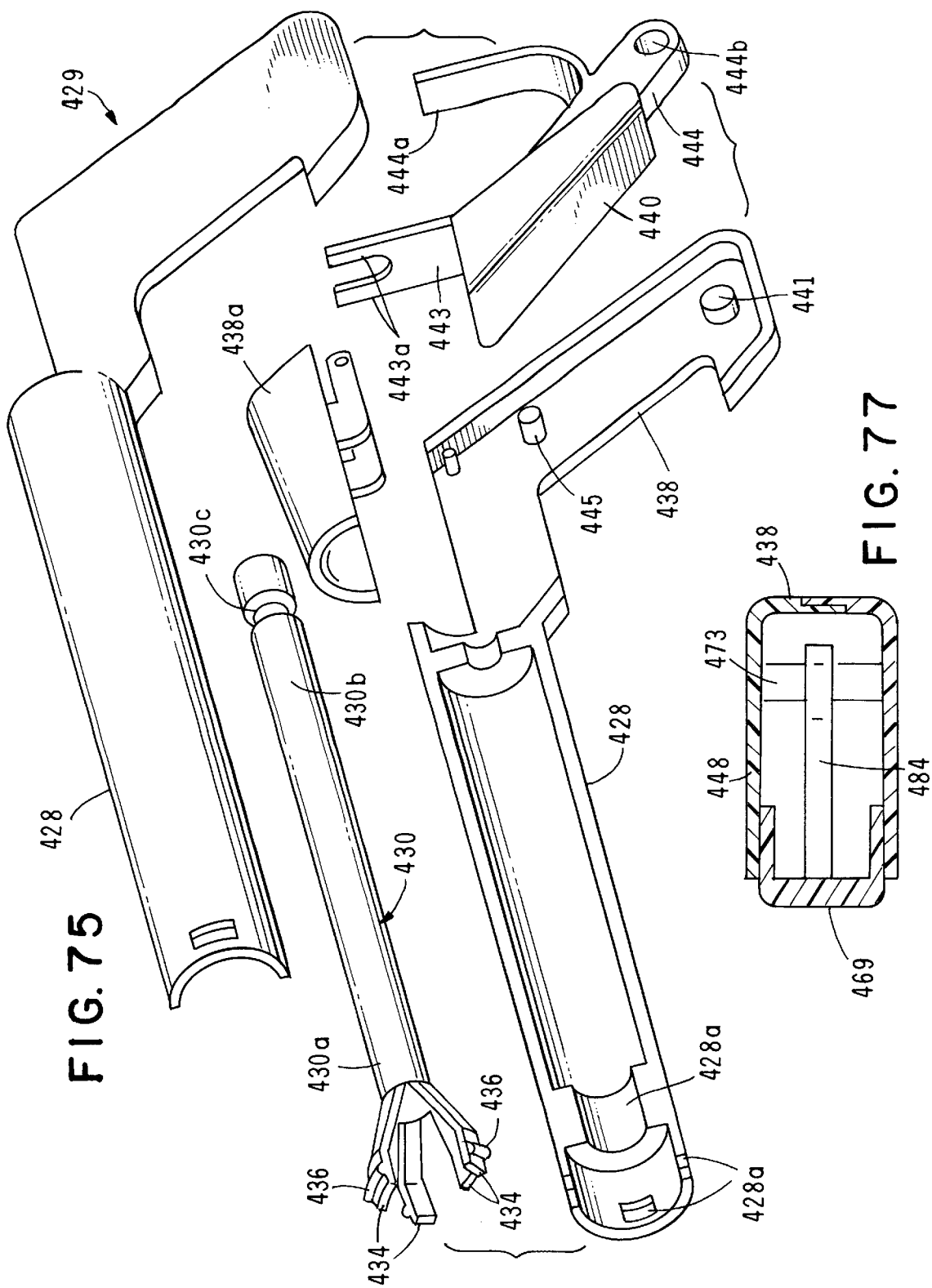

FLUID DELIVERY DEVICE WITH TEMPERATURE CONTROLLED ENERGY SOURCE

BACKGROUND OF THE INVENTION

This is Continuation-in-Part of application Ser. No. 08/919,147, filed Aug. 27, 1997 U.S. Pat. No. 5,961,492.

FIELD OF THE INVENTION

The present invention relates generally to fluid delivery devices. More particularly, the invention concerns a device for the delivery of beneficial agents to ruminants.

DESCRIPTION OF THE PRIOR ART

It has long been recognized that the delivery of various types of nutrients, drugs, dietary supplements and trace elements for grazing animals, such as sheep and cattle is highly beneficial to the well being and growth of the animal. By way of example, delivery to the grazing animal of various types of antiparasitics can be used to control mange mites, sucking lice, cattle grubs, fly larva, ticks and the like. Similarly, delivery of anti-bacterials such as sulphonamides has proven effective for disease control. In like manner, the delivery of monesin sodium as an anti-bacterial agent has proven effective as a growth promotion in cattle and sheep and the delivery of S-methoprene has been shown to be effective to control pupa of the horn fly in the manure pat.

Commonly, grazing animals such as cattle and sheep are turned out in the spring to spend much of the spring, summer and autumn season grazing the open range. With such animals the periodic administration of drugs is complicated by the need to retrieve the animal and then, after retrieval, to effectively administer the nutrient or drug to the animal. For example, one of the principal problems involved in the control of livestock pests has not been the unavailability of effective toxicans, instead it is the relatively short duration of effectiveness of the available compounds due to photodecomposition, evaporation, and absorption of the materials, and due to mechanical losses caused by rubbing of the animal, muscular contractions and the like. Additionally, repeated treatment of livestock is expensive in terms of both labor and insecticides. To compensate for the rapid degradation of the pesticides on animals, the producer must apply larger quantities than are necessary for control of the immediate population if toxic levels are to be maintained for any length of time. Such a practice is wasteful of insecticides, results in greater contamination to the environment and increases the probability of toxicity to animals and the residues in animal products.

In light of the foregoing, for many years, it has been an objective of the industry to develop techniques that would make it possible to maintain the minimum effective level of toxicans in livestock over an extended period and thereby increase the efficiency and safety of livestock pest control. Additionally, the cumbersome and labor intensive process of introducing any drug, medicament or other substance into the daily food supply, which is ingested orally by the ruminant, provides little or no assurance that the required amount of agent will have been administered as food intake will vary with each feeding. The use of a controlled-release drug delivery device is an attractive alternative because such an approach has the significant advantage of providing the animal with nutrients and medicaments, which will be released in a controlled manner into the body over a period of time.

It is known that the rumen is a suitable site for the administration of drugs to a ruminant. The drug formulation can be injected directly into the rumen through the flank of the animal. Alternatively, a controlled release drug delivery device can be introduced via the mouth of the animal in which case it is desirable for the device to be retained within the reticulo-rumen for controlled release of the drug formulation thereafter. One method of retaining the device within the rumen is to arrange for its geometry to alter once it is in the rumen. For example, wings extended laterally from the main body of the device can retard or prevent regurgitation thereof by the animal. Alternatively, the device may be made sufficiently dense for it to be retained in the rumen simply by the force of gravity. For example, prior art experimentation has shown that retention in the rumen can be achieved by providing a device having an overall device density greater than 2.0.

The prior art drug delivery devices for use in rumens typically fall into the classes of erodible devices, reservoir devices, osmotic devices, and pulsatile devices. Erodible devices are designed to dissolve or abraid as a result of solutions within the rumen or due to mechanical action of the rumen. Exemplary of one prior art erodible system is that described in U.S. Pat. No. 3,056,724 issued to H. R. Marsten. Marsten discloses an erodible bolus, which is, provided in the form of a pellet containing cobalt oxide and other diluents that function to produce a product that releases cobalt to the animal for the full grazing season. Another example of a prior art erodible bolus is that described in U.S. Pat. No. 4,166,107 issued to Miller et al. Miller et al discloses a sustained release bolus containing compositions of insect regulators to control the larval activity of arthropods in the manure of livestock.

Exemplary of a prior art reservoir type device is the device described in U.S. Pat. No. 4,959,218 issued to Eckenhoff et al. This patent describes a delivery device comprising a housing having an internal space, a beneficial agent in the space, expandable means in the space for causing the beneficial agent to be delivered from the device and means in the space for shielding the beneficial agent from fluid. An earlier Eckenhoff et al U.S. Pat. No. 4,595,583 discloses a somewhat similar reservoir device comprising a semipermeable housing defining an internal space, a dense member in the space, a heat responsive composition containing a beneficial agent in the space, an expandable member in the space, and a passageway in the semipermeable housing for delivering the beneficial agent from the dispensing device. The heat-responsive composition comprises a heat sensitive, hydrophilic or hydrophobic material that exhibits solid-ike properties at room temperature and exhibits a melting point that approximates mammalian body temperatures of 37 degrees centigrade. When administered to the ruminant, this heat responsive composition, which contains the beneficial agent, is heated by the animal's body and becomes liquid through phase change, thus allowing it to flow outward of the device.

The prior art osmotic devices take several forms. One such device is described in U.S. Pat. No. 3,845,770 issued to Theeuwes et al. This device comprises a wall surrounding and forming a compartment for containing a useful composition of matter and has a passageway for dispensing the composition. The wall is comprised, in at least a part, of a material permeable to an external fluid. The composition is soluble in the fluid and exhibits an osmotic pressure gradient against the fluid or the composition has limited solubility and is admixed with an osmotically effective compound soluble in the fluid that exhibits an osmotic pressure gradient against the fluid. In operation, the composition is dispensed from the device by fluid permeating into the compartment producing a solution of the soluble composition or a solution of the osmotically effective compound containing the composition, which solution in either operation is released through the passageway to the exterior of the device at a rate controlled by the permeability of the wall and the osmotic pressure gradient across the wall of the device.

Pulsatile systems consist of systems which release multiple doses at preprogrammed intervals. The advantages of these systems are that they tend to better mimic prior art methods of administering multiple doses of immediate release products given at specific time intervals. Exemplary of one form of prior art pulsatile system is that described in U.S. Pat. No. 4,381,780 issued to Holloway. Holloway describes a system consisting of a series of degradable partitions that form compartments within a body. The partitions are made from cellulosic materials that degrade in the rumen thus releasing the drug successively from the compartments. The drug dosage is controlled via the composition or each drug compartment and by the thickness and composition of the degradable partitions.

The principal drawbacks of the prior art delivery devices for use in ruminants include difficulty of use, lack of reliability overtime and the inability to deliver precisely controlled doses over extended periods of time. Additionally, unlike devices of the present invention, the prior art devices cannot be filled in the field. It is these drawbacks that the present invention seeks to overcome by providing an easy to use and highly reliable device for precisely delivering various beneficial agents over long periods of time. The devices of the present invention uniquely embody a novel, thermal expanding polymer material, such as a heat expandable gel, that acts as an internal stored energy source for delivering the beneficial agents contained within the device to the animal at a precisely controlled rate over time. This unique stored energy source is more completely described in copending U.S. Ser. No. 08/919,147, which application is hereby incorporated by reference as though fully set forth herein.

SUMMARY OF THE INVENTION

It is an object of the present invention to provide a technically advanced delivery apparatus for the administration of nutrients, drugs, vitamins, trace elements and the like (hereinafter beneficial agents) to a ruminant. More particularly, it is an object of the invention to provide a self-contained dispensing apparatus of such a character that embodies a novel, thermal expanding polymer material which uniquely functions as an internal energy source for controllably expelling the beneficial agents from the device.

Another object of the invention is to provide a delivery apparatus of the character described which can conveniently be used for precise infusion of beneficial agents to ruminants such as cattle and sheep over extended periods of time of up to 200 days.

Another object of the invention is to provide a novel dispensing device that can administer a predetermined regimen for a particular time period and one which requires intervention only for initiation of the regimen.

Another object of the invention is to provide an improved self-contained dispensing device which will permit high concentration of active agents to be contained therein which agents will not exhibit a tendency to have their potency decreased by a chemical breakdown.

Another object of the invention is to provide a novel delivery apparatus of the character described in the preceding paragraphs which can be effectively used to administer to ruminants beneficial agents including anti-parasitics, antibacterials, growth hormones anthelmintics and a variety of trace elements such as cobalt.

Another object of the invention is to provide a novel delivery apparatus of the class described which is of a size that can be introduced into the ruminant via the esophagus and is of a density such that the device will be retained within the reticulo-rumen for controlled release of the beneficial agents over long periods of time.

Another object of the invention is to provide an apparatus of the character described in the preceding paragraphs which embodies as its stored energy source a gel, which is a soft, pliable, semi-solid, heat expandable mass that is heated by the ruminant's body temperature in a manner to controllably expel fluids from the device over substantial periods of time.

Another object of the invention is to provide an apparatus as described in which the heat-expandable mass is specifically tailored to provide precise, predictable, protocol delivery of the beneficial agents stored within the reservoir of the device.

Another object of the invention is to provide an apparatus of the class described which is durable, highly reliable in use and one that will not be damaged by muscular contractions or rubbing by the animal.

Another object of the invention is to provide a delivery apparatus of the character described which, due to its unique construction, can be manufactured inexpensively in large volume by automated machinery.

Another object of the invention is to provide a dispensing apparatus for dispensing to the animal a modified delivery device. More particularly, it is an object of the invention to provide a novel dispensing apparatus that enables the expeditious insertion of the delivery device into the throat of the animal until the modified delivery device is disposed behind the back of the tongue or even deeper into the animal's throat.

Another object of the invention is to provide a dispensing apparatus of the character described in the preceding paragraph which is of a simple design, is easy to use and is extremely durable and reliable in operation.

Another object of the invention is to provide a dispensing apparatus of the character described in the preceding paragraph which can be filled with a selected beneficial agent in the field prior to dispensing to the animal.

Another object of the invention is to provide a dispensing apparatus of the character described in the preceding paragraph which can be filled in a sterile manner with a selected beneficial agent. More specifically, the dispensing apparatus may be filled by means of a novel filling device that enables the convenient handling of the beneficial agent in discrete vials prior to the filling step.

BRIEF DESCRIPTION OF THE DRAWINGS

FIG. 4 is a generally perspective, exploded view of the delivery device shown in FIG. 3.

FIG. 5 is a generally perspective rear view of the forward portion of the delivery device as viewed along lines 5—5 of FIG. 4.

FIG. 20 is a side-elevational, cross-sectional view of the housing component of the device of the invention.

FIG. 21 generally perspective view of an alternate form of the delivery device of the invention for the delivery of beneficial agents to ruminants.

FIG. 23 is a generally perspective rear view of the forward portion of the delivery device as viewed along lines 23—23 of FIG. 22.

FIG. 24 is a front view of the base assembly of the embodiment shown in FIG. 21.

FIG. 28 is a cross-sectional view taken along lines 28—28 of FIG. 25.

FIG. 29 is a front view of the cover assembly of the device.

FIG. 30 is a cross-sectional view taken along lines 30—30 of FIG. 29.

FIG. 31 is a generally perspective view of still another form of the invention.

FIG. 31A is a generally perspective exploded view of the device shown in FIG. 31.

FIG. 32 is a generally perspective rear view of the forward cover portion of the delivery device as viewed along lines 32—32 of FIG. 31

FIG. 33 is an enlarged, cross-sectional view of the device illustrated in FIG. 31.

FIG. 33A is a greatly enlarged, cross-sectional view of the area designated in FIG. 33 as 33A.

FIG. 34 is a cross-sectional view taken along lines 34—34 of FIG. 33.

FIG. 35 is a cross-sectional view taken along lines 35—35 of FIG. 33.

FIG. 36 is an enlarged, cross-sectional view taken along lines 36—36 of FIG. 33.

FIG. 41 is a cross-sectional, fragmentary view of yet another embodiment of the invention having a somewhat different type of vent control means.

FIG. 42 is a fragmentary front elevational view of the device shown in FIG. 41.

FIG. 53 is a generally perspective view of one of the vials of the assembly shown in FIG. 52 partly broken away to show internal construction.

FIG. 58 is a cross-sectional view taken along lines 58—58 of FIG. 57.

FIG. 59 is a cross-sectional view taken along lines 59—59 of FIG. 57.

FIG. 60 is a cross-sectional view similar to FIG. 59 but showing the position of the components of the device after the cover assembly has been rotatably coupled with the base assembly.

FIG. 61 is a cross-sectional view of the vent control member of this latest form of the invention FIG. 62 is a view taken along lines 62—62 of FIG. 61.

FIG. 65 is a cross-sectional view taken along lines 65—65 of FIG. 63.

FIG. 66 is a cross-sectional view similar to FIG. 65, but showing the vent closure means rotated to a vent closed position.

FIG. 67 is a cross-sectional view taken along lines 67—67 of FIG. 63.

FIG. 68 is a generally perspective, bottom view of the cover subassembly of this latest embodiment of the invention.

FIG. 69 is a generally perspective view of the vent closure control member of the invention.

FIG. 70 is a fragmentary, side-elevational, cross-sectional view of a portion of the delivery device of the invention that is specially adapted for use with dispensing apparatus for use in administering the delivery device to the animal.

FIG. 71 is a fragmentary, side-elevational, cross-sectional view showing the modified delivery device of FIG. 70 interconnected with a hand-operated dispensing apparatus.

FIG. 75 is a generally perspective, exploded view of the dispensing apparatus shown in FIG. 74.

FIG. 77 is a cross-sectional view taken along lines 77—77 of FIG. 76.

DESCRIPTION OF THE INVENTION

Figure 1:
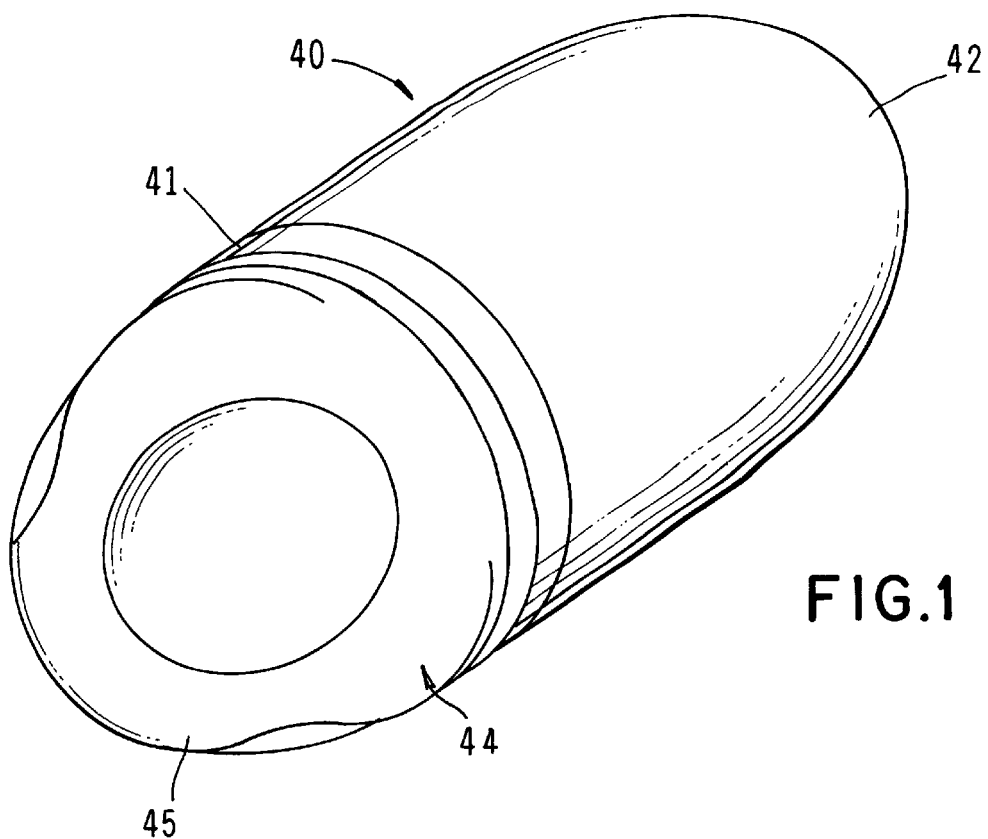
FIG. 1 is a generally perspective view of one form of the delivery device of the invention for the delivery of beneficial agents to ruminants.
Figure 2:
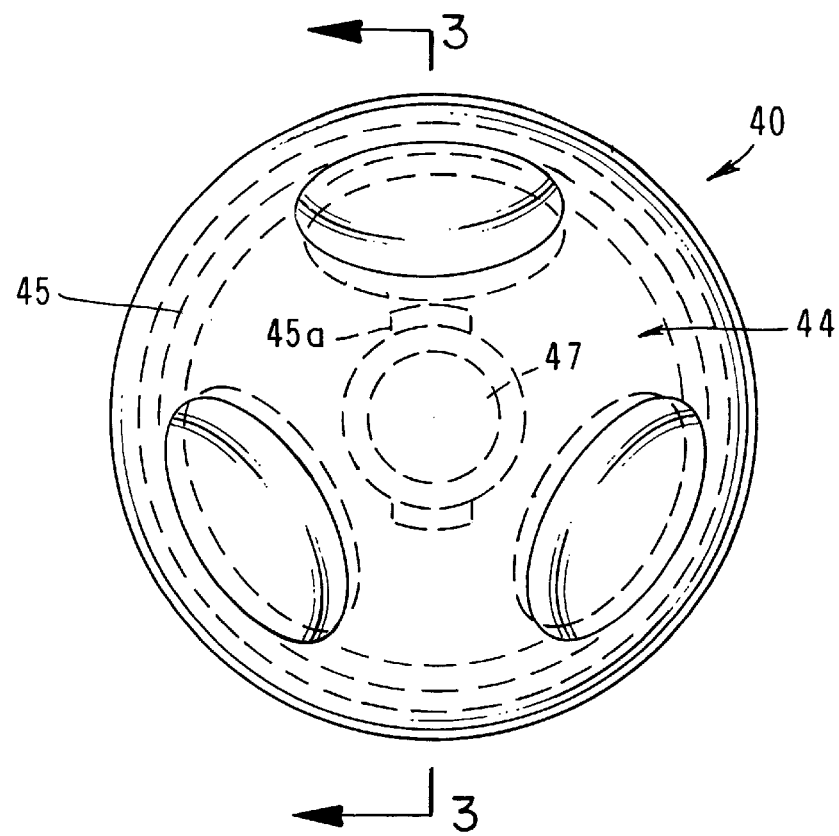
FIG. 2 is an enlarged front-elevational view of the fluid delivery device shown in FIG. 1.

Referring to the drawings and particularly to FIGS. 1 through 4, one form of the apparatus of the invention for use in administering beneficial agents to a ruminant is there shown and generally designated by the numeral 40. As best seen by referring to FIGS. 1 and 3, this embodiment of the invention comprises a generally egg-shaped housing 41 which includes a base assembly 42 and a cover assembly 44. The device has the novel shape illustrated in FIG. 1 to enable it to be conveniently introduced into the rumen through the mouth of the ruminant.

Figure 3:
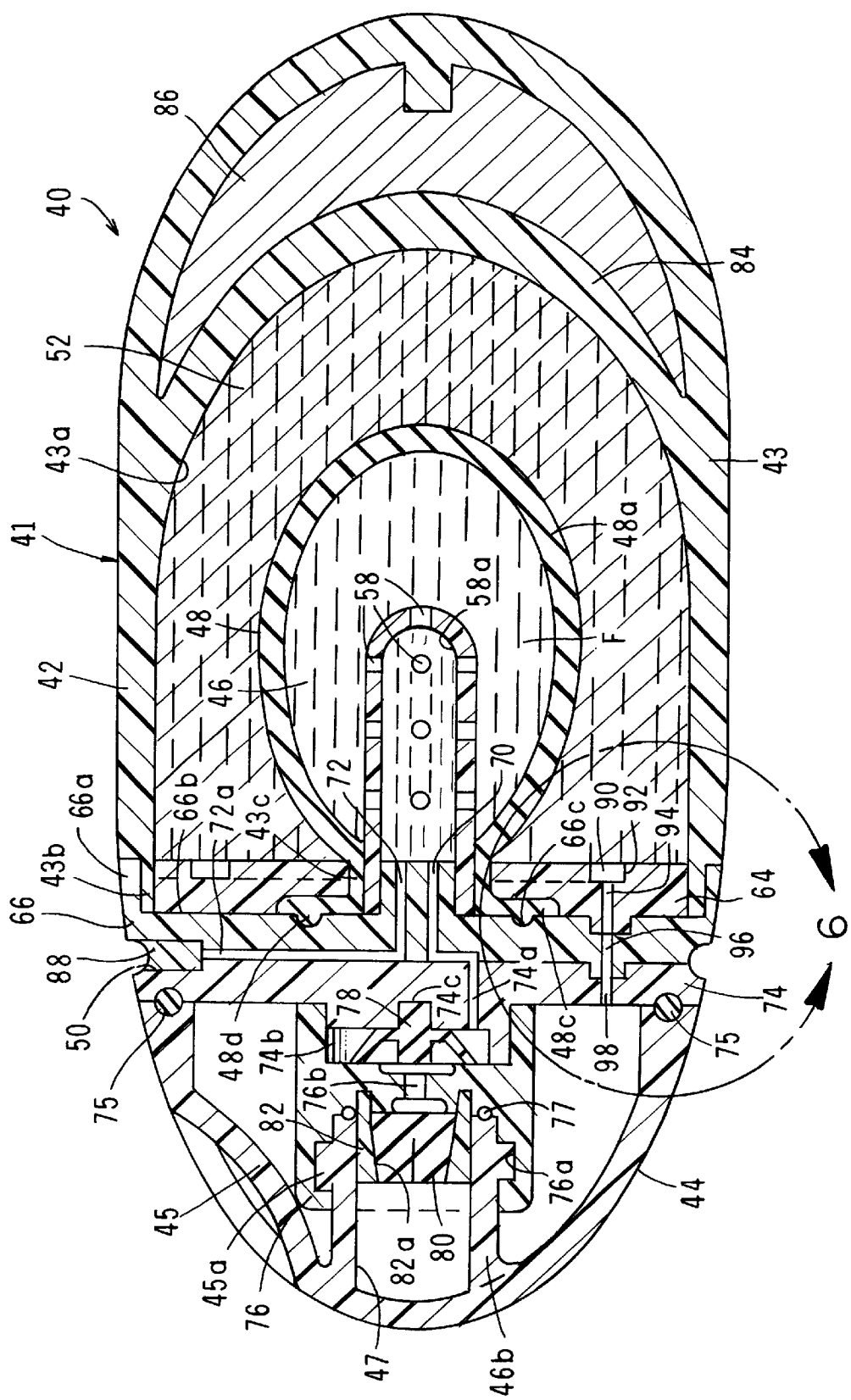
FIG. 3 is a cross-sectional view taken along lines 3—3 of FIG. 2.

Formed within an internal chamber 43a of a base component 43 of base assembly 42, is a fluid reservoir 46 for containing the beneficial agent to be delivered to the ruminant (FIG. 3). Fluid reservoir 46 is formed by an elastomeric distendable member 48 which, in a manner presently to be described, is distended into the configuration shown in FIG. 3, by the introduction of the beneficial agent into the device via the fill means of the invention.

Comprising an extremely important aspect of the apparatus of the present invention is a heat-expandable means, which is carried within internal chamber 43a. The heat expandable means functions to controllably urge fluids contained within reservoir 46 to flow outwardly into the rumen of the ruminant through the delivery means of the invention which includes an outlet 50 formed in housing 41. The heat-expandable means is here provided in the form of a thermal expandable polymer mass 52 which is contained within chamber 43a in the manner best seen in FIG. 3. Expandable mass 52 can take several forms, but a particularly attractive form for devices of the present invention comprises a semisolid form such as a gel. Unlike a liquid, which can offer no permanent resistance to change in shape and must be constrained within some type of container, expandable mass 52 is of a semisolid form which can advantageously be handled without external containment under ambient manufacturing conditions.

From a technical viewpoint, gels are often characterized as soft solids, which reside in a state between a liquid and a solid state. Frequently gels comprise a cross-linked network of long polymer molecules with liquid molecules trapped within the network. Many gels known in the prior art not only are capable of significantly large volume change in response to stimulus (phase-transition gels), but also exhibit physical characteristics that enable them to closely conform to the shape of an adjacent member such as a distendable membrane. Such gels are ideally suited as a stored energy means for fluid delivery devices of the character described hereinafter and also of the character described in incorporated-by-reference application Ser. No. 09/919,147.

Phase transition gels best suited for use in constructing the heat expandable means of the present invention are gels which exhibit a large volume change at a given phase-transition condition. Unlike liquids, which exhibit a fixed temperature for state of vaporization to a known volume and with such vaporization point changing as a function of ambient pressure, the phase-transition gels in this invention are multicomponent polymers which can be made to respond with various volume changes to a singular external temperature stimuli. Advantageously, the difference in volume between the expanded phase of these phase-transitions gels and the contracted phase thereof can be orders of magnitude. Examples of suitable phase-transition gels are disclosed in Tanka et al, U.S. Pat. Nos. 4,732,930; Re-35068 and 5,403,893, and Schiller et al, WO 96/02276.

Turning particularly to FIG. 3, it is to be noted that a generally cylindrically shaped fill tube 56 having inlet and outlet ports 58 extends into chamber 43a. Fill tube 56 cooperates with elastomeric member 48 to form reservoir 46 when, as previously mentioned, the beneficial agent is introduced into the fill tube 56 by the novel fill means of the invention. With the construction shown in FIG. 3, when the heat expandable mass 52 is heated by the body heat of the ruminant, it will expand pand and act upon distendable member 48 in a manner to tend to return the member toward its starting configuration and to controllably force the fluid "F", which is contained within the reservoir 46, outwardly of the device, through the delivery means, and into the rumen of the animal. It is to be noted that as member 48 moves toward its starting configuration (see FIGS. 4 and 16), it will closely conform to the shape of the fill tube 56 as the heat expandable mass 52 expands thereby causing a complete and controlled expelling of fluid from reservoir 46 through the fluid outlets of the fill tube 56 and then into the delivery means of the apparatus, the details of construction of which will presently be described.

Figure 13:
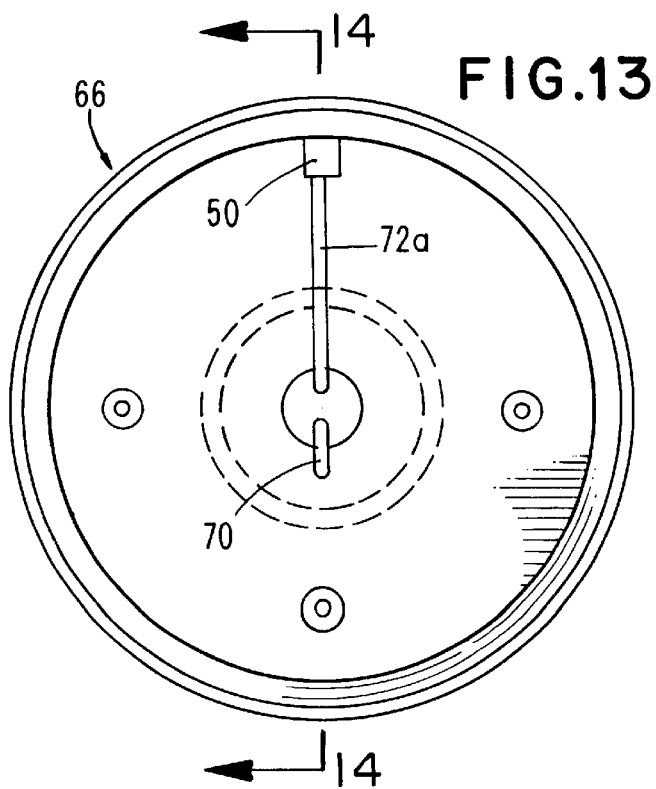
FIG. 13 is a front view of the other of the manifold components of the device.
Figure 16:
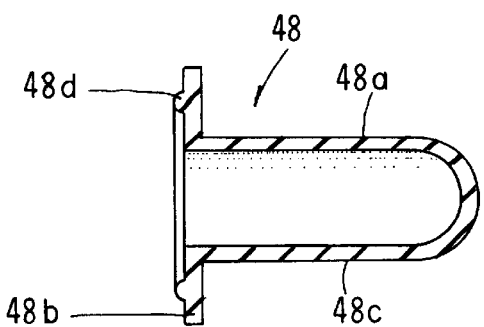
FIG. 16 is a cross-sectional view taken along lines 16—16 of FIG. 15.
Figure 17:
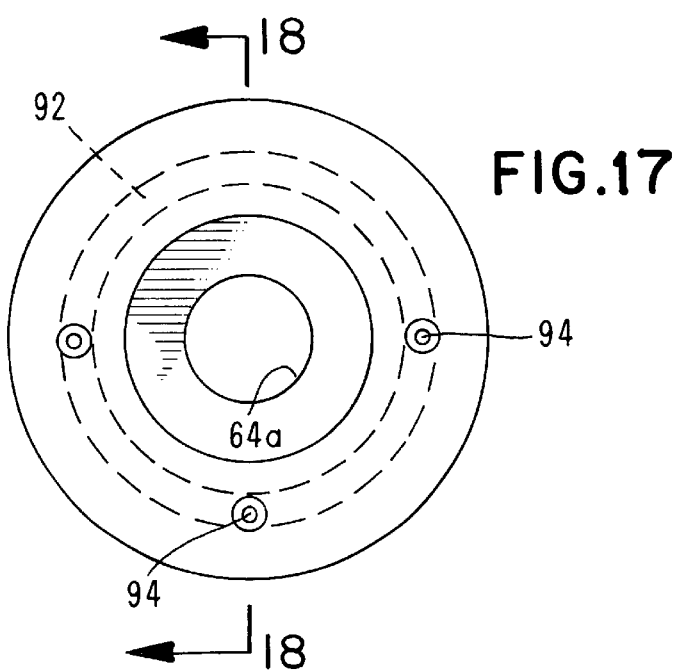
FIG. 17 is a front view of the reservoir retaining ring of the device.
Figure 18:
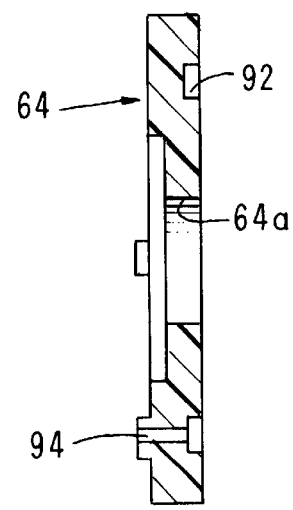
FIG. 18 is a cross-sectional view taken along lines 18—18 of FIG. 17.
Figure 19:
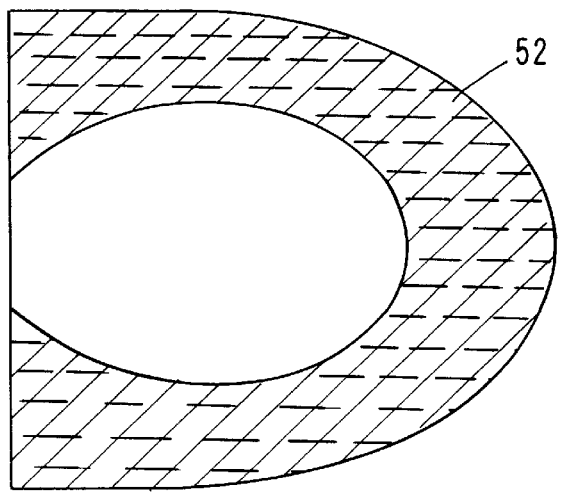
FIG. 19 is a side-elevational, cross-sectional view of the thermal expanding component of the device.

Referring particularly to FIGS. 3, 4, and 16 elastomeric member 48 includes a body portion 48a, a flange portion 48b and a neck portion 48c. As shown in the drawings, a flange portion 48b includes a circumferentially extending sealing protuberance 48d. Member 48 is held in position within chamber 43a by means of a retaining ring 64 which is received within the open end of base member 43 in the manner best seen in FIG. 3. As best seen in FIGS. 4, 17 and 18 retaining ring 64 includes a central opening 64a which closely receives the neck portion 48c of elastomeric member 48 and functions to maintain the neck portion in sealing engagement with the outer wall of fill tube 56 (FIG. 3). Fill tube 56 is, in turn, held in position within chamber 43a by a first manifold component 66 which is disposed between base 43 and a cover 45 that comprises a part of cover assembly 44. Manifold component 66 includes a skirt-like portion 66a which is closely received over a reduced diameter flange 43b of base 43 (see also FIGS. 13 and 14).

Figure 8:
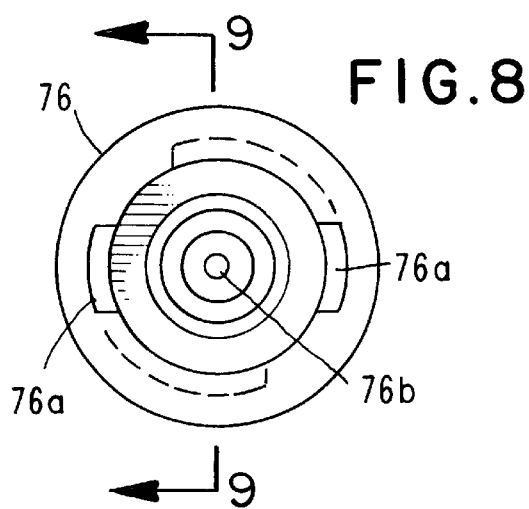
FIG. 8 is a front view of the septum housing component of the device.
Figure 9:
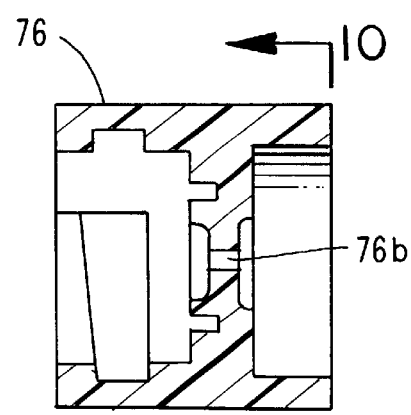
FIG. 9 is a cross-sectional view taken along lines 9—9 of FIG. 8.
Figure 10:
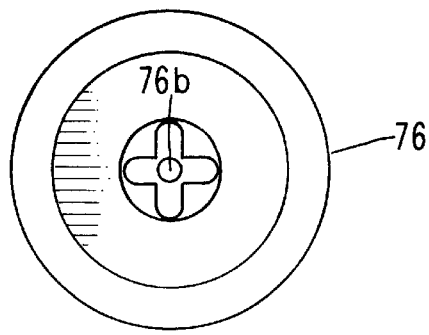
FIG. 10 is a view taken along lines 10—10 of FIG. 9.
Figure 11:
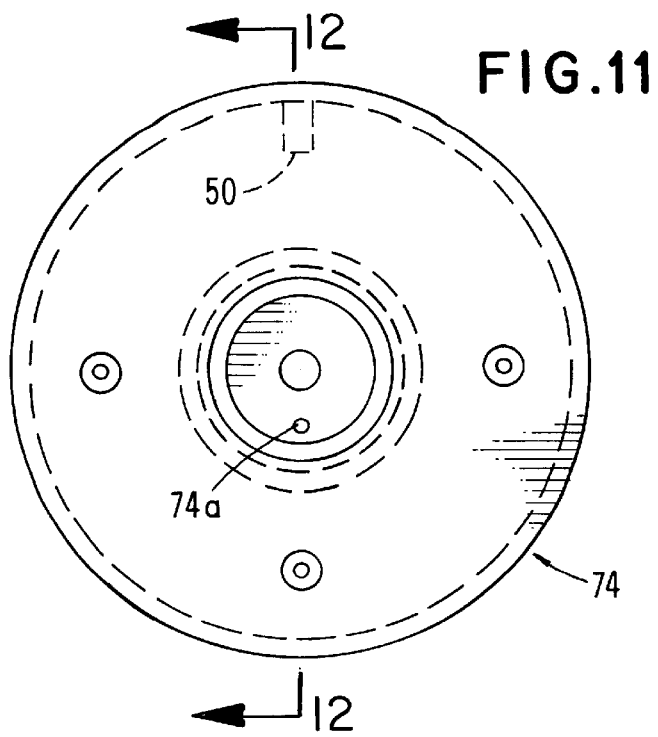
FIG. 11 is a front view of one of the manifold components of the device.
Figure 12:
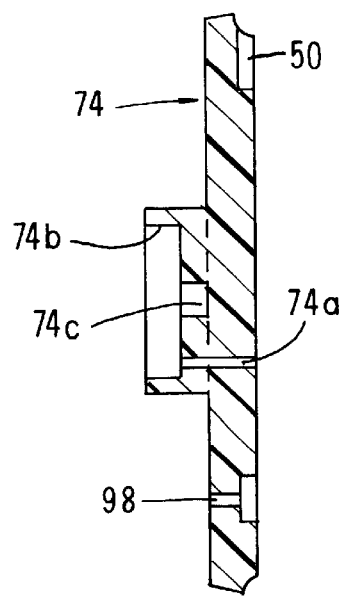
FIG. 12 is a cross-sectional view taken along lines 12—12 of FIG. 11.
Figure 14:
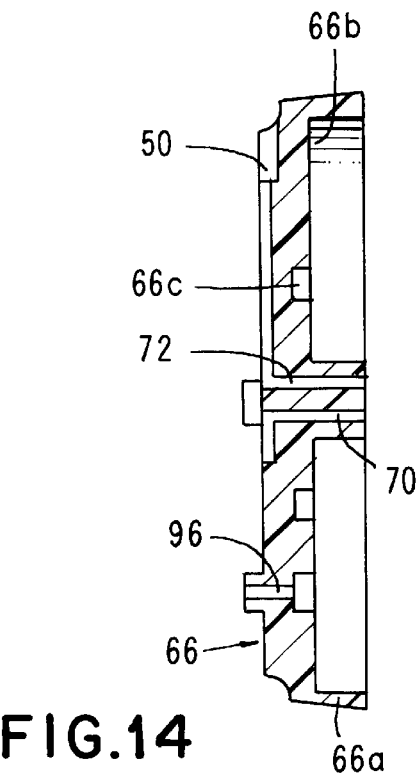
FIG. 14 is a cross-sectional view taken along lines 14—14 of FIG. 13.
Figure 15:
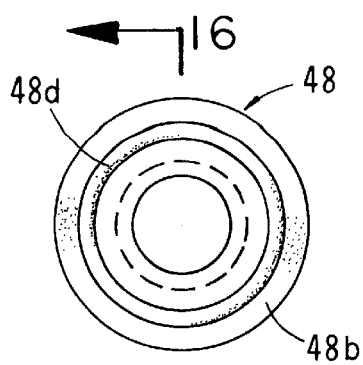
FIG. 15 is a front view of the elastomeric reservoir defining member of the device.

When the manifold component 66 is disposed in engagement with base 43, in the manner shown in FIG. 3, flange portion 48b of distendable member 48 is securely clamped between the inner face 66b of manifold component 66 and the outer face of retaining ring 64 with protuberance 48d being maintained in sealable engagement within a circumferentially extending groove 66c formed in manifold component 66. As indicated in FIGS. 3 and 14, manifold component 66 is provided with a fill passageway 70 which is in communication with the interior of fill tube 56 and is also provided with a delivery passageway 72 that is also in communication with the interior of fill tube 56. Disposed in engagement with manifold 66 is a second manifold 74 which is interconnected with cover 45 by a connector means shown here as a connector component 76. More specifically, connector component 76, which is connected to manifold 74, includes a pair of circumferentially spaced slots 76a (see also FIGS. 8 and 9) which lockably receive a pair of circumferentially spaced locking ears 45a provided on an inwardly extending neck portion 45b formed on cover component 45. Upon relative rotation between cover component 45 and connector component 76, the parts will be securely interconnected and maintained in sealed engagement by elastomeric O-rings 75 and 77 (FIG. 3). Second manifold 74 also includes an inlet passageway 74a that is in communication with inlet passageway 70 of first manifold 66 in the manner shown in FIG. 3. Second manifold 74 further includes first and second counterbores 74b and 74c respectively. Counterbores 74b and 74c function to support a check valve 78 which is of the configuration best seen in FIGS. 3 and 4. Check valve 78 forms a part of the flow control means for controlling fluid flow from the inlet of the device to fill tube 56 via the fill passageways 70 and 74a formed in manifolds 66 and 74 respectively. Check valve 78 permits fluid flow inwardly of the device via an inlet passageway 76b provided in connector component 76 but prevents fluid flow in the opposite direction. Disposed proximate flow passageway 76b is a slit septum 80, which comprises a part of the fill means of the invention. Septum 80 is held in position by retainer means shown here as a retainer sleeve 82. Retainer sleeve 82 has a tapered inner wall 82a which engages septum 80 and sealably holds the septum in position within member 82 when member 82 is secured to connector component 76. Septum 80 is accessible by a piercing cannula of a syringe device when cover 45 is disconnected from connector 76. The base and cover components of the fluid delivery device can be constructed from the cover materials described in incorporated by reference Ser. No. 08/919,147. Ser. No. 08/919,147 should also be consulted for an identification of the various distendable membrane materials that can be used to construct distendable member 48 and for a description of the various coatings that can be applied thereto.

With the construction thus described, fluid can be introduced via septum 80 into inlet passageway 76b of connector 76, past check valve 78, into fill passageway 74a of manifold 74, into passageway 70 of manifold 66 and then into the interior 56a of fill tube 56. Fluid flowing into fill tube 56 will flow through inlet/outlet ports 58 into pressural engagement with the elastomeric member 48 causing it to distend outwardly from the first configuration shown in FIG. 4 to the second configuration shown in FIG. 3 thereby forming fluid reservoir 46. With reservoir 46 appropriately filled with the beneficial agent to be delivered to the ruminant, the egg-shaped device of the invention can be inserted into the rumen of the animal through the animal's mouth. Disposed within an internal chamber defined by the outer wall of base 43 and an inner, dome-shaped wall 84 is a weight 86 having a density such that the overall density of the delivery device will be on the order of 2.0. With this density the device will be effectively retained within the rumen of the ruminant and will not be regurgitated therefrom. Components of the fluid delivery device can be constructed from materials identified in U.S. Pat. No. 5,205,820 issued to one of the present inventors.

After the device of the invention has been inserted into the rumen of the animal, the body temperature of the animal will cause the heat expandable gel 52 to expand and act upon distendable member 48 in a manner to cause the member to tend to return to its original starting configuration as shown in FIG. 4 wherein it was in engagement with fill tube 56. As the heat expandable gel controllably urges distendable member 48 toward its original starting configuration, fluid will be controllably urged through ports 58 of the fill tube and into outlet passageway 72 of manifold component 66. The fluid under pressure will then flow through a leg 72a of passageway 72 and then toward outlet 50 of the device.

Figure 6:
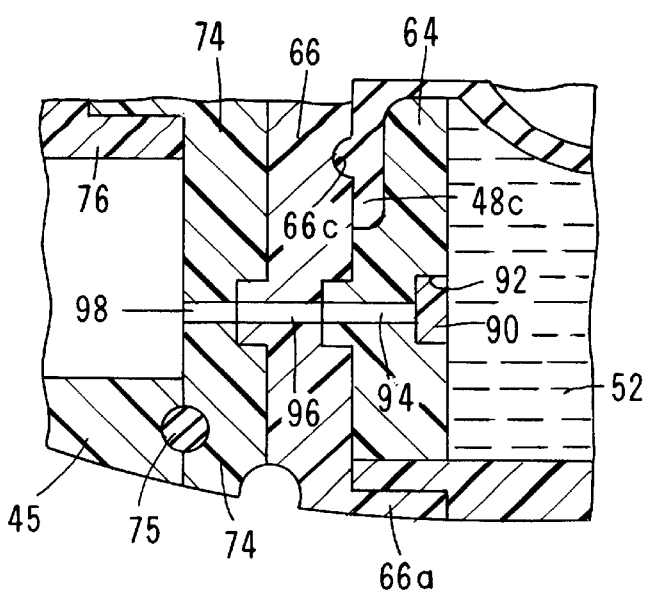
FIG. 6 is an enlarged, cross-sectional view of the area designated in FIG. 3 by the numeral 6.
Figure 7:
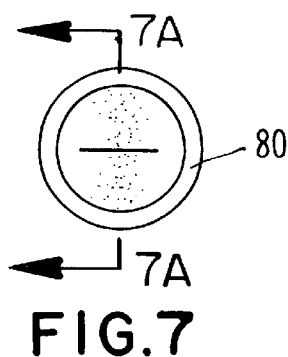
FIG. 7 is a rear view of the slit septum of the device, which forms a part of the fill means of the invention.
Figure 7A:
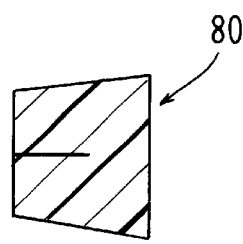
FIG. 7A is a cross-sectional view taken along lines 7A—7A of FIG. 7.

An important feature of the apparatus of the present invention resides in the flow rate control means comprises, in addition to the heat expandable means or gel 52, an impedance means which is here shown as a porous impedance frit 88 that is secured within outlet 50. This important flow rate control means precisely controls the rate of fluid flow from reservoir 46 through outlet 50 of the device and into the rumen of the animal. To appropriately vent to atmosphere any gasses that may be contained within chamber 43a and to contain gel 52, a porous gas vent ring and gel block 90 is provided within a groove 92 formed in retainer ring 64. Gasses within chamber 43a will flow through ring 90 into a passageway 94 formed in retainer ring 64, into a passageway 96 formed in manifold 66, into passageway 98 formed in manifold 74 and then into cover component 45 (see also FIG. 6).

Figure 25:
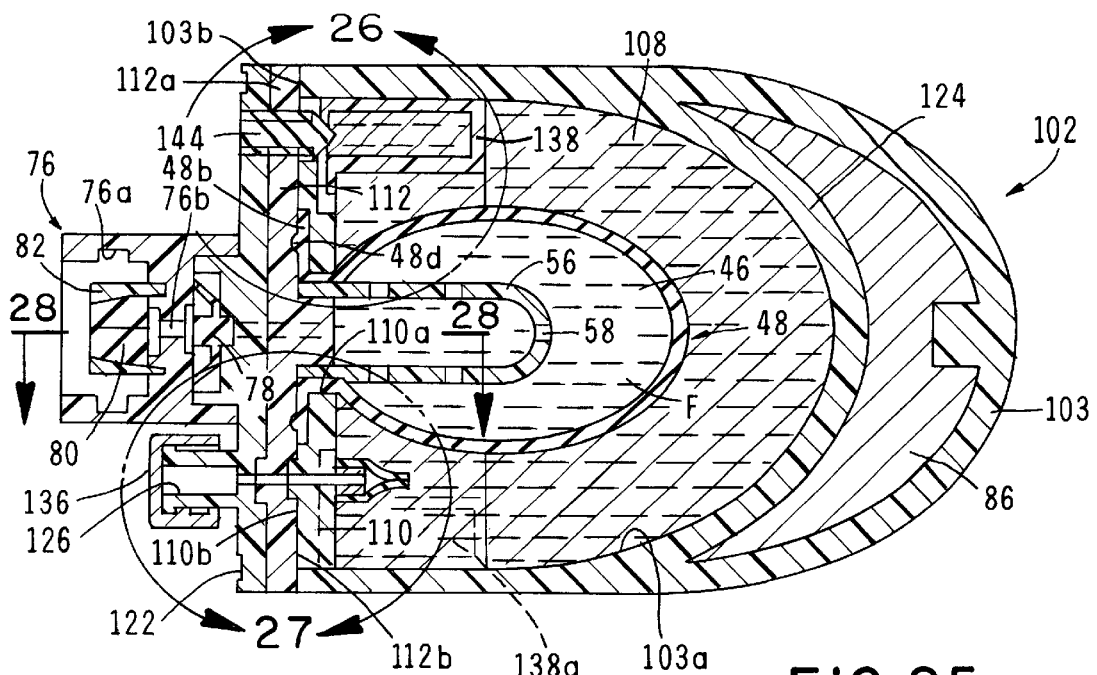
FIG. 25 is a cross-sectional view taken along lines 25—25 of FIG. 24.

Turning next to FIGS. 21 through 30, an alternate form of the apparatus of the invention for use in administering beneficial agents to a ruminant is there shown and generally designated by the numeral 100. As best seen by referring to FIGS. 21 and 22, this latest embodiment of the invention is somewhat similar to that shown in FIGS. 1 through 20. Accordingly, like numerals are used in FIGS. 21 through 30 to identify like components. As before, the apparatus comprises a generally egg-shaped housing 101 which includes a base assembly 102 and a cover assembly 104. Formed within an internal chamber of 103a of a base component 103 of base assembly 102, is a fluid reservoir 46 for containing the beneficial agent to be delivered to the ruminant (FIG. 25). Fluid reservoir 46 is formed by an elastomeric distendable member 48, which as in the earlier described embodiment, is distended into the configuration shown in FIG. 25, by the introduction of the beneficial agent into the device via the fill means of the invention.

The apparatus of this latest form of the invention also includes a heat-expandable means, which is carried within a chamber 103a and functions to controllably urge fluids contained within reservoir 46 to flow outwardly into the rumen of the ruminant through the delivery means of the invention which includes an outlet 50 formed between manifolds 122 and 112. The heat-expandable means is once again provided in the form of a thermal expandable polymer mass 108 which is contained within chamber 103a in the manner best seen in FIG. 25. As before, expandable mass 108 can take several forms but, for the reasons previously discussed, a particularly attractive form for devices of this alternate form of the invention is semisolid form such as a gel. Examples of suitable phase-transition gels are disclosed in Tanka et al, U.S. Pat. Nos. 4,732,930; Re-35068 and 5,403,893.

Figure 22:
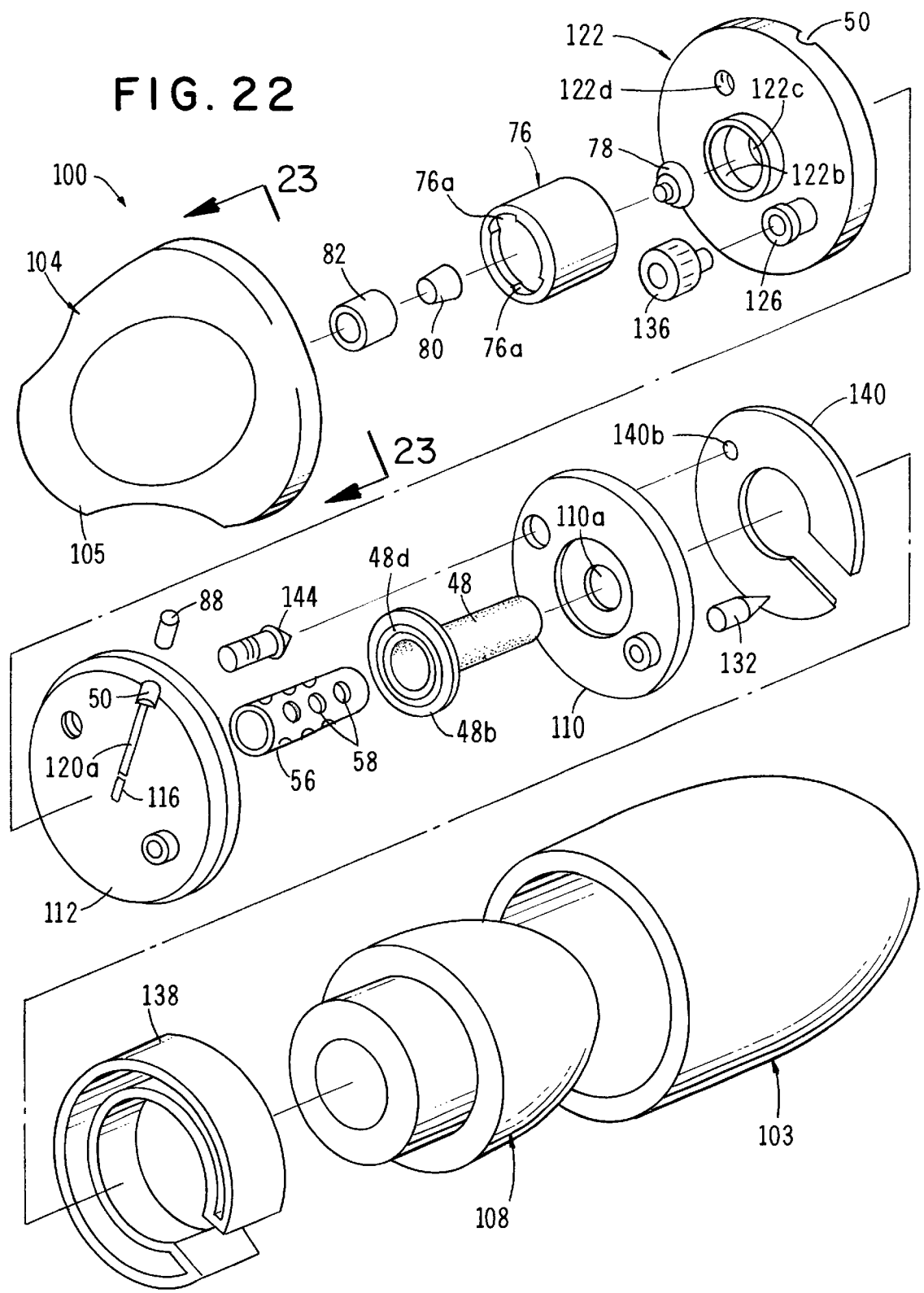
FIG. 22 is a generally perspective, exploded view of the delivery device shown in FIG. 21.

Turning particularly to FIGS. 22 and 25, the previously identified fill tube extends into chamber 103a and cooperates with elastomeric member 48 to form reservoir 46 when the beneficial agent is introduced into the fill tube 56 by the fill means of the invention. As in the earlier described embodiment, when the heat expandable mass 108 is heated by the body heat of the ruminant, it will expand and act upon distendable member 48 in a manner to tend to return the member toward its starting configuration and to controllably force the fluid "F", which is contained within the reservoir 46, outwardly of the device, through the delivery means, and into the rumen of the animal. As in the earlier described form of the invention, as member 48 moves toward its starting configuration (see FIG. 22), it will closely conform to the shape of fill tube 56 as the heat expandable mass 108 expands thereby causing a complete and controlled expelling of fluid from reservoir 46 through the fluid outlets of the fill tube 56 and then into the delivery means of the apparatus, the details of construction of which will presently be described.

Figure 26:
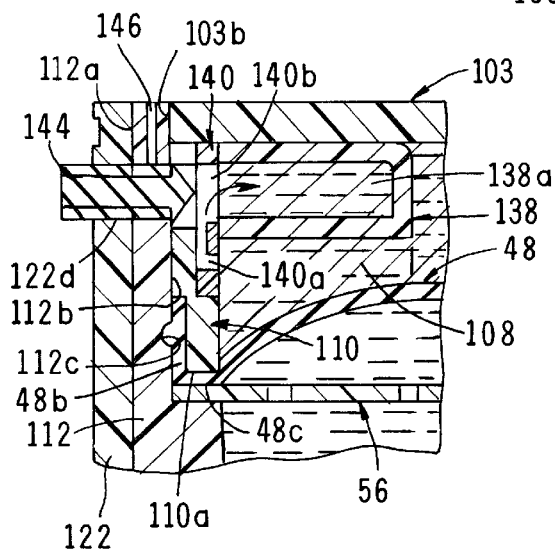
FIG. 26 is an enlarged, cross-sectional view of the area designated in FIG. 25 by the numeral 26.

Member 48, which is of the configuration previously described, is held in position within chamber 103a by means of a retaining ring 110 which is of a similar construction to ring 64 and is received within the open end of base member 103 in the manner best seen in FIG. 25. As best seen in FIGS. 25 and 26 retaining ring 110 includes a central opening 110a which closely receives the neck portion 48c of elastomeric member 48 and functions to maintain the neck portion in sealing engagement with the outer wall of fill tube 56 (FIG. 25). Fill tube 56 is, in turn, held in position within chamber 103a by being bonded to first manifold component 112. Manifold component 112 is somewhat similar in construction to manifold component 66, but includes a peripheral portion 112a which buts up against an edge 103b of base 103 (see also FIGS. 26 and 27).

When the manifold component 112 is disposed in engagement with base 103, in the manner shown in FIG. 25, flange portion 48b of distendable member 48 is securely clamped between the inner face 112b of manifold component 112 and the outer face 110b of retaining ring 110 with protuberance 48d being maintained in sealable engagement within a circumferentially extending groove 112c formed in manifold component 112. As indicated in FIG. 28, manifold component 112 is provided with a fill passageway 116 which is in communication with the interior of fill tube 56 and is also provided with a delivery passageway 120 (FIG. 28) that is also in communication with the interior of fill tube 56. Disposed in engagement with manifold 112 is a second manifold 122 which is interconnected with cover 105 by the previously described connector means or connector component 76. More specifically, circumferentially spaced slots 76a of connector 76 lockably receive a pair of circumferentially spaced locking ears 105a provided on an inwardly extending neck portion 105b formed on cover component 105 (see FIG. 30). Upon relative rotation between cover component 105 and second manifold 122, the parts will be securely interconnected and maintained in sealed engagement by elastomeric O-rings 75 and 77. Second manifold 122 also includes an inlet passageway 122a that is in communication with inlet passageway 116 of first manifold 112 in the manner shown in FIG. 28. Second manifold 122 further includes first and second counterbores 122b and 122c respectively. Counterbores 122b and 122c function to support a check valve 78, which is of the character previously described. As before, valve 78 permits fluid flow inwardly of the device via an inlet passageway 76b provided in connector component 76 but prevents fluid flow in the opposite direction.

Figure 27:
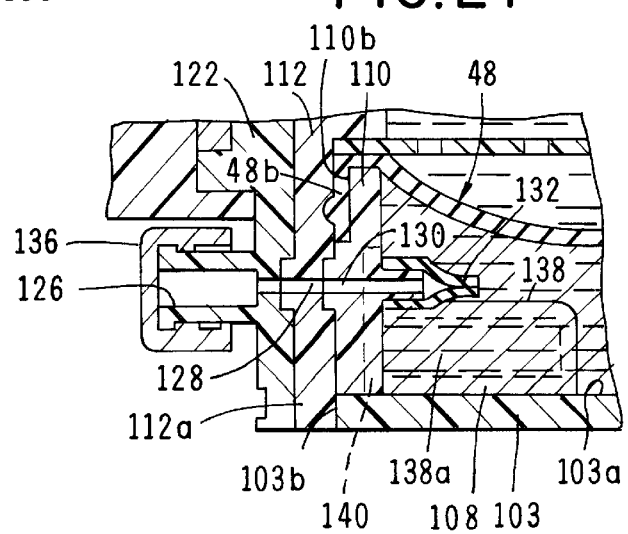
FIG. 27 is an enlarged, cross-sectional view of the area designated in FIG. 25 by the numeral 27.

A novel feature of this latest embodiment of the invention is the provision of gel filling means for filling chamber 103a in the field with the heat expandable gel 108. As best seen in FIG. 27, this gel filling means here comprises a fill port 126 formed in manifold 122 and gel filling passageways 128 and 130 formed in first manifold 112 and retaining ring 110 respectively for communication with fill port 126. Also forming a part of the gel filling means is check valve 132 mounted on retaining ring 110 (FIGS. 25 and 27) which permits gel flow into chamber 103a but blocks flow in the opposite direction. Fill port 126 here comprises a luer port to which a fill line with a luer connector can be interconnected. When the port is not in use it can be sealably closed by a luer closure cap 136 (see also FIG. 27).

The gel filling means further includes an overflow reservoir component 138 which is generally annular in shape and is disposed within chamber 103a in the manner shown in FIGS. 25 and 28. The overflow reservoir solves the problem of over filling in the field by providing a suitable catch reservoir to safely accommodate excess gel introduced into the device during field filling. A reservoir cover plate 140 is disposed between retaining ring 110 and gel reservoir component 138 to form a (see FIGS. 22 and 28) gel reservoir 138a. Plate 140 is provided with a gel overflow pathway 140a that is in communication with reservoir 138a and an entrance port 140b that also communicates with reservoir 138a (FIG. 26) and permits overflow gel to enter the reservoir in the manner shown in FIG. 26.

An elastomeric reservoir vent seal 144 is threadably received within a bore 122d formed in manifold 122 and functions to prevent gel from flowing through a gas vent 146 formed in manifold 112 (FIG. 26). Vent 146 is constructed and arranged so as to permit gases trapped within chamber 103a to be vented to atmosphere during the gel filling step. During this filling step gel is forced under pressure into gel fill port 126, through passageways.

Disposed proximate flow passageway 76b is a slit septum 80, which comprises a part of the fill means of the invention. Septum 80 is held in position within a connector 76 by the retainer means or retainer sleeve 82. Septum 80 is accessible by a piercing cannula of a syringe device when cover 105 is disconnected from connector 76.

With the construction described in the preceding paragraphs, fluid can be introduced via septum 80 into inlet passageway 76b of connector 76, past check valve 78, into fill passageway 122a of manifold 122, into passageway 116 of manifold 112 and then into the interior 56a of fill tube 56. Fluid flowing into fill tube 56 will flow through inlet/outlet ports 58 into pressural engagement with the elastomeric member 48 causing it to distend outwardly from the first configuration shown in FIG. 22 to the second configuration shown in FIG. 25 thereby forming fluid reservoir 46. With reservoir 46 appropriately filled with the beneficial agent to be delivered to the ruminant, the egg-shaped device of the invention can be inserted into the rumen of the animal through the animal's mouth. Disposed within an internal chamber defined by the outer wall of base 103 and an inner, dome-shaped wall 124 (FIG. 25) is the previously described weight 86 which has a density such that the overall density of the delivery device will be on the order of 2.0. With this density the device will be effectively retained within the rumen of the ruminant and will not be regurgitated therefrom.

After the device of the invention has been inserted into the rumen of the animal, the body temperature of the animal will cause the heat expandable gel 108 to expand and act upon distendable member 48 in a manner to cause the member to tend to return to its original starting configuration as shown in FIG. 22 wherein it was in engagement with fill tube 56. As the heat expandable gel controllably urges distendable member 48 toward its original starting configuration, fluid will be controllably urged through ports 58 of the fill tube and into outlet passageway 120 of manifold component 112. The fluid under pressure will then flow through a leg 120a of passageway 120 and then toward outlet 50 of the device.

The apparatus of this latest embodiment also includes flow rate control means provided in the form of porous impedance frit 88 that is secured within outlet 50 (FIG. 28). As before, the heat expandable gel precisely controls the rate of fluid flow from reservoir 46 through outlet 50 of the device and into the rumen of the animal.

Referring next to FIGS. 31 through 40, still another form of the apparatus of the invention for use in administering beneficial agents to a ruminant is there shown and generally designated by the numeral 150. Once again, this embodiment of the invention is somewhat similar to that shown in FIGS. 1 through 20 and like numerals are used in FIGS. 31 through 40 to identify like components. As in the earlier described embodiments, the apparatus here comprises a generally egg-shaped housing 151 which includes a base assembly 152 and a cover assembly 154. Formed within an internal chamber of 153a of a base component 153 of base assembly 152, is a fluid reservoir 156 for containing the beneficial agent to be delivered to the ruminant (FIG. 33).

Fluid reservoir 156 is formed by an elastomeric distendable member 158, which as in the earlier described embodiment, is distended into the configuration shown in FIG. 33, by the introduction of the beneficial agent into the device via the fill means of the invention. As shown in FIG. 33A, distendable member 158 is of a laminate construction comprising laminates 158a and 158b. Additionally, as shown in FIG. 33A, diffusion barrier coatings are provided on member 158 to achieve desired liquid, gas or vapor permeability characteristics for the membrane assemblage. Examples of diffusion barrier coatings, such as coating 159, include nitrile rubbers, urethanes, parylene (a family of aromatic thermoplastic polymers), or fluoropolymers (such as, for example, a material sold by DuPont Dow Elastomers, Wilmington, Del. under the name and style of "VITON"). Further, the laminate construction may also be intercoated between the laminates with a coating 161 that will promote the bondability of the laminates. By way of example, liquid crystal polymers such as a material sold by DuPont under the name and style of "ZENITE" can be used for this purpose. In addition to coatings, the distendable member 158 can also be interfacially treated to alter the molecular surface of the membrane. By way of example, corona or plasma treatments can vary the surface tension characteristics of the membrane such that it may increase of decrease its adhesive qualities.

The apparatus of this latest form of the invention also includes a heat-expandable means, which is carried within a chamber 153a and functions to controllably urge fluids contained within reservoir 156 to flow outwardly into the rumen of the ruminant through the delivery means of the invention which includes a pair of diametrically opposed outlets 160 formed in housing 151 (FIG. 34). The heat-expandable means is once again provided in the form of a thermal expandable polymer mass 162 which is contained within chamber 153a in the manner best seen in FIG. 33. As before, expandable mass 162 can take several forms including a semisolid form such as a gel. A weight 163 is disposed within a chamber 163a of the base assembly which surrounds chamber 153a (FIG. 33).

Turning particularly to FIGS. 31A and 33, a slightly differently configured fill tube 164 extends into chamber 153a and cooperates with elastomeric member 158 to form reservoir 156 when the beneficial agent is introduced into the fill tube by the fill means of the invention. As in the earlier described embodiment, when the heat expandable mass 162 is heated by the body heat of the ruminant, it will expand and act upon distendable member 158 in a manner to tend to return the member toward its starting configuration and to controllably force the fluid "F", which is contained within the reservoir 156, outwardly of the device through the delivery means, and into the rumen of the animal. As member 158 moves toward its starting configuration (see FIG. 31A), it will cause a complete and controlled expelling of fluid from reservoir 156 through the fluid outlets 164a of the fill tube 164 and then into the delivery means of the apparatus, the details of construction of which will presently be described.

Member 158 is held in position within chamber 153a by means of a manifold 168 having a generally cylindrically shaped neck 168a that extends into chamber 153a. The open mouth of elastomeric member 158 is receivable over neck 168a and a clamping ring 170 functions to maintain the elastomeric member in sealing engagement with neck 168a in the manner shown in FIGS. 33 and 35. Manifold component 168 includes a peripheral portion 169 which butts up against an edge 173a of a base member 173 which forms a part of base assembly 152 (see also FIG. 35). When the manifold component 168 is disposed in engagement with base member 173, in the manner shown in FIG. 33, fill tube and elastomeric member 158 protrudes into chamber 153a and are surrounded by heat expandable means 162. As indicated in FIG. 33, manifold component 168 is provided with a fill passageway 174 which is in communication with the interior of fill tube 164 and is also provided with a delivery passageway 176 (FIG. 35) that is also in communication with the interior of fill tube 164. Passageway 176, in turn, communicates with a transverse delivery passageway 178 that communicates with outlet ports 160 (see also FIG. 34).

Disposed in engagement with manifold 168 is a second manifold 180 which is interconnected with a cover component 154a of a cover assembly 154 by the previously described connector means or connector component 76. More specifically, circumferentially spaced slots 76a of connector 76 lockably receive a pair of circumferentially spaced locking ears 154b provided on an inwardly extending neck portion 154c formed on cover component 154a (see FIG. 33). Upon relative rotation between cover component 154a and second manifold 180 to which connector 76 is affixed, the parts will be securely interconnected and maintained in sealed engagement by elastomeric O-ring 77. Second manifold 180 also includes an inlet passageway 180a that is in communication with inlet passageway 174 of first manifold 168 in the manner shown in FIG. 33. Second manifold 180 further includes first and second counterbores 181 and 183 respectively (see FIG. 35). Counterbores 181 and 183 function to support a check valve 78, which is of the character previously described. As before, valve 78 permits fluid flow inwardly of the device via an inlet passageway 76b provided in connector component 76 but prevents fluid flow in the opposite direction.

Figure 37:
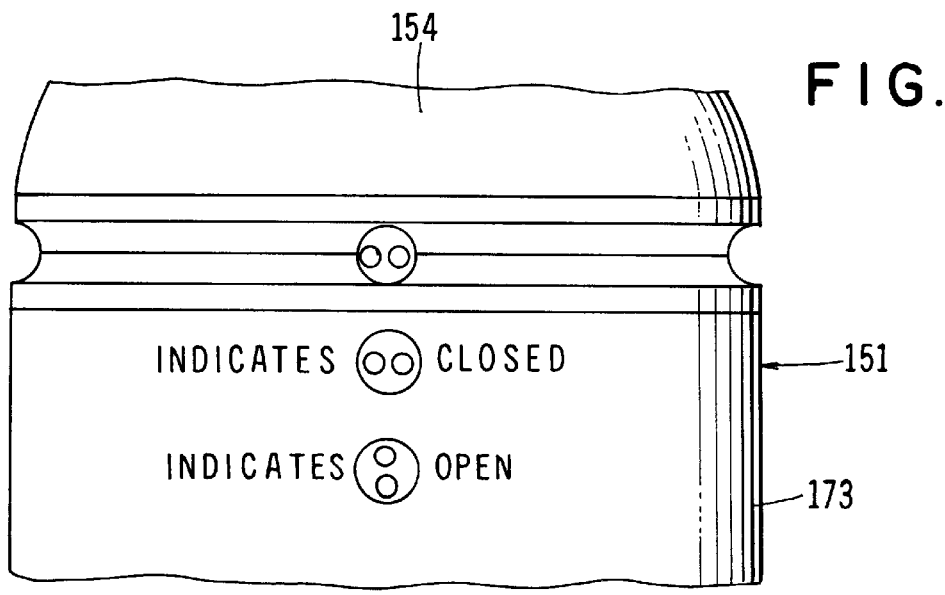
FIG. 37 is a greatly enlarged view taken along lines 37—37 of FIG. 33.
Figure 38:
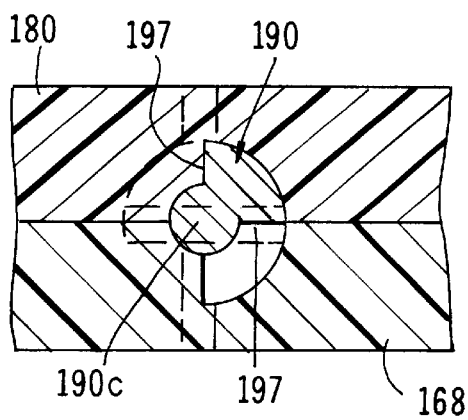
FIG. 38 is a greatly enlarged, cross-sectional view taken along lines 38—38 of FIG. 33.
Figure 39:
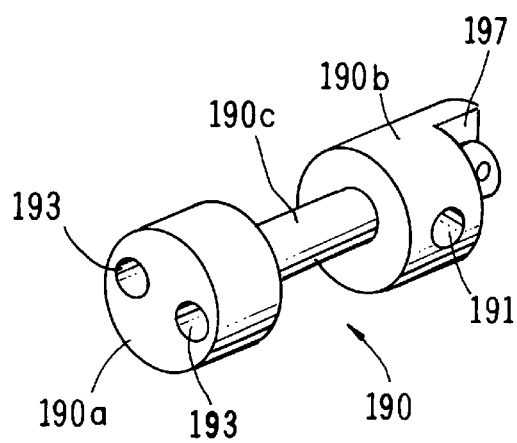
FIG. 39 is an enlarged, generally perspective front view of the vent control element of the delivery device of the invention.
Figure 40:
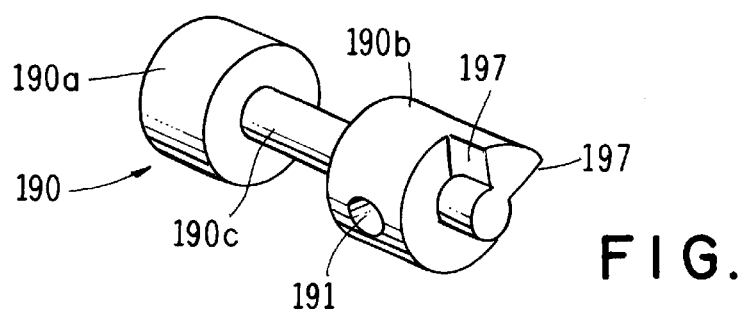
FIG. 40 is an enlarged, generally perspective rear view of the vent control element shown in FIG. 39.

A novel feature of this latest embodiment of the invention is the provision of vent closure means for opening and closing vent passageways 186 and 187 formed in manifolds 168 and 180 respectively (FIGS. 33 and 36). These vent passageways are necessary to vent chamber 153a during the gel filling step and also during reservoir filling step which causes elastomeric member 158 to expand within chamber 153a in the manner shown in FIG. 33. As best seen in FIGS. 39 and 40, this vent closure means here comprises a control member 190 having a head portion 190a, a flow control portion 190b and a connector 190c that extends between and connects portions 190a and 190b. Control member 190 is rotatably carried between manifolds 168 and 180 in the manner shown in FIG. 33 with flow control portion 190b disposed intermediate vent passageways 186 and 187. Flow control portion 190b has a through bore 191 that can be aligned with vent passageways 186 and 187 when the control member is rotated from the vent closed position shown in FIG. 36 to a vent open position wherein passageway 191 is aligned with vents 186 and 187. To rotate member 190, head portion 190a is provided with spanner holes 193 which receive tangs 195 provided on a physician's key 196 of the character shown in FIG. 31A. Flow control portion includes stop shoulders 197 which abut the manifold compartments in the manner shown in FIG. 38 and function to control the extent of rotation of the control member. As shown in FIG. 37, indicia provided on housing 151 indicate the open and closed position of the control member.

Figure 43A:
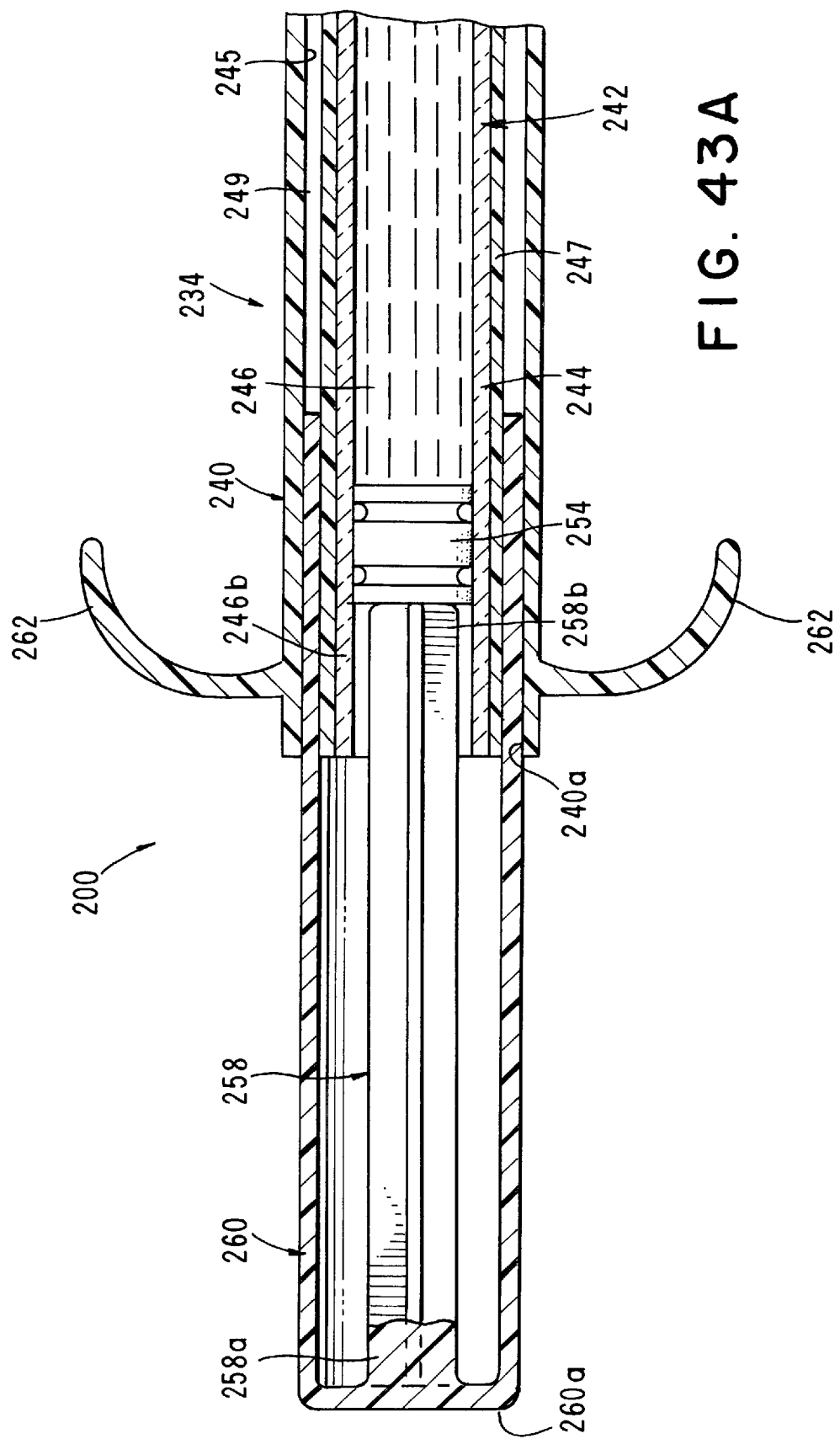
FIG. 43 is a side-elevational, cross-sectional view of the assemblage shown in FIG. 41.
Figure 43B:
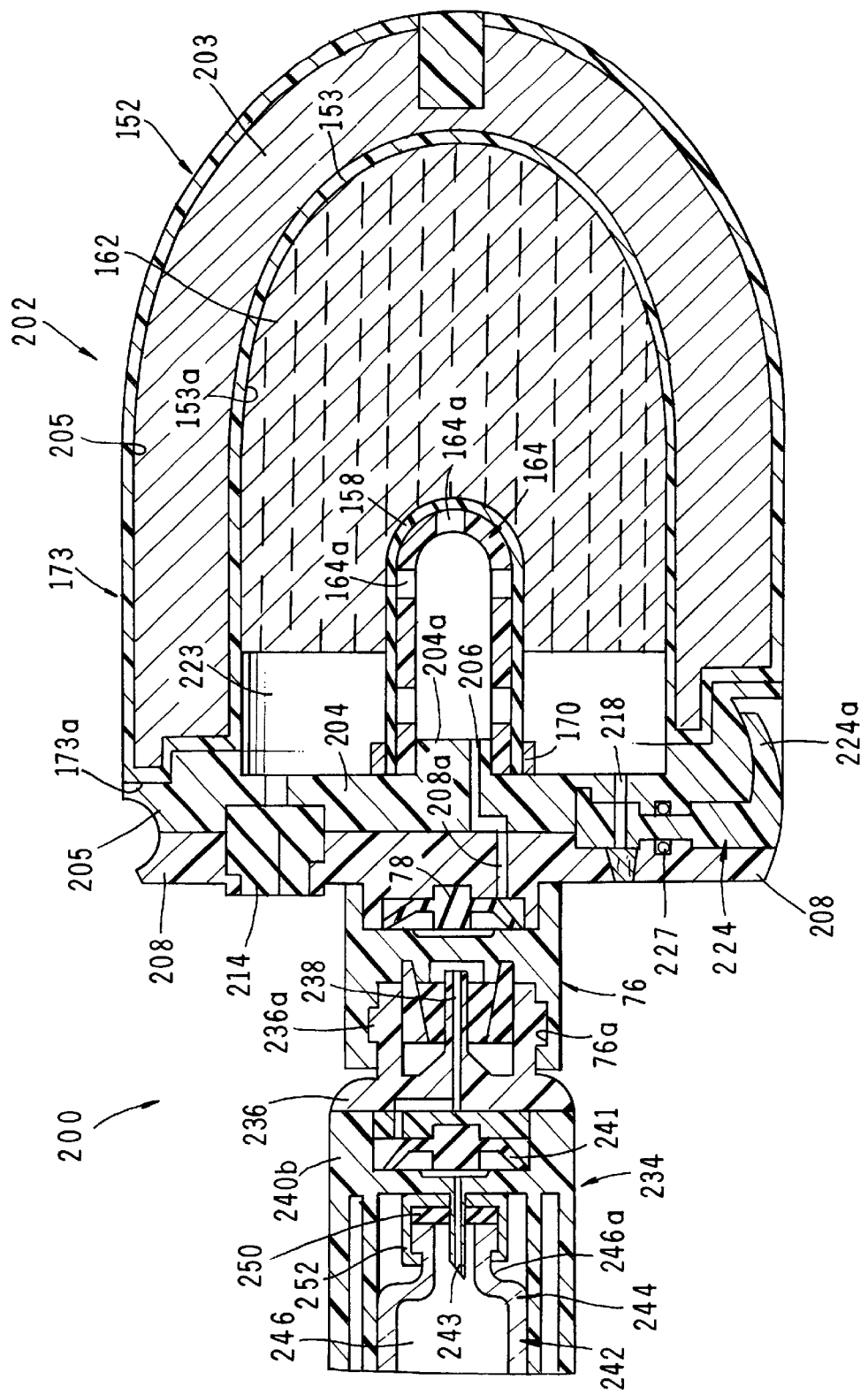
Figure 44:
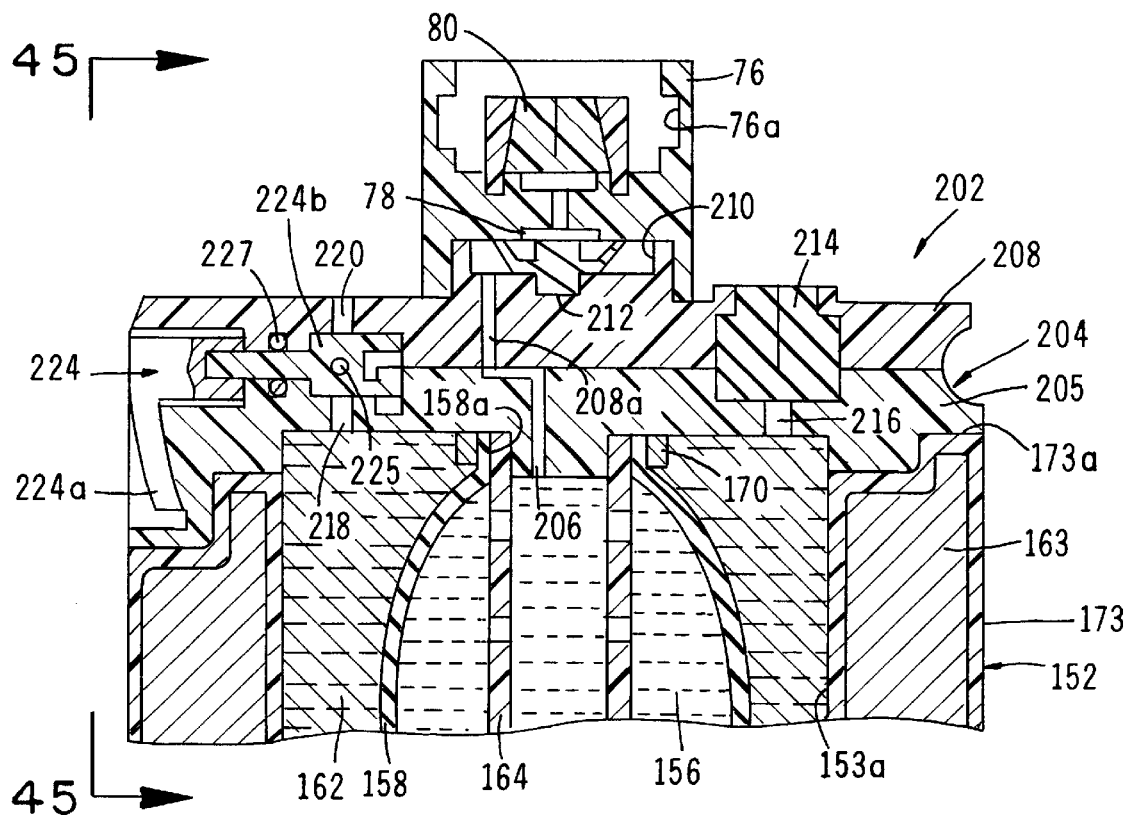
FIG. 44 is an enlarged, fragmentary, cross-sectional view of the portion of the device shown in FIG. 43 with the fill assembly removed.

Turning now to FIGS. 41 through 50, still another embodiment of the invention is there shown and generally designated by the numeral 200. This embodiment of the invention is quite similar to that shown in FIGS. 31 through 40 and like numerals are used in FIGS. 41 through 50 to identify like components. As in the earlier described embodiments, the apparatus here comprises a generally egg-shaped housing similar to that shown in FIG. 33 which includes a slightly different base assembly 202 (FIG. 41) and a cover assembly similar to cover assembly 154. Formed within an internal chamber of 153a of a base component 153 of base assembly 202, is a fluid reservoir 156 for containing the beneficial agent to be delivered to the ruminant (FIG. 44). Fluid reservoir 156 is formed by an elastomeric distendable member 158, which as in the earlier described embodiment, is distended into the configuration shown in FIG. 44, by the introduction of the beneficial agent into the device via the fill means of the invention.

The apparatus of this latest form of the invention also includes a heat-expandable means which is carried within a chamber 153a and functions to controllably urge fluids contained within reservoir 156 to flow outwardly into the rumen of the ruminant through the delivery means of the invention which includes a pair of diametrically opposed outlets 160 of the character shown FIG. 34. The heat-expandable means is once again provided in the form of a thermal expandable polymer mass 162 which is contained within chamber 153a in the manner best seen in FIG. 43. As before, expandable mass 162 can take several forms including a semisolid form such as a gel. A weight 203, which is disposed within a chamber 205 that surrounds chamber 153a once again functions to retain the device within the animal's rumen.

Turning particularly to FIGS. 43 and 44, it can be seen that fill tube 164 extends into chamber 153a and cooperates with elastomeric member 158 to form reservoir 156 when the beneficial agent is introduced into the fill tube by the fill means of the invention. As in the earlier described embodiments, when the heat expandable mass 162 is heated by the body heat of the ruminant, it will expand and act upon distendable member 158 in a manner to tend to return the member toward its starting configuration and to controllably force the fluid, which is contained within the reservoir 156, outwardly of the device, through the delivery means, and into the rumen of the animal. As member 158 moves toward its starting configuration, it will expel fluid from reservoir 156 at a controlled rate through the fluid outlets 164a of the fill tube 164 and then into the delivery means of the apparatus, which is of the character previously described.

Member 158 is held in position within chamber 153a by means of a manifold 204 having a generally cylindrically shaped neck 204a that extends into chamber 153a (FIG. 44). The open mouth 158a of elastomeric member 158 is receivable over neck 204a and a clamping ring 170 functions to maintain the elastomeric member in sealing engagement with neck 204a in the manner shown in FIGS. 43 and 44. Manifold component 204 includes a peripheral portion 205 which butts up against an edge 173a of a base member 173 that forms a part of base assembly 152. When the manifold component 204 is disposed in engagement with base member 173, in the manner shown in FIG. 43, both the fill tube and elastomeric member protrude into chamber 153a and are surrounded by heat expandable means 162. As indicated in FIG. 44, manifold component 204 is provided with a fill passageway 206 which is in communication with the interior of fill tube 164 and is also provided with a delivery passageway of the character previously described that is also in communication with the interior of fill tube 164. As before, this passageway communicates with a transverse delivery passageway that, in turn, communicates with outlet ports 160 (see, for example, FIG. 34).

Disposed in engagement with manifold 204 is a second manifold 208 which can be interconnected with a cover component 154a of a cover assembly 154 of the character seen in FIG. 33 by the previously described connector means or connector component 76. More specifically, circumferentially spaced bayonet type slots 76a of connector 76 (FIG. 44) lockably receive a pair of circumferentially spaced locking ears 154b provided on an inwardly extending neck portion 154c formed on cover component 154a (see FIG. 33). Upon relative rotation between cover component 154a and second manifold 208 to which connector 76 is affixed, the parts will be securely interconnected and maintained in sealed engagement by elastomeric O-ring 77. Second manifold 208 also includes an inlet passageway 208a that is in communication with inlet passageway 206 of first manifold 204 in the manner shown in FIG. 44. Second manifold 208 further includes first and second counterbores 210 and 212 respectively (see FIG. 44), which support check valve 78, that is of the character previously described. In this latest embodiment of the invention, manifolds 204 and 208 carry a slit septum 214 which can be used to introduce gel 162 into chamber 153a via a passageway 216 formed in manifold 204 (FIG. 44). Septum 214 is of conventional construction and is pierceable by a cannula of a conventional syringe assembly carrying gel 162.

Figure 45:
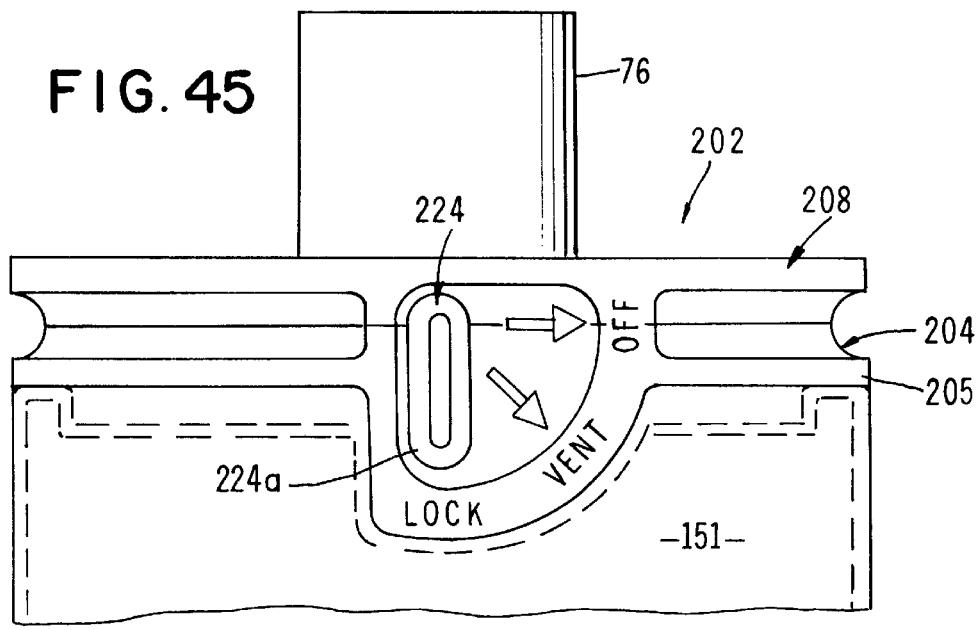
FIG. 45 is an enlarged view taken along lines 45—45 of FIG. 44.
Figure 46:
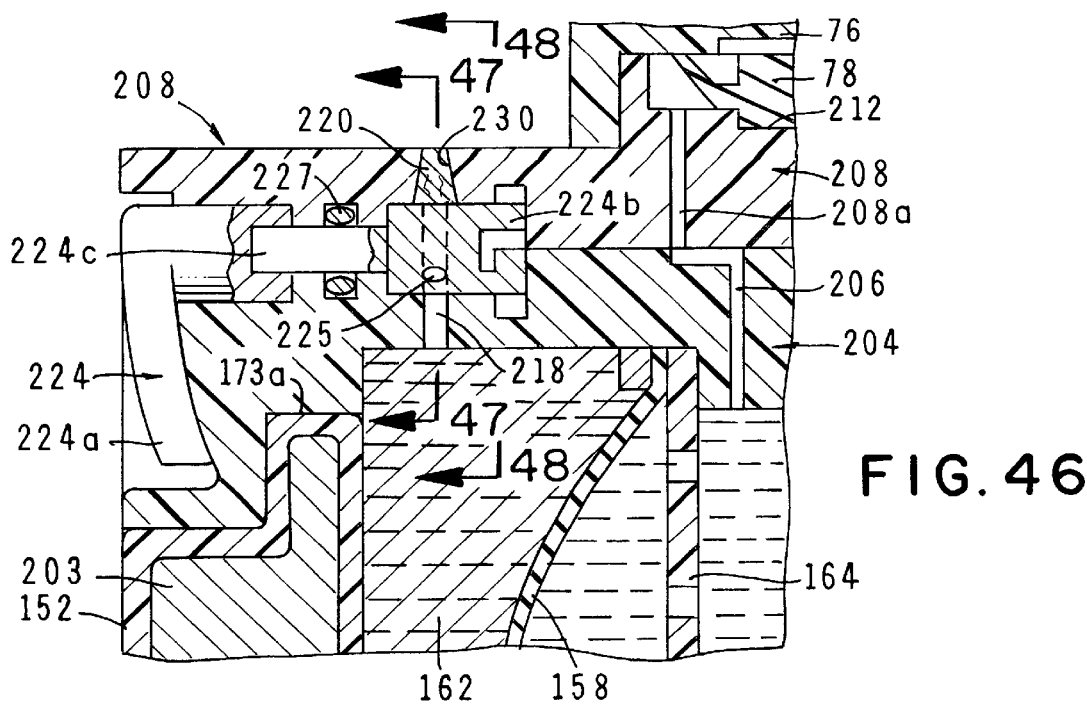
FIG. 46 is an enlarged, cross-sectional view of the vent control means for controlling the flow of gases through the vent passageway of the base assembly.
Figure 47:
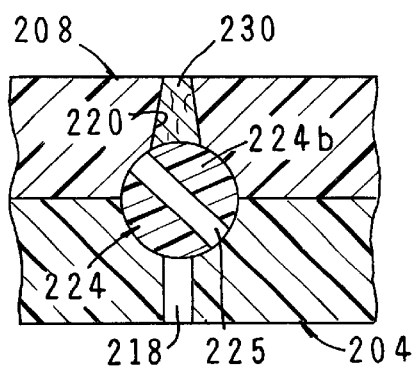
FIG. 47 is a cross-sectional view taken along lines 47—47 of FIG. 46.
Figure 48:
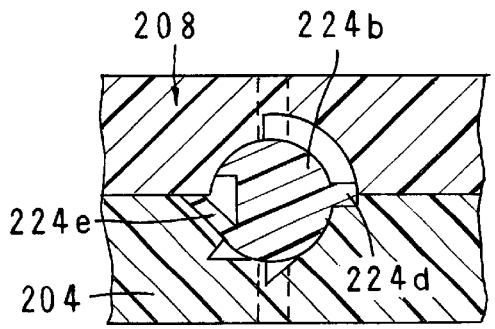
FIG. 48 is an enlarged cross-sectional view taken along lines 48—48 of FIG. 46.
Figure 49:
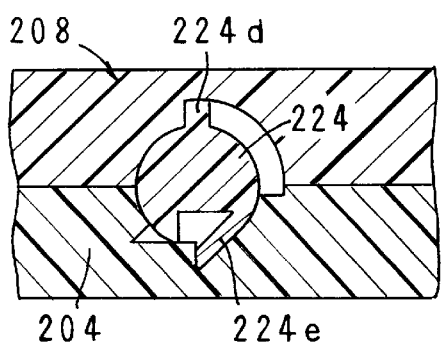
FIG. 49 is a cross-sectional view similar to FIG. 48 but showing the vent control element in a locked position.
Figure 50:
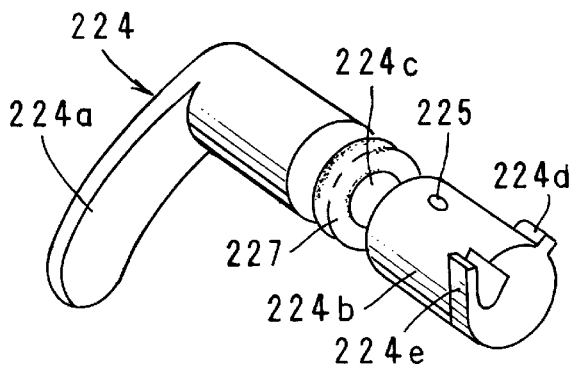
FIG. 50 is a generally perspective rear view of the vent control element.
Figure 51:
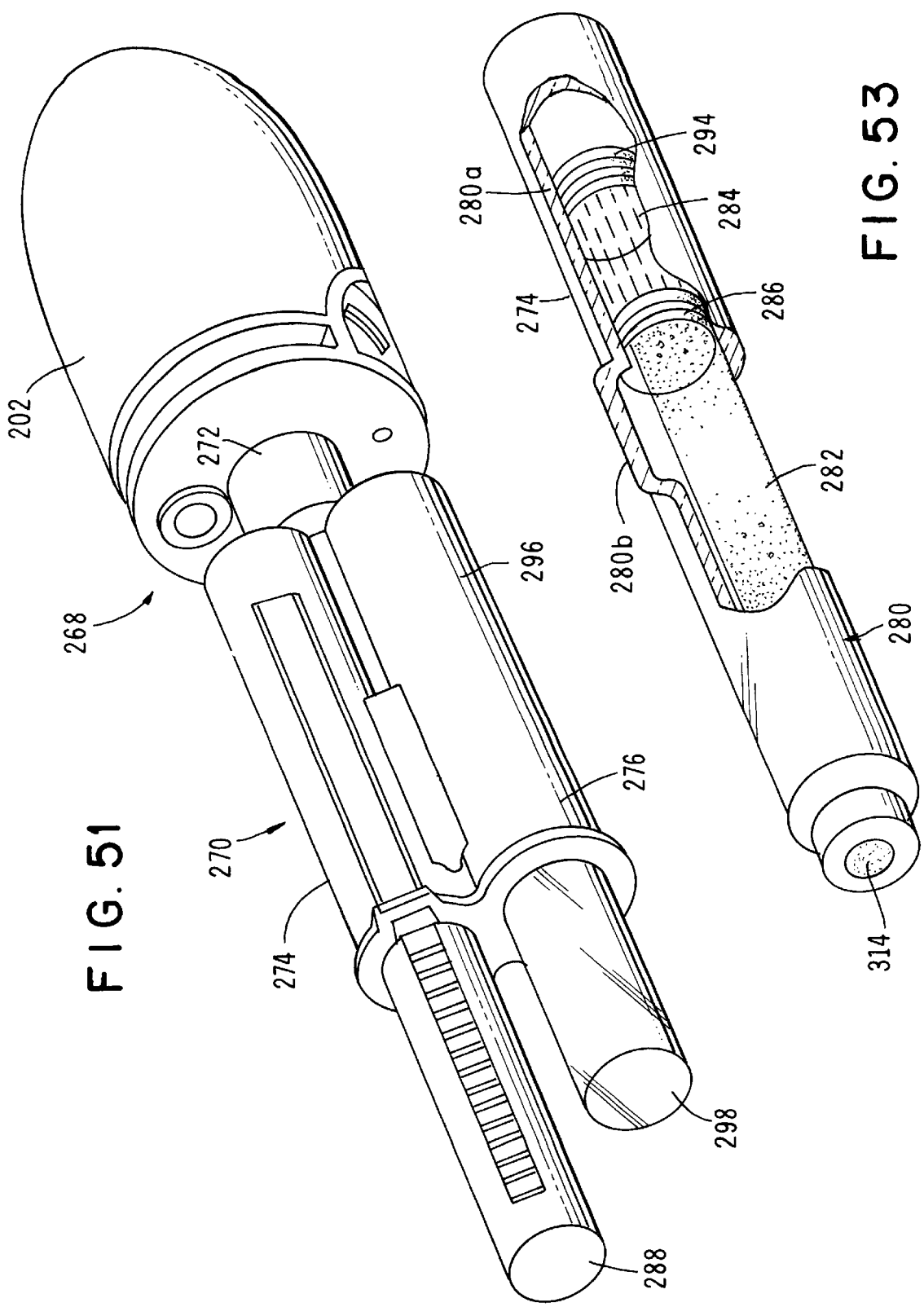
FIG. 51 is a generally perspective view of the device shown in FIG. 41 mated with an alternate form of reservoir fill assembly which comprises a dual vial system and which can be coupled with the base assembly to fill the device reservoir.

This latest embodiment of the invention is also provided with novel vent closure means for opening and closing vent passageways 218 and 220 formed in manifolds 204 and 208 respectively (FIGS. 44 and 46). Vent passageways 218 and 220 are necessary to vent chamber 153a during reservoir filling at which time elastomeric member 158 expands into chamber 153a. Passageways 218 and 220 also function to vent gases to atmosphere as the gel is heated and expands into space 223 (FIG. 43). As best seen in FIGS. 44 through 50, this vent closure means is somewhat similar to that previously described and comprises a control member 224. As shown in FIG. 50, control member 224 includes a lever arm portion 224a, a flow control portion 224b and a connector 224c that extends between and connects portions 224a and 224b. Control member 224 is rotatably carried between manifolds 204 and 208 in the manner shown in FIG. 46 with flow control portion 224b disposed intermediate vent passageways 218 and 220. As indicated in FIG. 47, flow control portion 224b has a through bore 225 that can be aligned with vent passageways 218 and 220 when the control member is rotated between a vent closed position shown in FIG. 47 to a vent open position wherein passageway 225 is aligned with vents 218 and 220. Lever arm portion 224a permits easy rotation of the control member from the off position shown in FIG. 48 to the locked position shown in FIG. 49. An O-ring 227 circumscribes connector shaft 224c and sealably connects the control member to manifolds 204 and 208 in the manner best seen in FIG. 46. As shown in FIG. 45, indicia provided on base assembly 202 indicate the off, vent and lock position of the control member. To locate the control member within the manifold, a locking shoulder 224d and a spring locking tab 224e are provided on control portion 224b (FIG. 50). As shown in FIGS. 46 and 47, a hydrophobic vent element 230 is disposed within vent passageway 220.

As best seen in FIGS. 41, 42 and 43, a fill assembly, generally designated by the numeral 234, is provided to controllably fill reservoir 156 via check valve 78 and fill passageways 206 and 208. Fill assembly 234 includes an adapter member 236, which is of a configuration somewhat similar to that of neck portion 154c of cover 154, and includes circumferentially spaced ears 236a. Ears 236a are receivable within slots 76a of base assembly connector 76 so that, upon rotation of the fill assembly relative to the base assembly, the fill assembly can be sealably interconnected to the base assembly. Carried by adapter member 236 is an outwardy extending hollow cannula 238 which is adapted to pierce cannula 80 as the adapter member is coupled with connector 76 in the manner shown in FIG. 43. Connected to adapter member 236 is an adapter housing 240 having a first open end 240a and a second end 240b. Housed within second end 240b is an umbrella type check valve 241 that controls fluid flow toward and away from hollow cannula 238. Also housed within second end 240b is an inwardly extending hollow cannula 243.

Receivable within first open end 240a of adapter housing 240 is a container assembly 242. Container assembly 242 includes a body portion 244 having a fluid chamber 246 (FIG. 43) for containing the fluid to be used to fill reservoir 156. Chamber 246 has first and second ends 246a and 246b with first end 246a being sealably closed by closure means here provided in the form of a pierceable septum assembly 250. Septum assembly 250 is held securely in position within body portion 244 by a clamping ring 252. A plunger 254 is receivable within second end 246b and is telescopically movable within chamber 246 from a first location shown in FIG. 43 where it is proximate second open end 246b to a second position where it is proximate first end 246a. The vial or body portion of container subassembly 242 can be constructed from various materials such as glass and plastic. As illustrated in FIGS. 42 and 43, adapter housing 240 has a first open end 240a and a second closed end 240b. Container subassembly 242 is telescopically receivable within open end 240a of housing 240 in the manner shown in FIG. 43.

Forming an important part of the fill assembly 234 is pusher means shown here as an elongated pusher rod 258 which functions to move plunger 254 within fluid chamber 246 from the first position to the second position. In the form of the invention shown in the drawings, pusher rod 258 has a first end 258a interconnected with a closure wall 260a of a pusher housing 260 and an opposite end 258b which engages plunger 254 and causes telescopic movement of the plunger within chamber 246 of container subassembly 242 as the pusher means is moved from the extended position shown in FIG. 43 into a container assembly encapsulating position wherein pusher housing 260 substantially encapsulates container assembly 242.

As best seen by referring to FIG. 43, the interior surface 245 of adapter housing 240 cooperates with a spaced-apart inner wall 247 to form an elongated generally annular shaped passageway 249 within which pusher housing 260 is received as the pusher housing is moved toward its container encapsulating position. To expedite insertion of the pusher housing, adapter housing 240 is provided with outwardly extending finger engaging members 262 which can be gripped by the fingers while the palm of the hand urges pusher housing 260 inwardly of passageway 249. The housing and adapter components of the fill assembly of the invention can be constructed from acrylic, polycarbonate and other similar materials well known to one skilled in the art.

Prior to mating the fill assembly with base assembly 202, a tear away seal tab 266, which sealably closes the open end of adapter member 236, is removed (FIG. 42). This done, the adapter member can be telescopically inserted into connector 76 causing piercing cannula 238 to pierce septum 80. As previously mentioned, rotation of the adapter member relative to connector 76 will lockably interconnect fill assembly 234 with base assembly 202 in the manner shown in FIG. 41.

Once a fluid flow path between cannula 238 and fill tube 164 has thusly been established, container subassembly 242 can be inserted into adapter housing 240. An inward force exerted on pusher housing 260 will then cause pusher rod 258 to move the container assembly 242 forwardly of housing 240 to a position shown in FIG. 43. In this position, inwardly extending hollow cannula 243 will pierce septum 250 of the container assembly thereby opening fluid communication between chamber 246 of the vial assembly and hollow cannula 238. As plunger 254 is moved further forwardly by pusher rod 258, the fluid contained within vial chamber 246 will flow through hollow cannula 243, past check valve 241, into hollow cannula 238 and then into fluid reservoir 156 via passageways 206 and 208a. As the fluid under pressure flows into reservoir 156, membrane 158 will be distended outwardly in the manner shown in FIG. 44. Ring 170, which clamps membrane 158 to neck 204a of manifold 204, functions to seal the membrane against neck 204a and thereby prevent leakage of fluid around the perimeter of the mouth of the membrane. During this filling step, the vent control means is in the vent position (FIG. 45) permitting the venting of gases from chamber 153a to atmosphere via vent passageways 218 and 220. Once reservoir 156 is appropriately filled, the vent control means is rotated to the lock position wherein the vent passageways are closed.

Figure 54A:
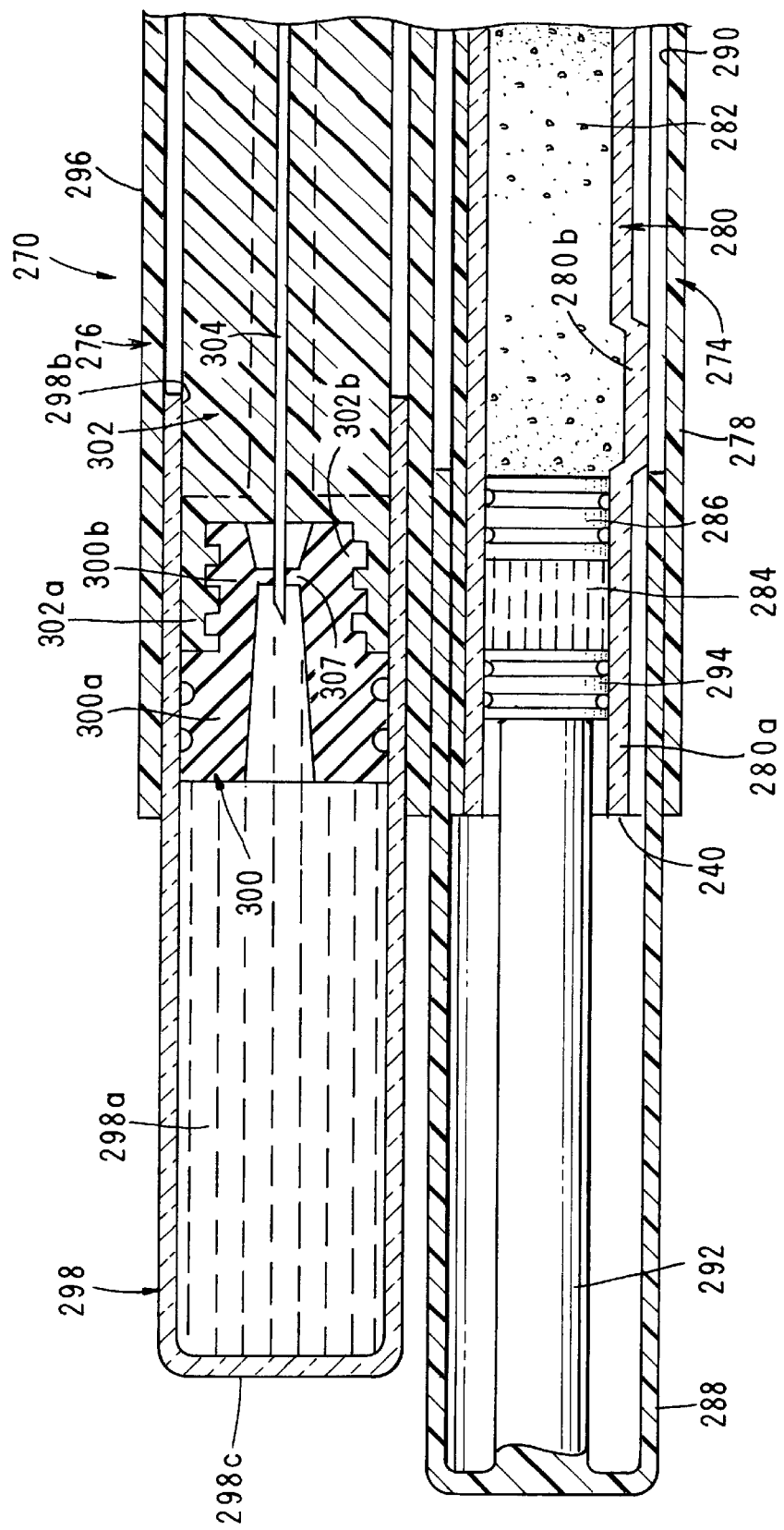
FIG. 54 is a side-elevational, cross-sectional view of the assembly shown in FIG. 51.
Figure 54B:
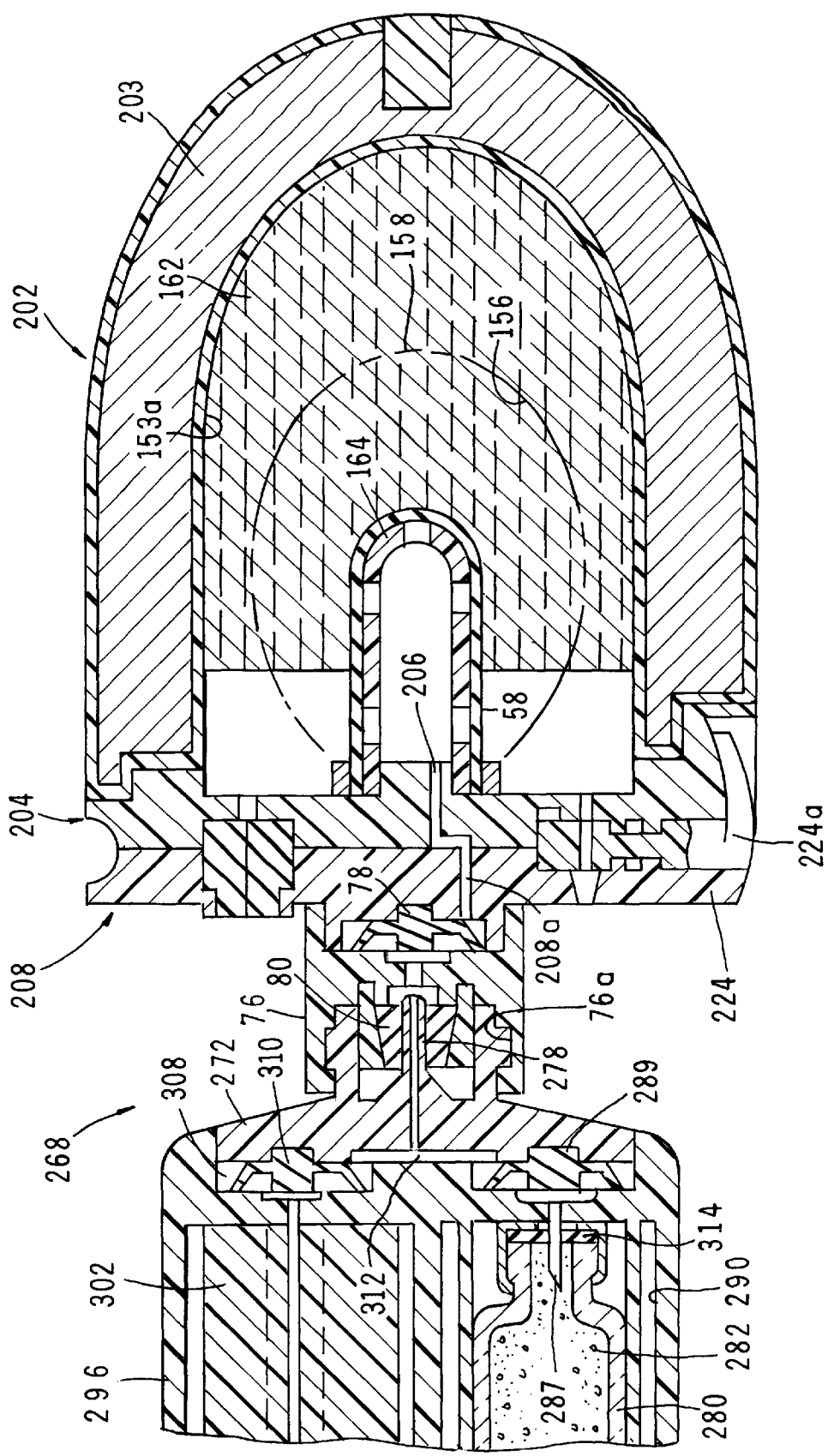

Turning next to FIGS. 51 through 54, still another form of the fluid delivery apparatus of the invention is there shown and generally designated by the numeral 268. This apparatus is also similar to the apparatus shown in FIGS. 43 through 50 and like numerals are used in FIGS. 51 through 54 to identify like components. In this latest embodiment of the invention, the base assembly 202 is identical to that previously described. However, in this latest form of the invention, an entirely different dual housing fill assembly is provided. This novel fill assembly, which is generally designated by the numeral 270, is interconnected with the connector means of the base assembly by a connector adapter member 272 that is of a somewhat similar construction to adapter member 236 and includes circumferentially spaced locking ears 272a which are lockably receivable within slots 76a of base assembly connector 76. Unlike the previously described fill assembly 234, this latest fill assembly comprises first and second, side-by-side fill assemblies generally designated in the drawings by the numerals 274 and 296 respectively. Each of the fill assemblies is interconnected with, and is in fluid communication with, a hollow cannula 278 which is provided on adapter member 272. In a manner presently to be described, cannula 278 is adapted to pierce septum 80 of the base assembly 202 (FIG. 54).

Figure 52:
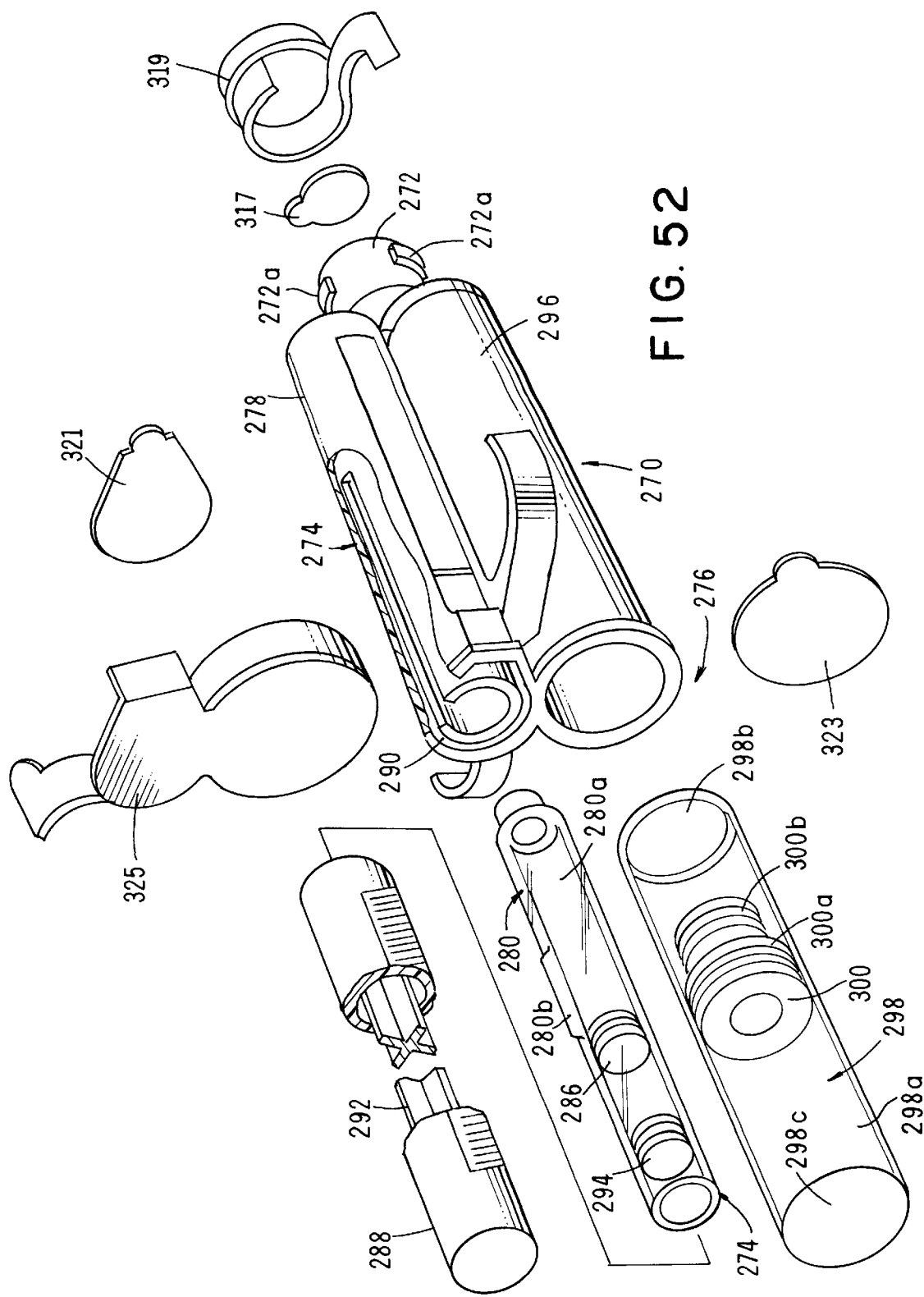
FIG. 52 is a generally perspective, exploded view of the dual vial reservoir fill assembly shown in FIG. 51.

Referring particularly to FIGS. 52 and 53, first assembly 274 includes an adapter housing 278 that is of similar construction to adapter housing 240 and is adapted to receive a container or vial assembly 280 which uniquely contains a lyophilized drug 282 that is separated from a reconstituting fluid 284 by a barrier stopper 286 (FIG. 53). Lyophilized drug 282 can, by way of example, comprise anti-infectives or various other types of beneficial agents. Vial assembly 280 is telescopically receivable within a pusher housing 288 that is similar to pusher housing 260. Pusher housing 288 is, in turn, receivable within an annular shaped opening 290 formed within housing 278 of the dual housing 270. As before, pusher housing 288 includes a pusher member 292 that engages a plunger 294 (FIG. 54) to push it forwardly of the container assembly to cause mixing of the fluid 284 with the lyophilized drug 282. This novel mixing step will be described more fully in the paragraphs which follow.

Second fill assembly 276 includes a housing 296 which accepts a fluid container 298 that includes a fluid chamber 298a. Container 298 has a first open end 298b that is sealably closed by a plunger assembly 300 and a closed second end 298c. In the manner shown in FIG. 54, container 298 is telescopically receivable within housing 296 of the second fill assembly 276. Plunger assembly 300 includes a body portion 300a and a threaded connector portion 300b which can be threadably interconnected with a pusher member 302 provided interiorly of housing 296 in the manner illustrated in FIG. 54. In this regard, pusher member 302 includes a head portion 302a that is internally threaded to receive connector portion 300b of plunger assembly 300 (FIG. 54). Pusher assembly 302 also includes a hollow cannula 304 that extends into an interior chamber defined by a threaded portion 302b. With this construction, when plunger assembly 300 is threadably interconnected with pusher member 302 in the manner shown in FIG. 54, hollow cannula 304 will pierce a central wall 307 formed in body 300a thereby opening fluid communication between fluid chamber 298a and the internal passageway of hollow cannula 304. An inward pressure exerted on container 298 will then urge the fluid contained within fluid chamber 298a to flow into hollow cannula 304 and then into a chamber 308 formed in housing 296 that houses a conventional umbrella check valve 310 (FIG. 54). Fluid under pressure will then flow past umbrella valve 310 into passageway 312 formed in adapter 272 and then into the internal passageway of piercing cannula 278. It is to be understood that the fluid contained within chamber 298a can take various forms as, for example, a diluent or a beneficial agent of some type. When the second fill assembly 274 of this latest form of the invention is mated with base assembly 202 in the manner shown in FIG. 54, cannula 278 will pierce septum 80 thereby permitting fluid to flow into reservoir 156 in the manner previously discussed.

Considering once again the novel first fill assembly 274 and referring particularly to FIGS. 52, 53, and 54 container assembly 280 as presented to pusher housing 288 includes a vial 280a that is sealed at one end by a plunger 294 and at the other end by a pierceable septum 314 (FIGS. 53 and 54). Formed intermediate the ends of vial 280a is a raised outer wall portion 280b which permits fluid 284 to bypass barrier stopper 286 as the barrier stopper is urged inwardly of the container by pressure exerted thereon by the fluid 284. Fluid 284 exerts pressure on barrier member 286 as a result of pusher member 292 exerting inward pressure on plunger 294, which pressure is, in turn, caused by the inward movement of plunger 294 as pusher housing 288 is pushed inwardly of second fill assembly housing 296.

Once assembly 270 is mated with base assembly 202 in a manner shown in FIG. 54, a continued inward pressure exerted on pusher housing 288 will cause fluid 284 to flow past barrier member 286 via wall portion 280b and will reconstitute lyophilized drug 282. Further pressure exerted on pusher housing 288 will cause the reconstituted drug formed by the fluid 284 which has been intermixed with drug 282 to flow through a hollow cannula, 287 past check valve 289, into fluid passageway 312, then through hollow cannula 278, past check valve 78, into passageway 208a, then into passageway 206, and finally into fill tube 164. From fill tube 164 the reconstituted drug will flow into reservoir 156 causing elastomeric membrane 158 to expand outwardly in the manner indicated by the dotted lines in FIG. 54. Prior to use, adapter portion 272 is substantially sealed by a peel cover 317 and a tear-away cap 319. Similarly, prior to loading container assemblies 280 and 298, both of the housings 278 and 296 as well as the fill assembly 270 are sealably closed by peel covers 321 and 323 and a tear-away cap 325 (FIG. 52).

To interconnect fill assembly 270 with base assembly 202, adapter member 272 is mated with connector 76 of the base assembly with the bayonet locking ears 272a thereof being received within the circumferentially spaced slots 76a formed in connector 76. Relative rotation of the fill assembly and the base assembly will effect a sterile interconnection of the fill assembly and the base assembly. As the fill assembly is aseptically mated with the base assembly, cannula 278 of the fill assembly will pierce the pierceable septum 80 which is mounted within connector 76. This done, an inward pressure exerted either sequentially or simultaneously on pusher housing 288 and container 298 and will cause fluid to flow toward the base assembly and into reservoir 156.

Figures 55, 56, 57:
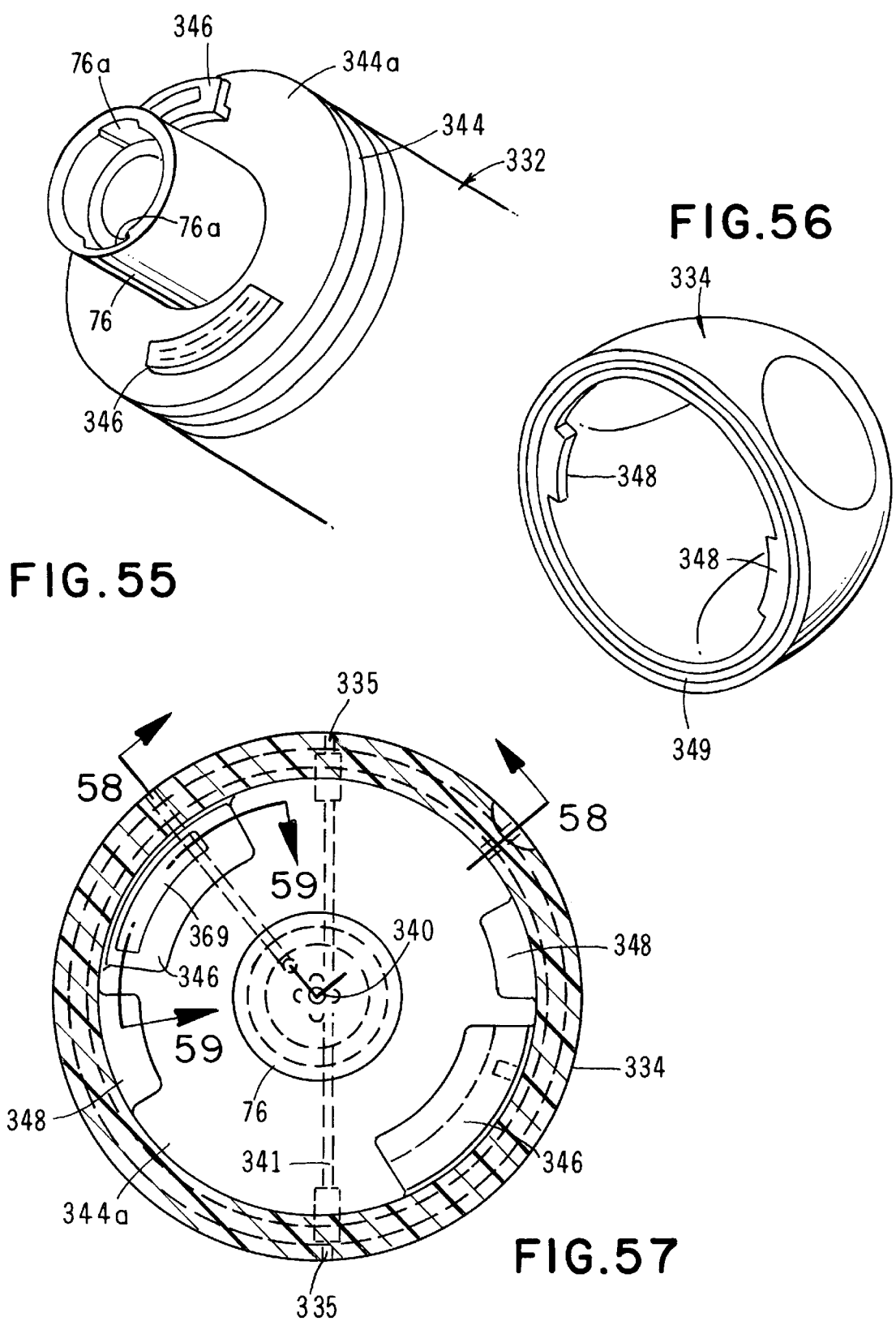
FIG. 55 is a generally perspective view of the base assembly of an alternate form of delivery device.
FIG. 56 is a generally perspective, exploded view of the cover assembly of the alternate form of delivery device shown in FIG. 55.
FIG. 57 is a top plan view of the delivery device partly broken away to show the bayonet-type connector means of the device for interconnecting the cover assembly with the base assembly.

Referring next to FIGS. 55 through 62, yet another embodiment of the invention is there shown. This embodiment of the invention is quite similar to that shown in FIGS. 41 through 50 and like numerals are used in FIGS. 55 through 62 to identify like components. Once again, the apparatus here comprises a generally egg-shaped housing which includes a slightly different base assembly 332 (FIG. 55) as well as a slightly different cover assembly 334 (FIG. 56). Formed within an internal chamber 153a of a base component 153 of base assembly 332, is a fluid reservoir 156 for containing the beneficial agent to be delivered to the ruminant (FIG. 58). Fluid reservoir 156 is formed by an elastomeric distendable member 158, which as in the earlier described embodiments, is distended into the configuration shown in FIG. 58, by the introduction of the beneficial agent into the device via the fill means of the invention.

The apparatus of this latest form of the invention also includes a heat-expandable means, or mass 162, which is carried within a chamber 153a and functions in the manner previously described to controllably urge fluids contained within reservoir 156 to flow outwardly into the rumen of the ruminant through the delivery means of the invention which includes a pair of diametrically opposed outlets 335 of the character shown FIG. 57.

Figure 63:
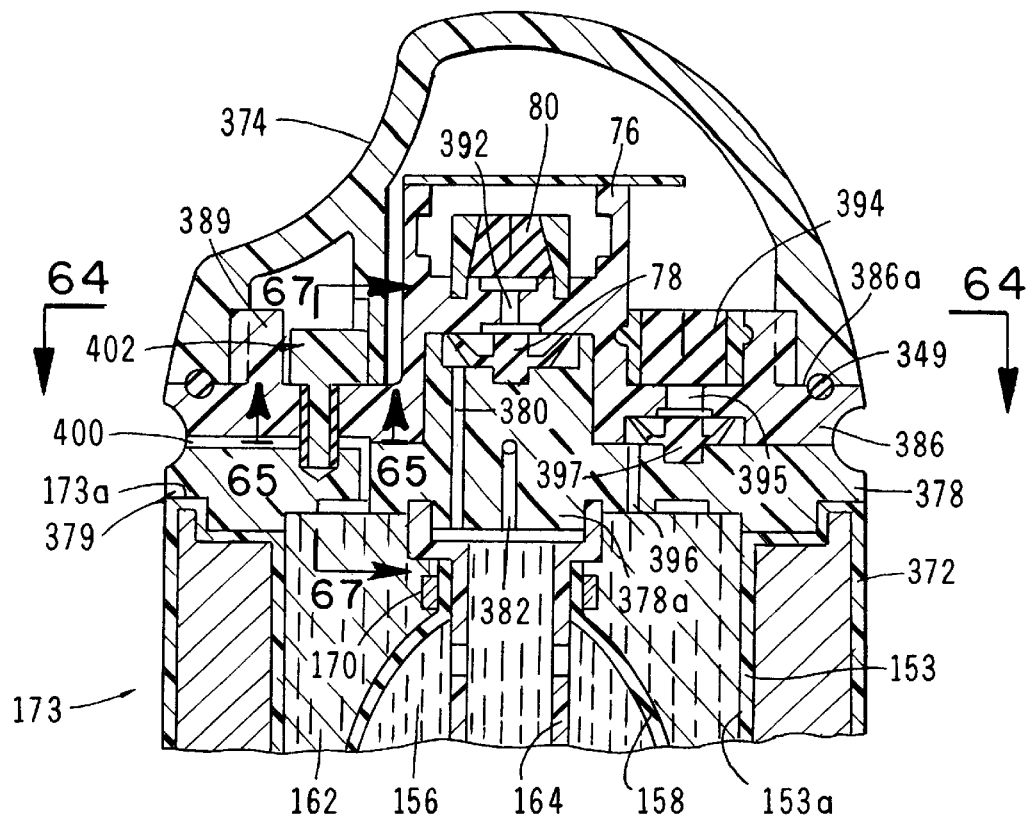
FIG. 63 is a fragmentary, side-elevational, cross-sectional view of an alternate form of the delivery device of the invention having a different type of vent closure means and including gel filling means for filling the device with gel in the field.

Turning particularly to FIGS. 58 and 63, a fill tube 164 extends into chamber 153a and cooperates with elastomeric member 158 to form reservoir 156 when the beneficial agent is introduced into the fill tube by the fill means of the invention. As in the earlier described embodiments, when the heat expandable mass 162 is heated by the body heat of the ruminant, it will expand and act upon distendable member 158 in a manner to tend to return the member toward its starting configuration and to controllably force the fluid, which is contained within the reservoir 156, outwardly of the device, through the delivery means, and into the rumen of the animal.

As before, member 158 is held in position within chamber 153a by means of a manifold 336 having a generally cylindrically shaped neck 336a that extends into chamber 153a (FIG. 58). The open mouth of elastomeric member 158 is receivable over neck 336a and a clamping ring 170 functions to maintain the elastomeric member in sealing engagement with neck 336a in the manner shown in FIGS. 58 and 63. Manifold component 336 includes a peripheral portion 337 which butts up against an edge 173a of a base member 173 that forms a part of base assembly 332. When the manifold component 336 is disposed in engagement with base member 173, in the manner shown in the drawings, both the fill tube and elastomeric member protrude into chamber 153a and are surrounded by heat expandable means 162. As indicated in FIG. 58, manifold component 336 is provided with a fill passageway 338 which is in communication with the interior of fill tube 164 and is also provided is a delivery passageway 340 that is also in communication with the interior of fill tube 164. As before, this passageway communicates with a transverse delivery passageway 341 that, in turn, communicates with outlet ports 335 (FIG. 57).

Disposed in engagement with manifold 336 is a second manifold 344 which can be interconnected with cover assembly 334 by means of a bayonet-type connector. This bayonet-type connector here comprises circumferentially spaced, generally "L" shaped brackets 346 that are affixed to the upper surface 344a of manifold 344 and circumferentially spaced locking ears 348 formed on the interior surface of cover assembly 334 (FIG. 56). Upon relative rotation between cover assembly 334 and base assembly 332, the assemblies will be securely interconnected and maintained in sealed engagement by an elastomeric O-ring 349 (FIG. 58). Second manifold 344 also includes an inlet passageway 351 that is in communication with inlet passageway 338 of first manifold 336 in the manner shown in FIG. 58. Second manifold 344 further includes first and second counterbores 354 and 356 respectively (see FIG. 58), which support check valve 78, that is of the character previously described.

As in the earlier described embodiments, this latest embodiment of the invention is also provided with novel vent closure means 360 for opening and closing vent a passageway 362 formed in manifolds 336 and 344 respectively (FIG. 58). Vent passageway 362 is necessary to vent chamber 153a during reservoir filling at which time elastomeric member 158 expands into chamber 153a. As best seen in FIGS. 59 through 61, this novel vent closure means comprises a unique shut off member 366 that includes a generally cylindrical body 366a having an elastomeric sleeve 367 and a resiliently deformable, outwardly extending spring tab 366b. As shown in FIG. 59, sleeve 367 is closely received within a bore 368 formed in manifold 344 and is movable by locking ears 348 of cover assembly 334 from a flow open position shown in FIG. 59 to a flow closed position shown in FIG. 60 wherein body portion 366a blocks gas flow through vent passageway 362. During the coupling of the cover assembly and base assembly, spring tab 366b is cammed downwardly by ears 348 in the manner shown in FIG. 60 and is received within a relief 369 formed in the top surface of manifold 344. With this novel construction, once cover assembly 334 is coupled with base assembly 332, the vent control means is inaccessible unless cover assembly 334 is removed.

Turning to FIGS. 63 through 69, another embodiment of the invention is there shown. This embodiment of the invention is quite similar to that shown in FIGS. 55 through 62 and like numerals are used to identify like components. Once again, the apparatus here comprises a generally egg-shaped housing which includes a slightly different base assembly 372 as well as a slightly different cover assembly 374 (FIG. 68). Formed within an internal chamber of 153a of a base component 153 of base assembly 372, is a fluid reservoir 156 for containing the beneficial agent to be delivered to the ruminant (FIG. 63). Fluid reservoir 156 is formed by an elastomeric distendable member 158, which as in the earlier described embodiments, is distended into the configuration shown in FIGS. 58 and 63, by the introduction of the beneficial agent into the device via the fill means of the invention.

Figure 64:
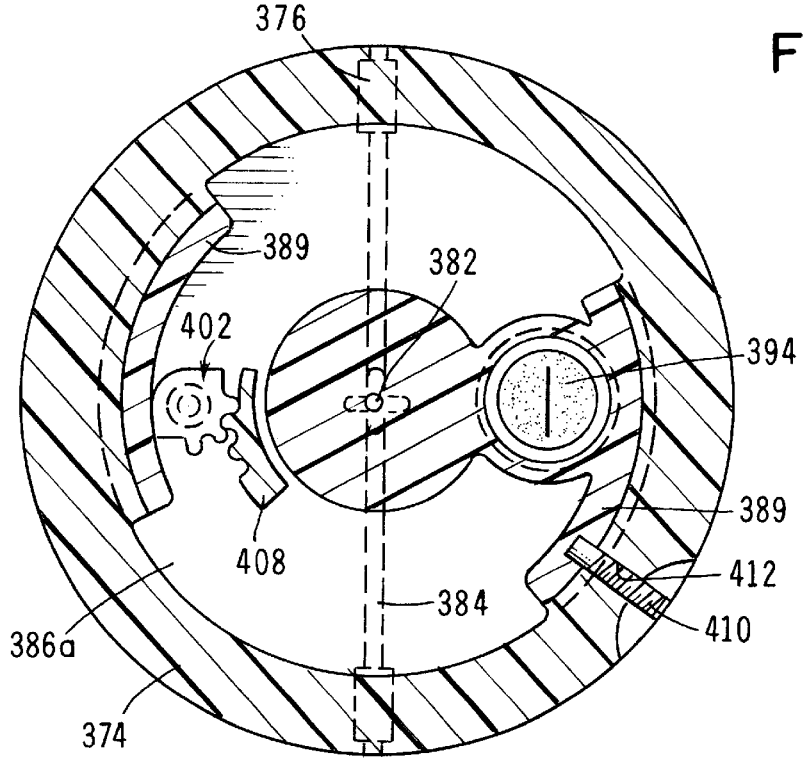
FIG. 64 is a cross-sectional view taken along lines 64—64 of FIG. 63.

The apparatus of this latest form of the invention also includes a heat-expandable means, or mass 162, which is carried within a chamber 153a and functions in the manner previously described to controllably urge fluids contained within reservoir 156 to flow outwardly into the rumen of the ruminant through the delivery means of the invention which includes a pair of diametrically opposed outlets 376 of the character shown FIG. 64.

As before, a fill tube 164 extends into chamber 153*a* and cooperates with elastomeric member 158 to form reservoir 156 when the beneficial agent is introduced into the fill tube by the fill means of the invention. As in the earlier described embodiments, when the heat expandable mass 162 is heated by the body heat of the ruminant, it will expand and act upon distendable member 158 in a manner to tend to return the member toward its starting configuration and to controllably force the fluid, which is contained within the reservoir 156, outwardly of the device, through the delivery means, and into the rumen of the animal.

In this latest embodiment of the invention, member 158 is held in position within chamber 153*a* by means of fill tube 164 which fits over a generally cylindrically shaped neck 378*a* provided in manifold 378. The open mouth of elastomeric member 158 is receivable over neck fill tube 164 in the manner shown in FIG. 63 and a clamping ring 170 functions to maintain the elastomeric member in sealing engagement with fill tube 164. Manifold component 378 includes a peripheral portion 379 which butts up against an edge 173*a* of a base member 173 that forms a part of base assembly 372. When the manifold component 378 is disposed in engagement with base member 173, in the manner shown in the drawings, both the fill tube and elastomeric member protrude into chamber 153*a* and are surrounded by heat expandable means 162. As indicated in FIG. 63, manifold component 378 is provided with a fill passageway 380 which is in communication with the interior of fill tube 164 and is also provided with a delivery passageway 382 that is also in communication with the interior of fill tube 164 (FIGS. 63 and 64). As before, this passageway communicates with a transverse delivery passageway 384 that, in turn, communicates with outlet ports 376 (FIG. 64).

Disposed in engagement with manifold 378 is a second manifold 386 which can be interconnected with cover assembly 374 by means of circumferentially spaced female closure clamps 389 which are affixed to the upper surface 386*a* (FIGS. 63 and 64) of manifold 386 and circumferentially spaced apart closure threads 390 formed on the interior surface of cover assembly 374 (FIG. 68). Upon relative rotation between cover assembly 374 and base assembly 372, the assemblies will be securely interconnected and maintained in sealed engagement by an elastomeric O-ring 349 (FIG. 63). Second manifold 386 also includes an inlet passageway 392 that is in communication with inlet passageway 380 of first manifold 378 via check valve 78 in the manner shown in FIG. 63. Second manifold 386 further includes first and second counterbores that support check valve 78, in the manner previously described. In this latest embodiment of the invention, manifolds 378 and 386 also carry a slit septum 394 which can be used to introduce gel 162 into chamber 153*a* via passageways 395 and 396 formed in manifolds 386 and 378 respectively. An umbrella-type check valve 397 is carried by manifold 386 to control gel flow toward and away from chamber 153*a*. Septum 394 is of conventional construction and is pierceable by a cannula of a conventional syringe assembly carrying gel 162.

As in the earlier described embodiments, this latest embodiment of the invention is also provided with novel vent closure means for opening and closing vent passageway 400 formed in manifolds 378 and 386 respectively (FIG. 63). Vent passageway 400 is necessary to vent chamber 153*a* during reservoir filling at which time elastomeric member 158 expands into chamber 153*a*. As best seen in FIGS. 64 through 69, this novel vent closure means comprises a unique control member 402 that includes a generally cylindrical body 404 having an elastomeric sleeve 405 and a transverse bore 404*a* therethrough (FIG. 69). Body 404 is rotatably received within bores 378*a* and 386*b* formed in manifolds 378 and 386 (FIG. 67). Control member 402 also includes a pinion-like head portion 406 having a plurality of spaced-apart teeth 406*a*. Teeth 406*a* are adapted to engage a rack-like member 408 formed on the inner wall of cover 374. As cover 374 is rotated to mate with base assembly 372, head portion 406 will be rotated by the teeth 408*a* on rack 408 from the first position shown in FIG. 65 wherein bore 404*a* of cylindrical portion 404 is aligned with vent passageway 400 to the second position shown in FIG. 66 wherein bore 404*a* is misaligned with vent passageway 400 thereby blocking the flow of gases therethrough. With this novel construction, mating of cover assembly 374 with base assembly 372 will automatically close vent passageway 400. Locking means, shown here as a cover locking pin 410 is insertable into a bore 412 formed in cover 374 to block counter rotation of cover 374 (FIG. 64).

Referring next to FIGS. 70 through 75, one form of the dispensing apparatus of the invention for dispensing to an animal a fluid delivery device is there shown and generally designated by the numeral 420. This novel dispensing apparatus is usable with a fluid delivery device of the same general character as the devices heretofore described and like numerals are used to identify like components. More particularly, the fluid delivery device includes a generally egg shaped housing having a base portion within which is a disposed a heat expandable means such as gel 162 and a weight such as weight 203*a* for retaining the fluid delivery device within the rumen of the animal (FIG. 70). However, in this latest form of the invention, the fluid delivery device housing, which is designated in FIG. 70 by the numeral 422 includes a generally cylindrically shaped cavity 424 having a circumferentially extending recess 426 provided therein. As earlier described, the dispensing apparatus functions to position the delivery device within the throat of the animal so that the animal will swallow the device.

Referring to FIG. 71 wherein the dispensing apparatus is shown connected with the fluid delivery device housing 422, the dispensing apparatus can be seen to comprise an elongated generally tubular shaped barrel 428 and a gripping mechanism 429 that is suitably interconnected with barrel 428. Barrel 428 is of a length such that, when inserted into the throat of the animal the outboard or gripping end of the barrel is behind the tongue or even deeper in the animal's throat. When the fluid delivery device is then released in a manner presently to be described, the animal will swallow the fluid delivery device rather than coughing or spitting it out. After the delivery device is swallowed, it will reside within the animal's rumen during the prescribed delivery period.

Figure 74:
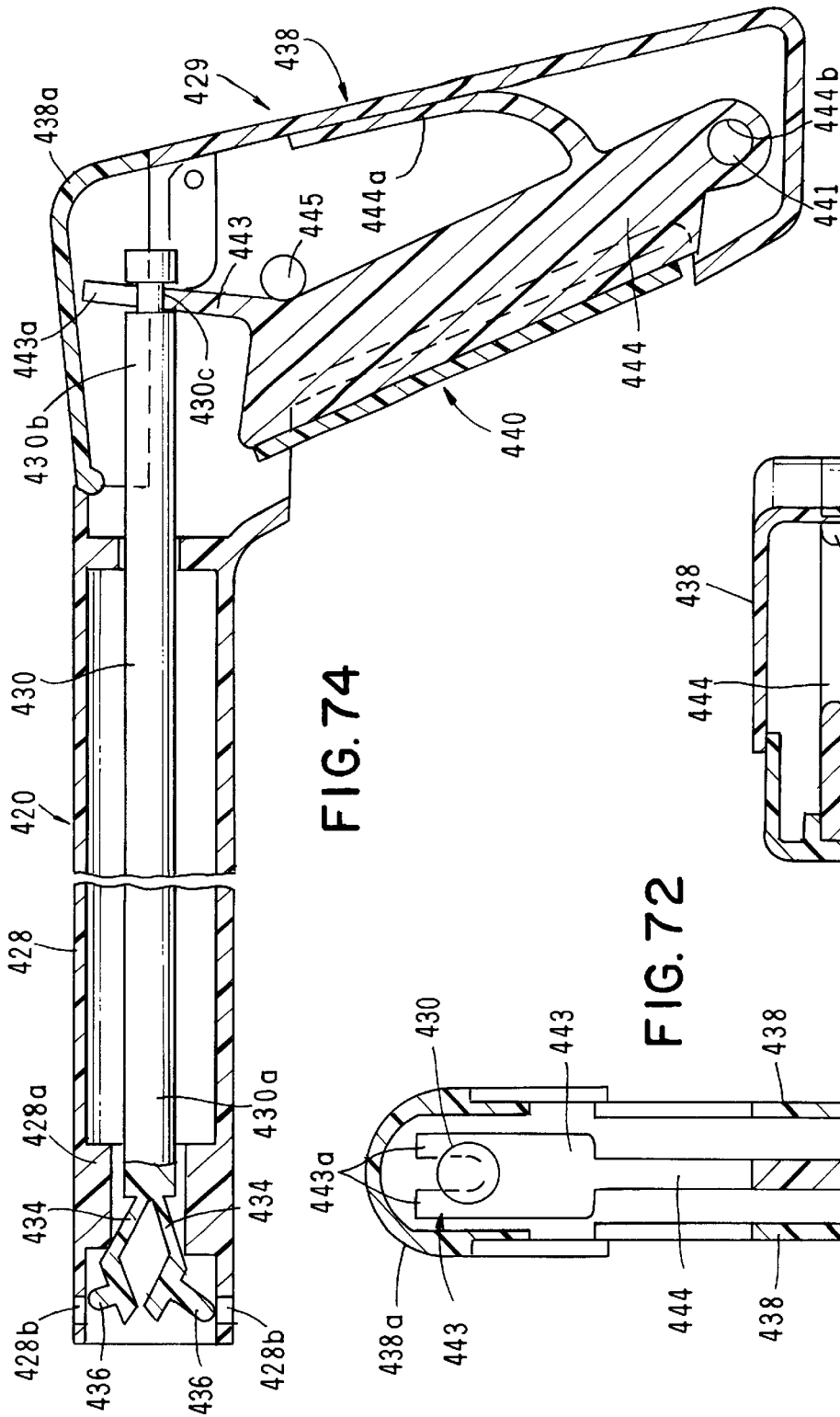
FIG. 74 is a foreshortened, cross-sectional view similar to FIG. 71 but showing the hand-operated dispensing apparatus separated from the fluid delivery device.
Figure 73:
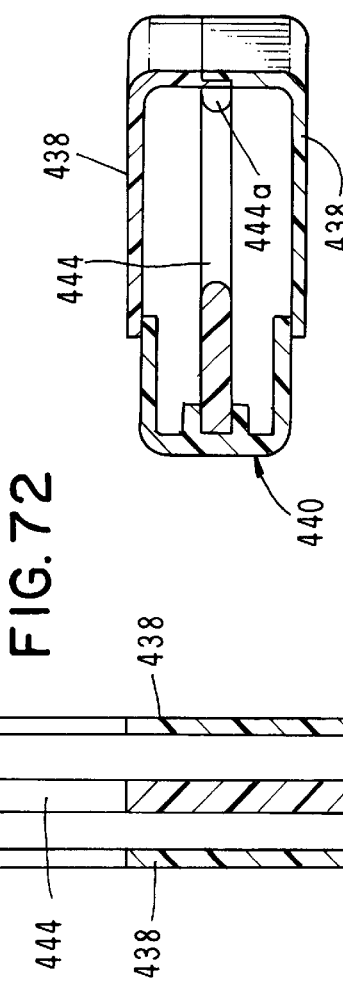
FIG. 73 is a cross-sectional view taken along lines 73—73 of FIG. 71.
Figure 72:
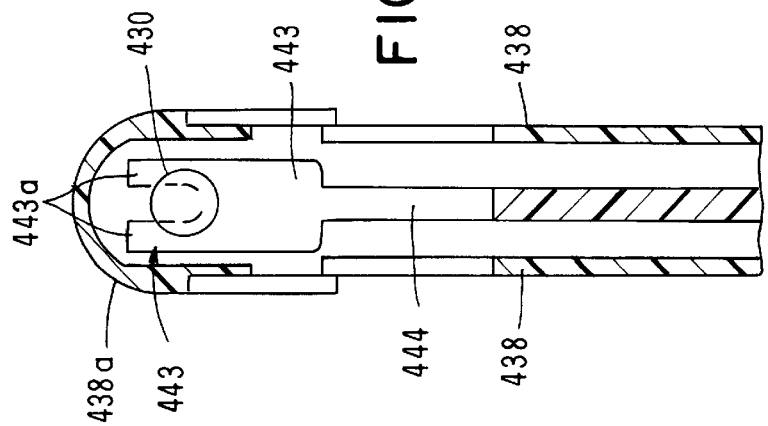
FIG. 72 is a cross-sectional view taken along lines 72—72 of FIG. 71.

Telescopically movable within barrel portion 428 is an operating member 430 having a first or forward end 430*a* and a second end 430*b*. Operably associated with operating member or rod 430 is the important connector means of this form of the invention for releasably interconnecting the dispensing apparatus with the housing 422 of the delivery device. The connector means of the invention is operable by the operating rod from the first engagement position shown in FIG. 71 to the second, retracted position shown in FIG. 74. As indicated in the drawings, the connector means of the present embodiment of the invention comprises a plurality of resiliently deformable fingers 434 each having an outwardly extending, recess-engaging element 436 (see particularly FIGS. 71, 74, and 75). As shown in FIG. 71, when the operating rod 430 is in the first or forward most position, recess-engaging elements 436 extend into the recess 426 formed in cavity 424 of the fluid delivery device. Conversely, when operating rod 430 is moved by the trigger mechanism of the apparatus into its second or retracted position as shown in FIG. 74, a reduced diameter portion 428*a* of barrel 428 will cammingly engage fingers 434 moving them into the retracted position wherein they are contained interiorly of the barrel. In this retracted position, recess engaging elements 436 have traveled through circumferentially spaced openings 428*b* formed proximate the forward end of barrel 428. With the connector means in this retracted or released position, the fluid delivery device can be readily separated from the dispensing apparatus so that it can be swallowed by the ruminant.

The novel gripping mechanism of the embodiment of the invention shown in FIGS. 70 through 75 comprises a handheld grip 438 which houses a trigger mechanism 440 that is of the construction best seen in FIG. 75. Mechanism 440 is pivotally connected to hand grip 438 for pivotal movement about a pivot pin 441 carried by grip 438 from a first position shown in FIG. 71 to a second position shown in FIG. 74. Operating means, shown here as an outwardly extending fork-like element 443 (FIG. 75) operably interconnects trigger mechanism 440 with operating rod 430 to enable movement of said operating rod from the first engagement position shown in FIG. 71 to the second retracted or release position shown in FIG. 74 (see also FIG. 75). As indicated in FIG. 75, operating rod 430 is provided with a circumferentially extending groove 430*c* that receives the prongs 443*a* of element 443. Also forming part of the gripping mechanism of the invention is biasing means for urging the trigger mechanism toward the first position shown in FIG. 71. In this position, the operating rod is urged forwardly of barrel portion 428 and into a position wherein the connector means of the invention interconnects the dispensing apparatus with the fluid delivery means housing 422. In the form of the invention shown in FIGS. 70 through 75, this biasing means comprising a yieldably deformable spring member 444*a* that is connected to the body portion 444 of the trigger mechanism. Body portion 444 is provided with a bore 444*b* that closely receives pivot pin 441 in the manner shown in FIG. 74.

As best seen in FIG. 75, the barrel and hand grip portions of the dispensing apparatus are each constructed in two halves which are joined together to form the assembly shown in FIGS. 71 and 74. When so assembled, the operating rod is disposed interiorally of barrel portion 428 and the trigger mechanism 440 is disposed within the hand grip portion 438. A rear cover 438*a* closes the rearward portion of the apparatus so as to encase the operating components in the manner shown in FIGS. 71 and 74.

In using the dispensing apparatus of the present form of the invention, with the gripping mechanism 429 gripped by the hand of the user, an inward force exerted by the fingers will cause an inward pivotal movement of trigger mechanism 440 which, in turn, will cause retraction of the operating rod into the position shown in FIG. 74. As the trigger mechanism is squeezed against the urging of the biasing means or spring element 444*a*, the trigger element will move into engagement with the trigger stop pin 445 (FIG. 74). With the trigger mechanism in this position, operating rod 430 has been moved rearwardly by fork-like element 443 and reduced diameter portion 428*a* of the barrel has cammed the connector means inwardly into the retracted position shown in FIG. 74. With the apparatus in this configuration, the outboard end of the barrel can be readily inserted into the cavity 424 of the filled fluid delivery device. A relaxation of the finger pressure exerted against trigger 440 will then permit spring 444*a* to urge the trigger mechanism and rod 430 into their initial starting position shown in FIG. 71. As the operating rod 430 moves forwardly locking elements 436 will extend through slots 428*b* formed in barrel 428 and will enter recess 426 formed in cavity 424 thereby securely locking the dispensing apparatus to the fluid delivery device (see FIG. 71). The fluid delivery device and the barrel portion of the dispensing apparatus can then be inserted into the animal's mouth to a position where the delivery device is rearwardly of the animal's tongue. With the delivery device in this position, a finger pressure exerted on the trigger 440 will once again cause retraction of the operating rod 430 to the second, or retracted position shown in FIG. 74. As the operating rod 430 is retracted, the connector means will once again be moved into the configuration shown in FIG. 74 thereby releasing the fluid delivery device so that it can be swallowed by the animal.

Figure 76:
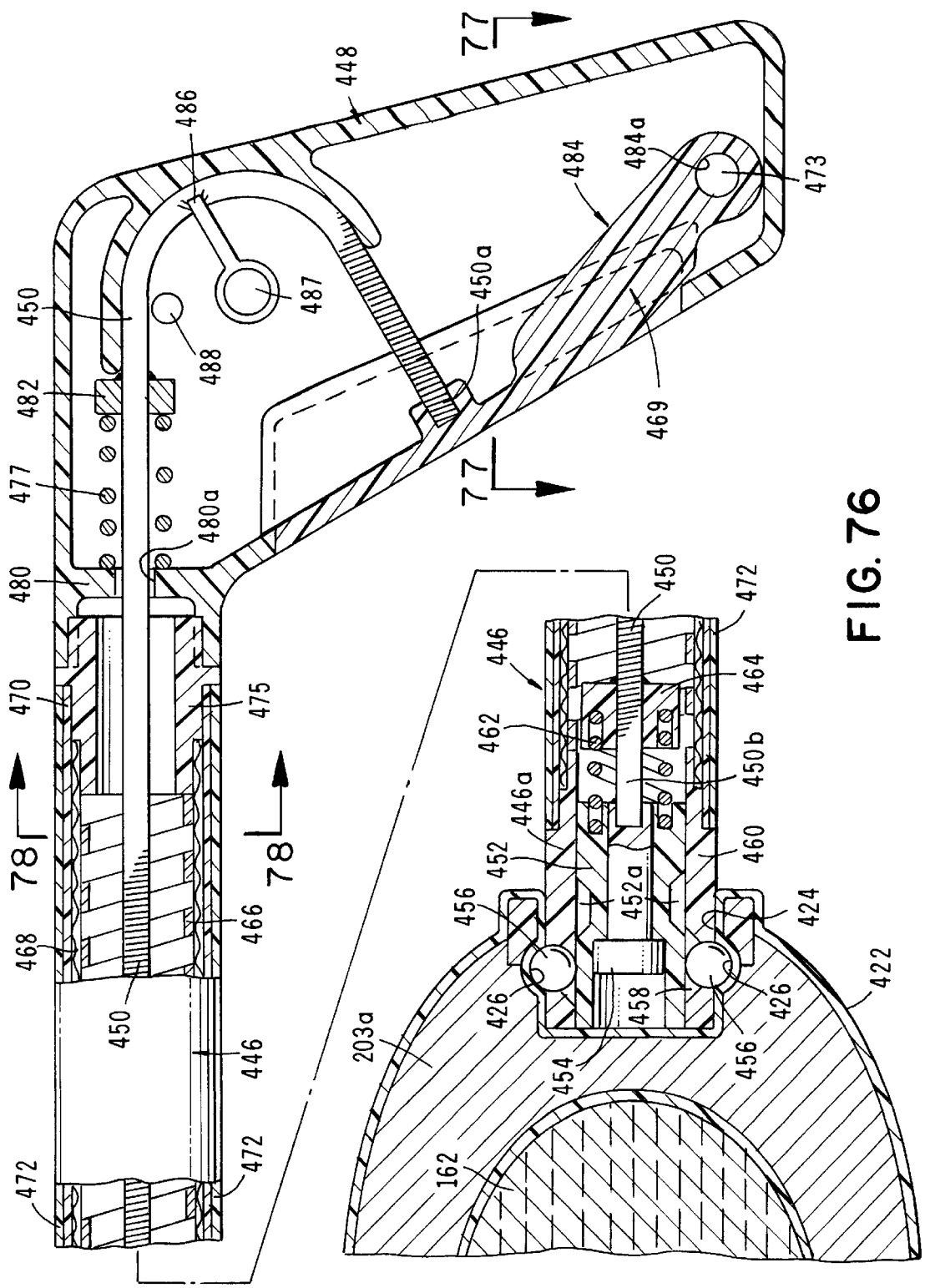
FIG. 76 is a side-elevational, cross-sectional view of an alternate form of dispensing apparatus of the invention shown interconnected with an alternate form of modified delivery device.
Figure 78:
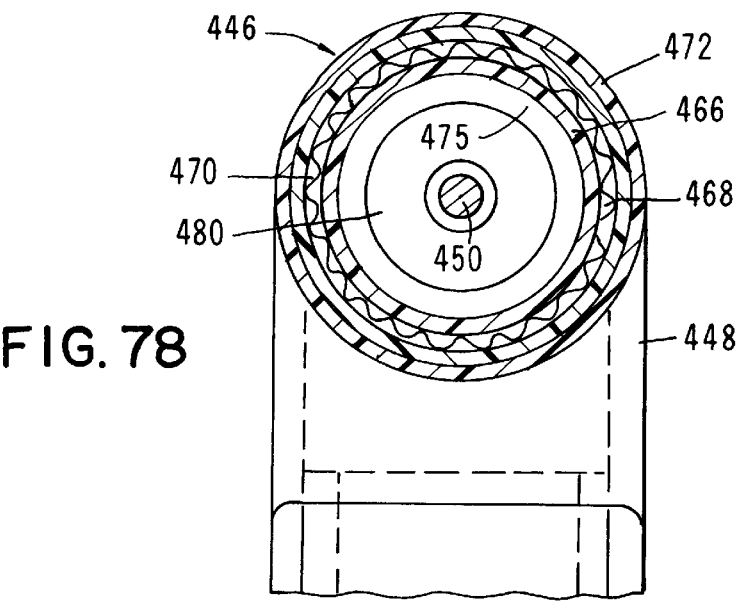
FIG. 78 is a cross-sectional view taken along lines 78—78 of FIG. 76.

Turning next to FIGS. 76 through 80, another form of the dispensing apparatus of the invention is there shown interconnected with a modified fluid delivery device. This apparatus is similar in construction and operation to that shown in FIGS. 70 through 75 and like numerals are used to identify like components. However, in this latest form of the invention, the barrel portion, which is generally designated by the numeral 446 is of a different construction and is flexible whereas barrel portion 428 of the previously described embodiment is rigid. As before, the dispensing apparatus of this latest embodiment is usable with a fluid delivery device of the same general character as the devices heretofore described, but having a generally cylindrically shaped cavity 424 provided with a circumferentially extending recess 426 (FIG. 76).

Referring particularly to FIG. 76, this latest form of the dispensing apparatus of the invention can be seen to comprise, in addition to flexible barrel 446, a gripping mechanism 448 that is suitably interconnected with barrel 446. Barrel 446, like barrel 428, is of a length such that, when inserted into the throat of the animal, the delivery device-gripping end of the barrel is located behind the tongue or even deeper in the animal's throat.

Telescopically movable within barrel portion 446 is an elongated operating member 450 having a first end 450*a* connected to gripping mechanism 448 and a second end 450*b* disposed within barrel 446. Operably associated with operating member or spring 450 is the important connector means of this latest form of the invention for releasably interconnecting the dispensing apparatus with the housing 422 of the delivery device. The connector means of the invention is movable by the operating spring from the device engagement position shown in FIG. 76 to the second, retracted or released position shown in FIG. 81. The connector means of this latest embodiment of the invention comprises a guide sleeve 452 that is telescopically movable within barrel 446, a pusher member 454 that is telescopically movable within guide sleeve 452 and a plurality of circumferentially spaced spherical, locking members 456 that are rotatably carried within pockets 458 formed in a ball retaining housing 460 which is connected to the outboard end 446*a* of barrel 446 (FIG. 79).

Figure 79:
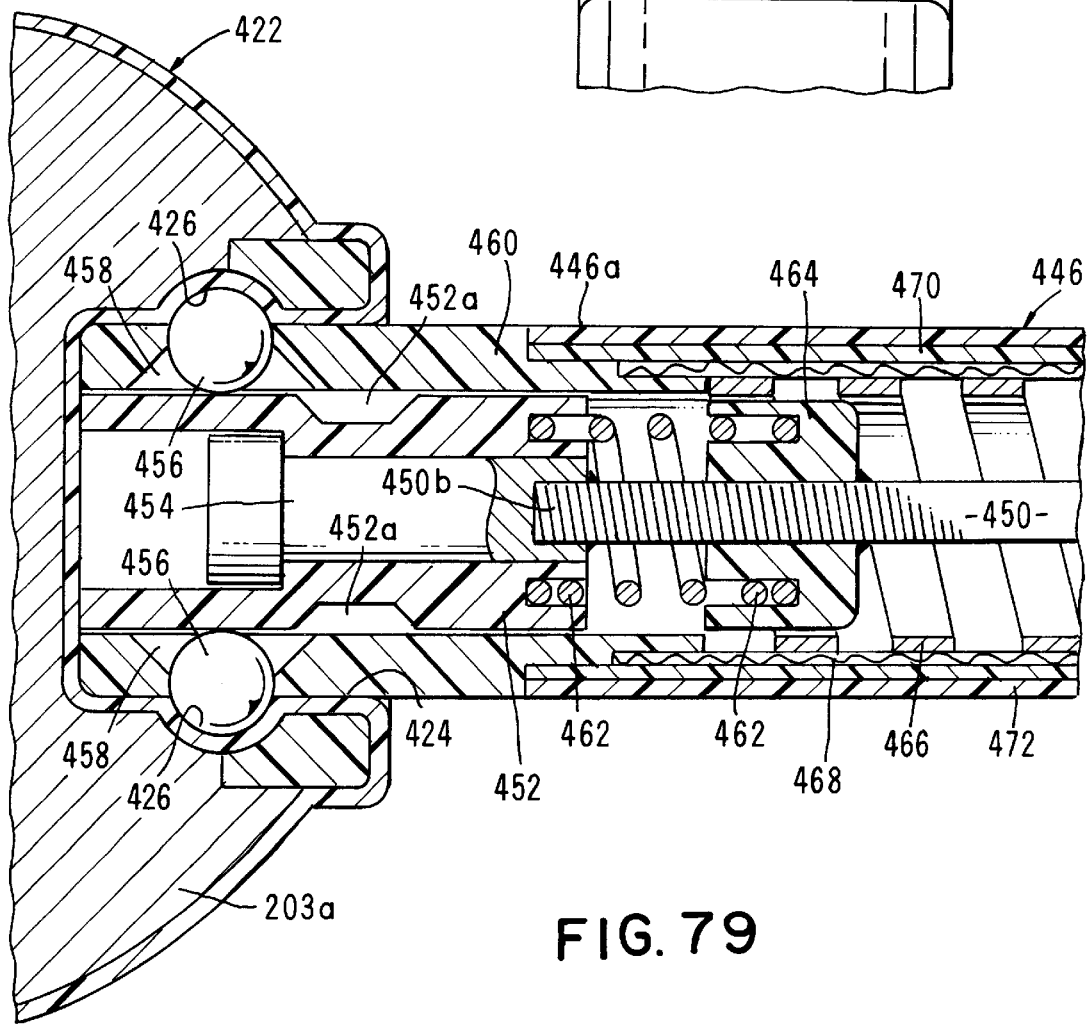
FIG. 79 is greatly enlarged, fragmentary, side-elevational, cross-sectional view of the connector portion of the dispensing device shown interconnected with the modified delivery device.

As shown in FIGS. 76 and 79, when the operating spring 450 is in the first, or rearward most position, members 456 are disposed within recess 426 formed in cavity 424 of the fluid delivery device. However, when operating spring 450 is moved by the trigger mechanism into its second, or advanced position shown in FIG. 81, sleeve 452 will be moved into its forward position by a coil spring 462 which is acted upon by a pusher block 464 to which spring 450 is connected as by soldering. As sleeve 452 moves forwardly within ball retaining housing 460 recess 452a formed in sleeve 452 will move into index with spherical members 456 causing them to move out of recess 426 and into recess 452a. As spherical members 456 clear recess 426, the fluid delivery device will, in the manner shown in FIG. 81 separate from the dispensing apparatus due to the urging of the forward extremity or sleeve 452 and pusher block 464 thereby freeing the delivery device so that it can be swallowed by the ruminant.

As best seen in FIG. 79, pusher block 464 moves within a flexible helix 466 which is carried within a flexible metal braid tube 468 that is, in turn, disposed with an elongated high polymer tube 470. With this construction, helix 466, metal braid tube 468 and high polymer tube 470 cooperate with an outer polymer tube 472 to make up flexible barrel 446. The flexibility of barrel 446 assists in administering the fluid delivery device to the ruminant and helps to prevent injury to the animal during the dispensing step.

The gripping mechanism of the embodiment of the invention shown in FIGS. 76 through 81 is somewhat similar to that previously described and comprises a hand-held grip 448 which houses a slightly differently configured trigger mechanism 469. Trigger mechanism 469 is pivotally connected to hand grip 448 for a pivotal movement about a pivot pin 473 from a first position shown in FIG. 76 to a second position shown in FIG. 81. Drive spring 450, which comprises the operating means of this latest embodiment of the invention, operably interconnects trigger mechanism 469 with pusher block 464 and with pusher member 454 to enable movement of these components from the first device engagement position shown in FIG. 76 to the second advanced or release position shown in FIG. 81.

Figure 80:
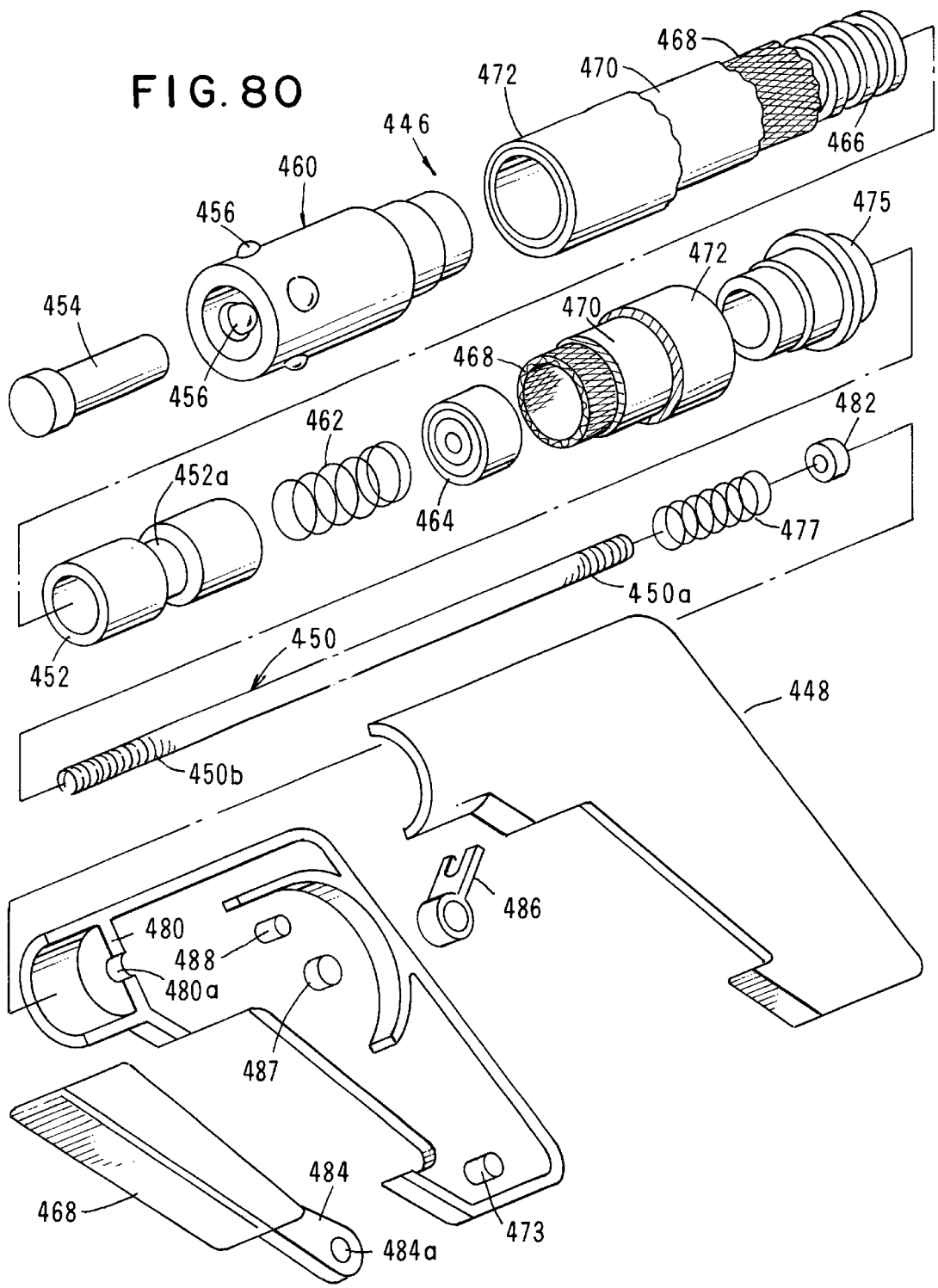
FIG. 80 is a generally perspective, exploded view of the dispensing apparatus of this latest form of the invention.

As indicated in FIGS. 76 and 80, hand grip 448 is interconnected with barrel 446 by means of a coupler component 475, the forward portion of which is received within metal braid tube 468. As before, biasing means, shown here as a coil spring 477, urges the trigger mechanism toward the starting position shown in FIG. 76. Spring 477 is housed with grip 448 with one end thereof in engagement with a guide wall 480 and the other end in engagement with a washer 482 which is affixed to drive spring 450 (see also FIG. 80). Guide wall 480 has a central bore 480a that assists in guiding the reciprocal movement of drive spring 450 within barrel 446. Body portion 484 of trigger 469 is provided with a bore 484a that closely received pivot pin 473 in the manner shown in FIG. 71.

As indicated in FIG. 80, the hand grip portion of the dispensing apparatus is constructed in two halves which can be joined together to form the grip assembly shown in FIGS. 76 and 77. When the grip assembly is interconnected with coupler component 475 in the manner shown in FIG. 76, end 450a of the operating spring will be anchored interiorally of the hand grip and the operating spring will be entrained through the hand grip, through opening 480a in wall 480 and then longitudinally of barrel portion 446.

Figure 81:
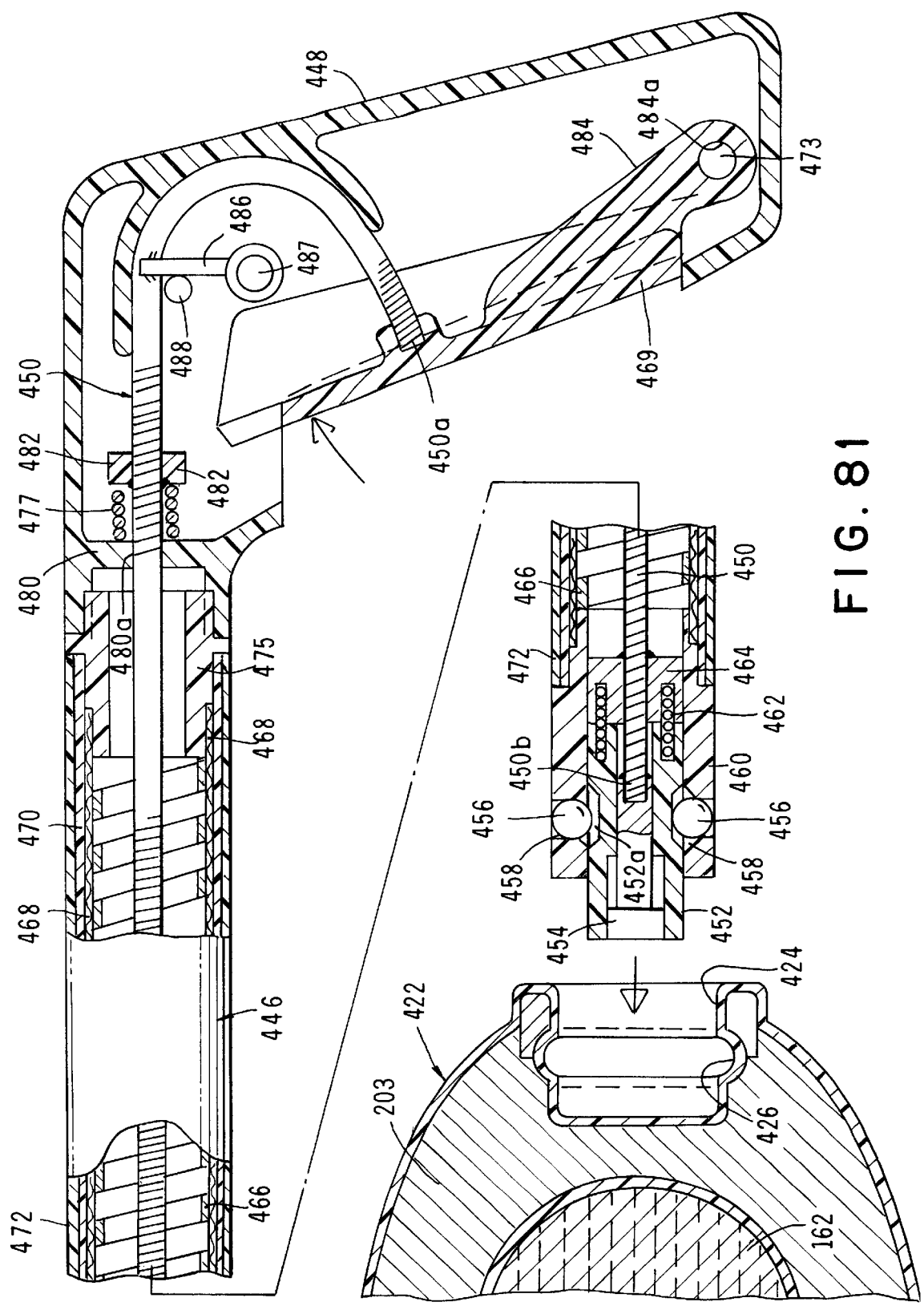
FIG. 81 is a side-elevational, cross-sectional view similar to FIG. 76, but showing the dispensing apparatus separated from the modified delivery device.

In using the sensing apparatus of this latest form of the invention, with the hand grip portion 448 gripped by the hand of the user, an inward force exerted by the fingers will cause inward pivotal movement of trigger mechanism 469 which, in turn, will cause forward movement of the operating spring into the position shown in FIG. 81. As the trigger mechanism is squeezed against the urging of the biasing means or spring 477, a drive spring swing arm 486, which is affixed to drive spring 450, will pivot about a pivot pin 487 and into engagement with a stop pin 488 (FIG. 81) thereby stopping forward movement of the drive spring. With the trigger in the position shown in FIG. 81, the operating spring has advanced sleeve 452 to a location wherein spherical members 456 will drop into recess 452a. At the same time, pusher member 454 will advance into pushing engagement with the fluid delivery device causing it to separate from the dispensing apparatus. A relaxation of the finger pressure exerted on trigger 469 will permit springs 462 and 477 to urge the operating components into their original starting position. To connect the dispensing apparatus with another delivery device, the trigger needs to be depressed so as to permit the outboard end ball retainer 460 to be inserted into the cavity 424 formed in the fluid dispensing device. Release of finger pressure will then cause spherical members 456 to move into locking engagement within recess 426 in the manner shown in FIGS. 76 and 79.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

What is claimed is:

1. A device for administering beneficial agents to a ruminant at a controlled rate comprising:
   (a) a housing;
   (b) distendable means for forming, in conjunction with said housing, a reservoir having an inlet and an outlet, said distendable means comprising at least one distendable membrane, at least one portion of which is movable within said housing from a first position to a second position;
   (c) heat expandable means disposed within said housing in proximity to said distendable membrane, said heat expandable means comprising a semi-solid, which, upon being heated, will act upon said distendable membrane to move said membrane toward said second position to cause fluid within said reservoir to flow outwardly of said outlet of said reservoir; and
   (d) delivery means in communication with said outlet of said reservoir for delivering the beneficial agent from said reservoir to the ruminant.

2. The device as defined in claim 1 in which said heat expandable means comprises a heat expandable gel.

3. The device as defined in claim 1 in which said heat expandable means substantially surrounds said distendable membrane.

4. The device as defined in claim 1 further including a weight disposed within said housing.

5. The device as defined in claim 1 further including fill means carried by said housing for filling said reservoir with the beneficial agent.

6. The device as defined in claim 1 in which said housing is generally egg shaped and includes a base portion and a generally hemispherically shaped cover.

7. The device as defined in claim 1 in which said housing includes an internal chamber, said heat expandable means being disposed within said internal chamber, said housing including vent means for venting said internal chamber.

8. A device as defined in claim 7 in which said vent means comprises a vent passageway, said device further including vent control means carried by said housing for controlling flow through said vent passageway.

9. The device as defined in claim 7 further including means for introducing said heat expandable means into said housing.

10. A device for administering beneficial agents to a ruminant at a controlled rate said device being insertable into the rumen of the ruminant and comprising:
 (a) a housing;
 (b) a fill tube disposed with said housing, said fill tube having inlet and outlet ports;
 (c) a distendable, elastomeric member for forming, in conjunction with said fill tube, a fluid reservoir in communication with said inlet and outlet ports of said fill tube, said elastomeric member being movable within said housing from a first position to a second position;
 (d) heat expandable means disposed within said housing in proximity with said elastomeric member, said heat expandable means comprising a heat expandable gel, which, upon being heated, will act upon said elastomeric member to move said member toward said second position to cause fluid within said reservoir to flow outwardly of said outlet of said outlet ports of said fill tube; and
 (e) delivery means in communication with said outlet of said fill tube for delivering the beneficial agent from said reservoir to the ruminant.

11. The device as defined in claim 10 further including a weight disposed within said housing, said weight being of a sufficient density to cause the housing to be retained within the rumen.

12. The device as defined in claim 10 further including fill means carried by said housing for filling said reservoir with the beneficial agent.

13. The device as defined in claim 10 in which said housing includes a base component having an interior chamber.

14. The device as defined in claim 13 further including means for introducing said heat expandable means into said interior chamber.

15. The device as defined in claim 13 in which said housing is generally egg shaped and includes a base assembly and a generally hemispherically shaped cover sealably connected to said base assembly.

16. The device as defined in claim 15 in which said base assembly comprises:
 (a) a base component;
 (b) a first manifold connected to said base component, said first manifold having both a fill passageway and a delivery passageway in communication with said fill tube; and
 (c) a second manifold connected to said first manifold, said second manifold having a fill passageway in communication with said fill passageway of said first manifold and a delivery passageway in communication with said delivery passageway of said first manifold.

17. The device as defined in claim 16 further including connector means for connecting said cover to said second manifold.

18. The device as defined in claim 16 in which said base assembly includes vent means for venting said interior chamber to atmosphere.

19. The device as defined in claim 18 further including vent control means for controlling the flow of gases through said vent means.

\* \* \* \* \*